United States Patent
Gohl et al.

(10) Patent No.: US 9,540,598 B2
(45) Date of Patent: *Jan. 10, 2017

(54) DETERGENTS CAPABLE OF CLEANING, BLEACHING, SANITIZING AND/OR DISINFECTING TEXTILES INCLUDING SULFOPEROXYCARBOXYLIC ACIDS

(71) Applicant: Ecolab USA Inc., St. Paul, MN (US)

(72) Inventors: David W. Gohl, Eagan, MN (US); Robert D. P. Hei, Baldwin, WI (US); Thomas Merz, Hilden (DE); Peter Jens Forth, Dusseldorf (DE); Matthias Kreysel, Herrliberg (CH); David D. McSherry, St. Paul, MN (US); Junzhong Li, Apple Valley, MN (US); Jonathan P. Fast, St. Paul, MN (US)

(73) Assignee: Ecolab USA Inc., St. Paul, MN (US)

( * ) Notice: Subject to any disclaimer, the term of this patent is extended or adjusted under 35 U.S.C. 154(b) by 31 days.

This patent is subject to a terminal disclaimer.

(21) Appl. No.: 14/482,256

(22) Filed: Sep. 10, 2014

(65) Prior Publication Data

US 2015/0026900 A1 Jan. 29, 2015

Related U.S. Application Data

(63) Continuation of application No. 13/221,613, filed on Aug. 30, 2011, now Pat. No. 8,871,807, which is a continuation-in-part of application No. 12/413,189, filed on Mar. 27, 2009, now Pat. No. 8,344,026.

(60) Provisional application No. 61/040,444, filed on Mar. 28, 2008.

(51) Int. Cl.

| | |
|---|---|
| A61K 31/19 | (2006.01) |
| C07D 303/34 | (2006.01) |
| A01N 37/00 | (2006.01) |
| C11D 3/395 | (2006.01) |
| A01N 41/04 | (2006.01) |
| A01N 41/08 | (2006.01) |
| A23B 4/20 | (2006.01) |
| A23B 5/14 | (2006.01) |
| A23L 3/3535 | (2006.01) |
| C07D 303/16 | (2006.01) |
| C11D 3/20 | (2006.01) |
| C11D 3/28 | (2006.01) |
| C11D 3/33 | (2006.01) |
| C11D 3/36 | (2006.01) |
| C11D 3/39 | (2006.01) |
| C11D 3/48 | (2006.01) |
| C11D 11/00 | (2006.01) |
| C07C 409/42 | (2006.01) |

(52) U.S. Cl.
CPC ............. *C11D 3/3955* (2013.01); *A01N 41/04* (2013.01); *A01N 41/08* (2013.01); *A23B 4/20* (2013.01); *A23B 5/14* (2013.01); *A23L 3/3535* (2013.01); *C07C 409/42* (2013.01); *C07D 303/16* (2013.01); *C11D 3/2075* (2013.01); *C11D 3/2079* (2013.01); *C11D 3/28* (2013.01); *C11D 3/33* (2013.01); *C11D 3/364* (2013.01); *C11D 3/3945* (2013.01); *C11D 3/3947* (2013.01); *C11D 3/48* (2013.01); *C11D 11/0017* (2013.01)

(58) Field of Classification Search
USPC ........................................ 514/557, 506, 709
See application file for complete search history.

(56) References Cited

U.S. PATENT DOCUMENTS

| | | | |
|---|---|---|---|
| 2,609,391 | A | 9/1952 | Greenspan et al. |
| 3,053,633 | A | 9/1962 | Dunlop et al. |
| 3,130,169 | A | 4/1964 | Blumbergs et al. |
| 3,156,654 | A | 11/1964 | Konecny et al. |
| 3,414,593 | A | 12/1968 | Robson et al. |
| 3,956,159 | A | 5/1976 | Jones |
| 3,969,258 | A | 7/1976 | Carandang et al. |
| 4,051,059 | A | 9/1977 | Bowing et al. |
| 4,100,095 | A | 7/1978 | Hutchins et al. |
| 4,126,573 | A | 11/1978 | Johnston |
| 4,129,517 | A | 12/1978 | Eggensperger et al. |
| 4,170,453 | A | 10/1979 | Kitko |
| 4,259,201 | A | 3/1981 | Cockrell, Jr. et al. |
| 4,297,298 | A | 10/1981 | Crommelynck et al. |

(Continued)

FOREIGN PATENT DOCUMENTS

| | | |
|---|---|---|
| CA | 2084172 C | 3/1998 |
| CA | 2152908 C | 3/2006 |

(Continued)

OTHER PUBLICATIONS

"Recommendations on the Transport of Dangerous Goods, Manual of Tests and Criteria", 5th revised edition (2009), UN , sect. 28.4.4, p. 314.

(Continued)

*Primary Examiner* — Shobha Kantamneni
(74) *Attorney, Agent, or Firm* — McKee, Voorhees & Sease, PLC

(57) ABSTRACT

The present invention relates to novel combined laundry detergent, bleach, and antimicrobial composition incorporating novel sulfoperoxycarboxylic acid compounds, and methods for making and using them. The sulfoperoxycarboxylic compounds used in compositions of the invention are storage stable, water soluble and have low to no odor. Compositions of the invention may be in the form of a liquid, a solid, or a gel. The sulfoperoxycarboxylic compounds useful in preparing compositions of the present invention can be formed from non-petroleum based renewable materials.

23 Claims, 10 Drawing Sheets

(56) References Cited

U.S. PATENT DOCUMENTS

| | | |
|---|---|---|
| 4,311,598 A | 1/1982 | Verachtert |
| 4,374,035 A | 2/1983 | Bossu |
| 4,391,723 A | 7/1983 | Bacon et al. |
| 4,391,724 A | 7/1983 | Bacon |
| 4,430,236 A | 2/1984 | Franks |
| 4,470,919 A | 9/1984 | Goffinet et al. |
| 4,473,507 A | 9/1984 | Bossu |
| 4,529,534 A | 7/1985 | Richardson |
| 4,540,721 A | 9/1985 | Staller |
| 4,587,264 A | 5/1986 | Jourdan-Laforte et al. |
| 4,783,278 A | 11/1988 | Sanderson et al. |
| 4,786,431 A | 11/1988 | Broze et al. |
| 4,797,225 A | 1/1989 | Broze et al. |
| 4,846,992 A | 7/1989 | Fonsny |
| 4,879,057 A | 11/1989 | Dankowski et al. |
| 4,917,815 A | 4/1990 | Beilfuss et al. |
| 5,004,558 A | 4/1991 | Dyroff et al. |
| 5,073,285 A | 12/1991 | Liberati et al. |
| 5,098,598 A | 3/1992 | Sankey et al. |
| 5,117,049 A | 5/1992 | Venturello et al. |
| 5,139,788 A | 8/1992 | Schmidt |
| 5,160,656 A | 11/1992 | Carron et al. |
| 5,200,189 A | 4/1993 | Oakes et al. |
| 5,250,212 A | 10/1993 | de Buzzaccarini et al. |
| 5,250,707 A | 10/1993 | Inaba et al. |
| 5,264,229 A | 11/1993 | Mannig et al. |
| 5,266,587 A | 11/1993 | Sankey et al. |
| 5,268,003 A | 12/1993 | Coope et al. |
| 5,274,369 A | 12/1993 | Tsunoda et al. |
| 5,288,746 A | 2/1994 | Pramod |
| 5,296,239 A | 3/1994 | Colery et al. |
| 5,314,687 A | 5/1994 | Oakes et al. |
| 5,349,083 A | 9/1994 | Brougham et al. |
| 5,362,899 A | 11/1994 | Campbell |
| 5,374,369 A | 12/1994 | Angevaare et al. |
| 5,382,571 A | 1/1995 | Granger et al. |
| 5,409,629 A | 4/1995 | Shulman et al. |
| 5,415,807 A | 5/1995 | Gosselink et al. |
| 5,431,848 A | 7/1995 | Getty |
| 5,433,881 A | 7/1995 | Townend et al. |
| 5,435,808 A | 7/1995 | Holzhauer et al. |
| 5,447,648 A | 9/1995 | Steindorf |
| 5,453,214 A | 9/1995 | van den Berg et al. |
| 5,463,112 A | 10/1995 | Sankey et al. |
| 5,466,825 A | 11/1995 | Carr et al. |
| 5,472,619 A | 12/1995 | Holzhauer et al. |
| 5,496,728 A | 3/1996 | Hardy et al. |
| 5,525,121 A | 6/1996 | Heffner et al. |
| 5,565,231 A | 10/1996 | Malone et al. |
| 5,589,507 A | 12/1996 | Hall, II et al. |
| 5,624,634 A | 4/1997 | Brougham et al. |
| 5,632,676 A | 5/1997 | Kurschner et al. |
| 5,635,195 A | 6/1997 | Hall, II et al. |
| 5,637,755 A | 6/1997 | Nagumo et al. |
| 5,672,739 A | 9/1997 | Varadaraj et al. |
| 5,683,977 A | 11/1997 | Jureller et al. |
| 5,691,298 A | 11/1997 | Gosselink et al. |
| 5,698,506 A | 12/1997 | Angevaare et al. |
| 5,718,910 A | 2/1998 | Oakes et al. |
| 5,767,308 A | 6/1998 | Thiele et al. |
| 5,814,592 A | 9/1998 | Kahn et al. |
| 5,840,343 A | 11/1998 | Hall, II et al. |
| 5,872,092 A | 2/1999 | Chan et al. |
| 5,914,303 A | 6/1999 | Sankey et al. |
| 5,929,012 A | 7/1999 | Del Duca et al. |
| 5,965,033 A | 10/1999 | Huss et al. |
| 5,965,785 A | 10/1999 | Braden et al. |
| 5,968,885 A | 10/1999 | Del Duca et al. |
| 5,968,893 A | 10/1999 | Manohar et al. |
| 5,977,403 A | 11/1999 | Byers |
| 6,004,922 A | 12/1999 | Watson et al. |
| 6,010,729 A | 1/2000 | Gutzmann et al. |
| 6,049,002 A | 4/2000 | Mattila et al. |
| 6,103,286 A | 8/2000 | Gutzmann et al. |
| 6,136,769 A | 10/2000 | Asano et al. |
| 6,156,156 A | 12/2000 | Rousu et al. |
| 6,165,483 A | 12/2000 | Hei et al. |
| 6,183,763 B1 | 2/2001 | Beerse et al. |
| 6,183,807 B1 | 2/2001 | Gutzmann et al. |
| 6,201,110 B1 | 3/2001 | Olsen et al. |
| 6,211,237 B1 | 4/2001 | Huss et al. |
| 6,238,685 B1 | 5/2001 | Hei et al. |
| 6,262,013 B1 | 7/2001 | Smith et al. |
| 6,277,804 B1 | 8/2001 | Kahn et al. |
| 6,284,793 B1 | 9/2001 | Fuchs et al. |
| 6,294,186 B1 | 9/2001 | Beerse et al. |
| 6,310,025 B1 | 10/2001 | Del Duca et al. |
| 6,346,279 B1 | 2/2002 | Rochon |
| 6,384,008 B1 | 5/2002 | Parry |
| 6,432,661 B1 | 8/2002 | Heitfeld et al. |
| 6,436,885 B2 | 8/2002 | Biedermann et al. |
| 6,444,634 B1 | 9/2002 | Mason et al. |
| 6,503,876 B1 | 1/2003 | Broeckx et al. |
| 6,528,471 B1 | 3/2003 | Del Duca et al. |
| 6,545,047 B2 | 4/2003 | Gutzmann et al. |
| 6,576,602 B1 | 6/2003 | Smerznak et al. |
| 6,607,710 B1 | 8/2003 | Ito et al. |
| 6,627,593 B2 | 9/2003 | Hei et al. |
| 6,627,657 B1 | 9/2003 | Hilgren et al. |
| 6,635,286 B2 | 10/2003 | Hei et al. |
| 6,686,324 B2 | 2/2004 | Ramirez et al. |
| 6,696,093 B2 | 2/2004 | Ney et al. |
| 6,770,774 B2 | 8/2004 | Van De Bovenkamp-Bouwman et al. |
| 6,803,057 B2 | 10/2004 | Ramirez et al. |
| 6,830,591 B1 | 12/2004 | Wang et al. |
| 6,866,749 B2 | 3/2005 | Belmas et al. |
| 6,919,304 B2 | 7/2005 | Dykstra et al. |
| 7,012,053 B1 | 3/2006 | Barnabas et al. |
| 7,061,036 B2 | 6/2006 | Kajiyama |
| 7,078,373 B2 | 7/2006 | Burrows et al. |
| 7,148,351 B2 | 12/2006 | Morris et al. |
| 7,169,236 B2 | 1/2007 | Zeiher et al. |
| 7,243,664 B2 | 7/2007 | Berger et al. |
| 7,448,255 B2 | 11/2008 | Hoots et al. |
| 7,498,051 B2 | 3/2009 | Man et al. |
| 7,524,803 B2 | 4/2009 | Lentsch et al. |
| 7,601,789 B2 | 10/2009 | Morris et al. |
| 7,618,545 B2 | 11/2009 | Wakao et al. |
| 7,723,083 B2 | 5/2010 | DiCosimo et al. |
| 7,771,737 B2 | 8/2010 | Man et al. |
| 7,875,720 B2 | 1/2011 | Morris et al. |
| 7,887,641 B2 | 2/2011 | Man et al. |
| 7,910,371 B2 | 3/2011 | Johnson |
| 7,922,828 B2 | 4/2011 | Smith et al. |
| 7,949,432 B2 | 5/2011 | Rice |
| 7,981,679 B2 | 7/2011 | Rice |
| 7,985,318 B2 | 7/2011 | Shevchenko et al. |
| 8,017,409 B2 | 9/2011 | Tokhtuev et al. |
| 8,030,351 B2 | 10/2011 | Gutzmann et al. |
| 8,071,528 B2 | 12/2011 | Smith et al. |
| 8,080,404 B1 | 12/2011 | Turetsky et al. |
| 8,110,603 B2 | 2/2012 | Kawabata et al. |
| 8,119,412 B2 | 2/2012 | Kraus |
| 8,153,573 B2 | 4/2012 | Miralles et al. |
| 8,178,336 B2 | 5/2012 | Derkx et al. |
| 8,226,939 B2 | 7/2012 | Herdt et al. |
| 8,231,917 B2 | 7/2012 | Herdt et al. |
| 8,236,573 B2 | 8/2012 | Tokhtuev et al. |
| 8,241,624 B2 | 8/2012 | Herdt et al. |
| 8,309,507 B2 | 11/2012 | Fernandez Prieto et al. |
| 8,344,026 B2 | 1/2013 | Li et al. |
| 2001/0054201 A1 | 12/2001 | Wang et al. |
| 2002/0007516 A1 | 1/2002 | Wang |
| 2002/0157189 A1 | 10/2002 | Wang et al. |
| 2002/0188026 A1 | 12/2002 | Singh et al. |
| 2003/0045443 A1 | 3/2003 | Korber et al. |
| 2003/0100468 A1 | 5/2003 | Smerznak et al. |
| 2003/0148909 A1 | 8/2003 | Del Duca et al. |
| 2003/0154556 A1 | 8/2003 | Del Duca et al. |
| 2003/0234382 A1 | 12/2003 | Sato et al. |
| 2003/0235623 A1 | 12/2003 | Van Oosterom |
| 2004/0010858 A1 | 1/2004 | Detering et al. |
| 2004/0016060 A1 | 1/2004 | Detering et al. |

(56) References Cited

U.S. PATENT DOCUMENTS

| | | |
|---|---|---|
| 2004/0025262 A1 | 2/2004 | Hamers et al. |
| 2004/0033269 A1 | 2/2004 | Hei et al. |
| 2004/0035537 A1 | 2/2004 | Delmas et al. |
| 2004/0072718 A1 | 4/2004 | Price et al. |
| 2004/0077514 A1 | 4/2004 | Price et al. |
| 2004/0107506 A1 | 6/2004 | Detering et al. |
| 2004/0139559 A1 | 7/2004 | Detering et al. |
| 2004/0266653 A1 | 12/2004 | Delplancke et al. |
| 2005/0000908 A1 | 1/2005 | Karlsson et al. |
| 2005/0222003 A1 | 10/2005 | Gagliardi et al. |
| 2005/0281773 A1 | 12/2005 | Wieland et al. |
| 2006/0113506 A1* | 6/2006 | Man .................. A01N 37/16 252/186.1 |
| 2006/0172909 A1 | 8/2006 | Schmiedel et al. |
| 2006/0257964 A1 | 11/2006 | Larose |
| 2007/0010420 A1 | 1/2007 | Lange et al. |
| 2007/0102359 A1 | 5/2007 | Lombardi et al. |
| 2007/0281002 A1 | 12/2007 | Morales et al. |
| 2008/0064619 A1 | 3/2008 | Bastigkeit et al. |
| 2008/0146482 A1 | 6/2008 | Schneiderman et al. |
| 2008/0194449 A1 | 8/2008 | Becker et al. |
| 2009/0005286 A1 | 1/2009 | Detering et al. |
| 2009/0047176 A1 | 2/2009 | Cregger et al. |
| 2009/0061017 A1 | 3/2009 | Pedersen et al. |
| 2009/0075856 A1 | 3/2009 | Schmiedel et al. |
| 2009/0145202 A1 | 6/2009 | Tokhtuev et al. |
| 2009/0188055 A1 | 7/2009 | Bernhardt et al. |
| 2009/0221704 A1 | 9/2009 | Aksela et al. |
| 2009/0269324 A1 | 10/2009 | Herdt et al. |
| 2009/0294382 A1 | 12/2009 | Fukuyo et al. |
| 2010/0021557 A1 | 1/2010 | Li et al. |
| 2010/0021558 A1 | 1/2010 | Dada et al. |
| 2010/0041579 A1 | 2/2010 | Bianchetti et al. |
| 2010/0048730 A1 | 2/2010 | Li et al. |
| 2010/0108566 A1 | 5/2010 | Scattergood et al. |
| 2010/0140186 A1 | 6/2010 | Huang et al. |
| 2010/0160449 A1 | 6/2010 | Rovison, Jr. et al. |
| 2010/0222242 A1 | 9/2010 | Huang et al. |
| 2011/0177145 A1 | 7/2011 | Erkenbrecher, Jr. et al. |
| 2011/0217761 A1 | 9/2011 | Hilgren et al. |
| 2012/0012307 A1 | 1/2012 | Nevin |
| 2012/0024525 A1 | 2/2012 | Svarczkopf et al. |
| 2012/0052134 A1 | 3/2012 | Li et al. |
| 2012/0070339 A1 | 3/2012 | Lawal |
| 2012/0085236 A1 | 4/2012 | McCorriston et al. |
| 2012/0085931 A1 | 4/2012 | Burns et al. |
| 2012/0097614 A1 | 4/2012 | Silva et al. |
| 2012/0149121 A1 | 6/2012 | Tokhtuev et al. |
| 2012/0172441 A1 | 7/2012 | Li et al. |
| 2012/0225943 A1 | 9/2012 | Gohl et al. |
| 2012/0321510 A1 | 12/2012 | Herdt et al. |
| 2013/0018097 A1 | 1/2013 | Bolduc et al. |
| 2013/0022496 A1 | 1/2013 | Herdt et al. |
| 2014/0096971 A1 | 4/2014 | Keizer et al. |
| 2014/0097144 A1 | 4/2014 | Li et al. |

FOREIGN PATENT DOCUMENTS

| | | |
|---|---|---|
| CN | 1020197 C | 3/1993 |
| CN | 1092385 A | 12/1993 |
| CN | 1117298 A | 10/1995 |
| CN | 1162132 A | 10/1996 |
| CN | 1231599 A | 10/1999 |
| CN | 1751768 A | 3/2006 |
| CN | 100486668 C | 5/2009 |
| CN | 102105443 A | 6/2011 |
| DE | 1024514 B | 2/1958 |
| DE | 19754290 A1 | 6/1999 |
| DE | 19853845 A1 | 5/2000 |
| DE | 10011273 A1 | 9/2001 |
| EP | 0075419 A3 | 11/1983 |
| EP | 0061393 B1 | 10/1984 |
| EP | 0122041 A1 | 3/1985 |
| EP | 0068547 B1 | 9/1985 |
| EP | 273775 A2 | 7/1988 |
| EP | 0280697 A1 | 9/1988 |
| EP | 273775 A3 | 4/1989 |
| EP | 0231632 A3 | 8/1989 |
| EP | 349220 A2 | 1/1990 |
| EP | 0384911 A2 | 8/1990 |
| EP | 387049 A2 | 9/1990 |
| EP | 0395902 A2 | 11/1990 |
| EP | 0396341 A2 | 11/1990 |
| EP | 0442549 A2 | 8/1991 |
| EP | 387049 A3 | 9/1991 |
| EP | 0233730 B1 | 4/1992 |
| EP | 0267047 B1 | 8/1993 |
| EP | 0626371 A1 | 11/1994 |
| EP | 0751210 A1 | 1/1997 |
| EP | 0751933 A1 | 1/1997 |
| EP | 0845526 A3 | 3/1999 |
| EP | 0906950 A1 | 4/1999 |
| EP | 1001012 A1 | 5/2000 |
| EP | 1099750 A2 | 5/2001 |
| EP | 0741776 B2 | 10/2001 |
| EP | 1099750 A3 | 9/2002 |
| EP | 1247802 B1 | 12/2004 |
| EP | 1717302 A1 | 11/2006 |
| EP | 1328616 | 7/2008 |
| EP | 1931628 B1 | 11/2010 |
| EP | 2271410 B1 | 10/2011 |
| EP | 2522714 A1 | 11/2012 |
| EP | 2522715 A1 | 11/2012 |
| EP | 1328616 B2 | 3/2015 |
| GB | 1041417 | 9/1966 |
| GB | 1198734 A | 7/1970 |
| GB | 1584170 A | 2/1981 |
| GB | 2172897 A | 10/1986 |
| GB | 2177716 A | 1/1987 |
| GB | 2178754 A | 2/1987 |
| GB | 2179364 A | 3/1987 |
| GB | 2179365 A | 3/1987 |
| GB | 2187199 A | 9/1987 |
| GB | 2195124 A | 3/1988 |
| GB | 2195125 A | 3/1988 |
| GB | 2208233 A | 3/1988 |
| GB | 2195649 A | 4/1988 |
| GB | 2279660 A | 1/1995 |
| GB | 2281744 A | 3/1995 |
| GB | 2361687 A | 10/2000 |
| JP | 60230000 | 11/1985 |
| JP | 6316534 A | 7/1988 |
| JP | 01297499 A | 11/1989 |
| JP | 3119174 | 5/1991 |
| JP | 05140079 | 6/1993 |
| JP | 05503507 A | 6/1993 |
| JP | 05507951 A | 11/1993 |
| JP | 06100531 A | 4/1994 |
| JP | 06503372 A | 4/1994 |
| JP | 6247924 | 9/1994 |
| JP | 06510526 A | 11/1994 |
| JP | 59206495 A | 11/1994 |
| JP | 8092594 | 4/1996 |
| JP | 8143898 | 6/1996 |
| JP | 8245549 | 9/1996 |
| JP | 09512042 A | 12/1997 |
| JP | 200505136 A | 4/2000 |
| JP | 2000357633 | 12/2000 |
| JP | 2002105352 A | 4/2002 |
| JP | 200645146 A | 2/2006 |
| JP | 200645147 A | 2/2006 |
| JP | 200645149 A | 2/2006 |
| JP | 2007084589 A | 4/2007 |
| JP | 2007520479 A | 7/2007 |
| JP | 2007523892 A | 8/2007 |
| JP | 2009500415 A | 1/2009 |
| JP | 2011518775 A | 6/2011 |
| JP | 2012126740 A | 7/2012 |
| JP | 2012126741 A | 7/2012 |
| JP | 2012126918 A | 7/2012 |
| JP | 2012149080 A | 8/2012 |
| NZ | 587218 | 4/2012 |
| WO | 9007501 A1 | 7/1990 |

(56) References Cited

FOREIGN PATENT DOCUMENTS

| | | |
|---|---|---|
| WO | 9107375 A1 | 5/1991 |
| WO | 9114674 | 10/1991 |
| WO | 9114674 A1 | 10/1991 |
| WO | 9115122 | 10/1991 |
| WO | 9115122 A1 | 10/1991 |
| WO | 9115474 A1 | 10/1991 |
| WO | 9314183 A1 | 7/1993 |
| WO | 9403395 A1 | 2/1994 |
| WO | 9403580 | 2/1994 |
| WO | 9403580 A1 | 2/1994 |
| WO | 9410284 A1 | 5/1994 |
| WO | 9413776 A1 | 6/1994 |
| WO | 9418299 A1 | 8/1994 |
| WO | 9419446 | 9/1994 |
| WO | 9419446 A1 | 9/1994 |
| WO | 9424869 A1 | 11/1994 |
| WO | 9616148 A1 | 11/1994 |
| WO | 9429509 A1 | 12/1994 |
| WO | 9502030 A1 | 1/1995 |
| WO | 9521122 A1 | 8/1995 |
| WO | 9521290 A1 | 8/1995 |
| WO | 9528471 A1 | 10/1995 |
| WO | 9528472 A1 | 10/1995 |
| WO | 9531527 | 11/1995 |
| WO | 9531527 A1 | 11/1995 |
| WO | 9533816 A1 | 12/1995 |
| WO | 9534269 | 12/1995 |
| WO | 9534269 A1 | 12/1995 |
| WO | 9610072 | 4/1996 |
| WO | 9610072 A1 | 4/1996 |
| WO | 9614384 A1 | 5/1996 |
| WO | 9633254 | 10/1996 |
| WO | 9633254 A1 | 10/1996 |
| WO | 9700938 | 1/1997 |
| WO | 9700938 A1 | 1/1997 |
| WO | 9732871 | 9/1997 |
| WO | 9732871 A1 | 9/1997 |
| WO | 9742286 A1 | 11/1997 |
| WO | 9743393 A2 | 11/1997 |
| WO | 9800518 A1 | 1/1998 |
| WO | 9800528 A1 | 1/1998 |
| WO | 9803513 A1 | 1/1998 |
| WO | 9805749 A1 | 2/1998 |
| WO | 9811102 A1 | 3/1998 |
| WO | 9811189 A1 | 3/1998 |
| WO | 9811777 A1 | 3/1998 |
| WO | 9818893 A1 | 5/1998 |
| WO | 9820116 A1 | 5/1998 |
| WO | 9919451 A1 | 4/1999 |
| WO | 9931215 A1 | 6/1999 |
| WO | 9932598 A1 | 7/1999 |
| WO | 9964556 A1 | 12/1999 |
| WO | 0042145 | 7/2000 |
| WO | 0042158 A1 | 7/2000 |
| WO | 0070951 | 11/2000 |
| WO | 0076963 | 12/2000 |
| WO | 0078911 | 12/2000 |
| WO | 0100765 | 1/2001 |
| WO | 0119414 | 3/2001 |
| WO | 0187358 | 11/2001 |
| WO | 02008076 | 11/2002 |
| WO | 02088076 | 11/2002 |
| WO | 03006581 | 1/2003 |
| WO | 03067989 | 8/2003 |
| WO | 03067989 A1 | 8/2003 |
| WO | 2004044266 | 5/2004 |
| WO | 2004044266 A1 | 5/2004 |
| WO | 2006118594 A1 | 11/2006 |
| WO | 2006118594 A3 | 1/2007 |
| WO | 2007008478 A1 | 1/2007 |
| WO | 2007066302 A2 | 6/2007 |
| WO | 2008005058 | 1/2008 |
| WO | 2008005058 A1 | 1/2008 |
| WO | 2009053686 A1 | 4/2009 |
| WO | 2009071664 A1 | 6/2009 |
| WO | 2009118714 A2 | 10/2009 |
| WO | 2011083295 A1 | 7/2011 |
| WO | 2011089313 A2 | 7/2011 |
| WO | 2011146557 A1 | 11/2011 |
| WO | 2012090124 A2 | 7/2012 |

OTHER PUBLICATIONS

"Recommendations on the Transport of Dangerous Goods, Model Regulations" (Rev.17) ST/SG/AC.10/1/Rev.17 (2011).
A.O.A.C. Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2).
A.O.A.C. Use Dilution Methods, Official Methods of Analysis of the Association of Official Analytical Chemists, paragraph 955.14 and applicable sections 15th Edition, 1990 (EPA Guidline 91.2).
Brooks, Robert E., et al., "Alkaline hydrogen peroxide bleaching of cellulose", Kluwer Academic Publishers, Cellulose 7: 263-286, 2000 (24 pages).
Carboni-Oerlemans, Chiara, et al., "Hydrolase-catalysed synthesis of peroxycarboxylic acids: Biocatalytic promiscuity for practical applications.", Elsevier, Journal of Biotechnology, 126 (2006) 140-151 (12 pages).
Chen, J., "Enhanced Alkaline Peroxide Bleaching of Softwood Kraft Pulps Using a New Activator," Journal of Pulp and Paper Science: vol. 27, No. 12, Dec. 2001 (4 pages).
Chung, L., et al., "Coordinative Binding of Divalent Cations with Ligands Related to Bacterial Spores", Biophysical Journal (1971) vol. 11, pp. 470-482.
Dannacher, Josef J., "Catalytic bleach: Most valuable applications for smart oxidation chemistry", Journal of Molecular Catalysis A: Chemical 251 (2006) 159-176.
Database Caplus Chemical Abstracts Service, Columbus, Ohio, US; Database Accession No. 1960:97225, Abstract of DE 1024514, Feb. 20, 1958 "Oxidation of organic compounds with hydrogen peroxide in the liquid phase".
"ECOLA8 USA, Inc. et al., PCT/IB2011/055830 filed Dec. 20, 2011, "Notification of Transmittal of the International Search Report and the Written Opinion of the International Searching Authority, or the Declaration" mailed Aug. 24, 2012, 8 pages."
"ECOLA8 USA, Inc. et al., PCT/IB2011/055832 filed Dec. 20, 2011, "Notification of Transmittal of the International Search Report and the Written Opinion of the International Searching Authority, or the Declaration" mailed Aug. 14, 2012, 14 pages."
Ecolab USA Inc., PCT/US2013/030904, filed on Mar. 13, 2013, "The International Search Report and the Written Opinion of the International Searching Authority, or the Declaration", mail date Jul. 5, 2013.
Ecolab USA Inc., PCT/US2013/063512 filed Oct. 4, 2013, "The International Search Report and Written Opinion", mailed Dec. 26, 2013, 10 pages.
Ecolab USA Inc., PCT/US2014/017283 filed Feb. 20, 2014, "Notification of Transmittal of the Internation Search Report and the Written Opinion of the International Searching Authority, or the Declaration", mailed Apr. 28, 2014.
Effkemann, Stefan, et al., "Peroxide analysis in laundry using liquid chromatography", Elsevier, Analytica Chimica Acta, 363 (1998) 97-103 (7 pages).
Katz, Jonathan, "Report: Fracking to Grow U.S. Water-Treatment Market Nine-Fold by 2020", http://www.industryweek.com/global-economy/report-fracking-grow-us-frack-water-treatment-market-nine-fold-2020, [retrieved from the internet on Jun. 6, 2012], pp. 1-2.
Lee, Jung Jin, et al., "Hydrolytic stability of a series of lactam-based cationic bleach activators and their impact on cellulose peroxide bleaching", Springer Science + Business Medica B.V., Cellulose (2010) 17:671-678 (8 pages).
Leistner (1995) In Gould GW (Ed.) New Methods of Food Preservation, Springer, pp. 1-21.
Leistner, "Basic aspects of food preservation by hurdle technology", International Journal of Food Microbiology, (2000) 55: 181-186.

(56) References Cited

OTHER PUBLICATIONS

Leveneur, Sebastien, "Synthesis of peroxypropionic acid from propionic acid and hydrogen peroxide over heterogeneous catalysts", Elsevier, Chemical Engineering Journal, 147 (2009) 323-329 (7 pages).

Li, Junzhong, U.S. Appl. No. 13/785,405, filed Mar. 5, 2013, 14 pages, Office Action mailed Oct. 22, 2013.

Maeda, et al., Assessment of Acyl Groups and Reaction Conditions in the Competition between Perhydrolysis and Hydrolysis of Acyl Resorufins for Developing an Indicator Reaction for Fluorometric Analysis of Hydrogen Peroxide Feb. 28, 2002.

Malow and Wehrstedt, "Prediction of the self-accelerating decomposition temperature (SADT) for liquid organic peroxides from differential scanning calorimetry (DSC) measurements", J. Hazard Mater. (2005) 120(1-3): 21-4.

"Muurinene, Esa, ""Organosolv Pulping—A review and distillation study related toperoxyacid pulping""", Department of Process Engineering, University of Oulu, May 16, 2000,Oulu, Finland (314 pages)."

Nowack, Bernd, "Environmental Chemistry of Phosphonates", Water Research (2003) vol. 37, No. 11, pp. 2533-2546.

"Ogata et al., ""Radical scavenging activities of niacin-related compounds""", Biosci. Biotechnol.Biochem., 2002, 66(3), 641-645."

Ogata, Y., et al., "The Formation of Peracids by the Perhydrolysis With Alkaline Hydrogen Peroxide", Tetrochem, vol. 23, pp. 3327-3332, Pergamom Press, 1967 (7 pages).

Popov, Konstantin, et al., "Critical Evaluation of Stability Constants of Phosphonic Acids", Pure Appl. Chem. (2001), vol. 73, No. 10, pp. 1641-1677.

Rizkalla, E.N., et al., "Metal Chelates of Phosphonate-Containing Ligands-V Stability of some 1-Hydroxyethane-1, 1-Diphosphonic Acid Metal Chelates", Talanta (1980), vol. 27, No. 9, pp. 715-719.

Rusch gen. Klaas, Mark, et al., "Biocatalytic peroxy acid formation for disinfection", Journal of Molecular Catalysis B: Enzymatic 19-20 (2002) 499-505.

Rusch gen. Klaas, Mark, et al., "Lipase-catalyzed conversions of trimethylsilyl ethers: deprotection, acetylation, epoxidation and one-pot-multi-step reactions", Journal of Molecular Catalysis B: Enzymatic 7 (1999) 283-289.

Rusch gen. Klaas, Mark, et al., "Lipase-catalyzed preparation of peroxy acids and their use for expoxidation", Elsevier, Journal of Molecular Catalysis A: Chemical 117 (1997) 311-319 (9 pages).

Suchy, Miro, et al., "Improving Alkaline Peroxide Delignification Using a Vandium Activator", Paprican and Department of Chemistry, McGill University, Montreal, Quebec, Oct. 25-29, 1998 (15 pages).

Swern, Daniel (ed.), "Organic Peroxides", Wiley-Interscience, New York (1970), vol. 1, pp. 360-369.

"Tsunokawa, Youko et al., "A Versatile Method for Preparation of 0-AikylperoxycarbonicAcids: Epoxidation with Alkyloxycarbonylimidazoles and Hydrogen Peroxide", Tetrahedron Letters, vol. 23, No. 20, (1982), pp. 2113-2116."

United States Patent and Trademark Office, "Office Action", issued in connection with U.S. Appl. No. 13/844,515, 11 pages, mailed on Dec. 5, 2014.
CN1020197C—Monsanto Co—English Translation.
CN1231599—Procter & Gamble—English Translation.
CN102105443—Ecolab Inc.—English Translation.
JP2000505136—English Translation.
JP2002105352—Ricoh KK—English Translation.
JP2007084589—Nippon Peroxide Co Ltd—English Translation.
JP2007520479—English Translation.
JP2007523892—English Translation.
JP2009500415—English Translation.
JP2011518775—English Translation.
JP2012126740—Ecolab Inc.—English Translation.
JP2012126741—Ecolab Inc.—English Translation.
JP2012126918—Ecolab Inc.—English Translation.
JP2012149080—Ecolab Inc—English Translation.
JPH01297499—Akzo NV—English Translation.
JPH05503507—English Translation.
JPH05507951—English Translation.
JPH06100531—Unilever NV—English Translation.
JPH06503372—English Translation.
JPH06510526—Ekorabu Inc.—English Translation.
JPH09512042—English Translation.
JPS59206495—Lion Corp—English Translation.
JPS63165364—Monsanto Co.—English Translation.
CN 100486668C, San Nopco—English Translation.
CN 1751768—San Nopco—English Translation.
DE 197 54 290 A1—Henkel KGaA—English Translation.
EP 0 061 393—Elf Atochem—English Abstract.
EP 0 280 697—Garcin Francoise—English Translation.
EP 0 395 902—Schulke & Mayr Gmbh—English Translation.
EP 0 626 371 B1—Degussa—English Translation.
EP 2 271 410—Arkema—English Translation.
JP 2006-45146—Kao Corp—English Translation.
JP 2006-45147—Kao Corp—English Translation.

State Intellectual Property Office, "First Office Action", issued in connection with Chinese Application No. 201380014182.1, mailed Jun. 18, 2015, 26 pages.

IP Australia, "Patent Examination Report No. 1," issued in connection with Australian Patent Application No. 2012201802, mailed on Mar. 5, 2013. 3 pages.

IP Australia, "Patent Examination Report No. 1 and No. 2," issued in connection with Australian Patent Application No. 2012201800, mailed on Jul. 3, 2013. 6 pages.

IP Australia, "Patent Examination Report No. 1 and No. 2," issued in connection with Australian Patent Application No. 2012201801, mailed on Jul. 1, 2013. 6 pages.

IP Australia, "Patent Examination Report No. 1 and No. 2," issued in connection with Australian Patent Application No. 2012201804, mailed on Jul. 1, 2013. 6 pages.

IP Australia, "Patent Examination Report No. 1 and No. 2," issued in connection with Australian Patent Application No. 2009230713 mailed on Jul. 1, 2013. 6 pages.

* cited by examiner

DETERGENTS CAPABLE OF CLEANING, BLEACHING, SANITIZING AND/OR DISINFECTING TEXTILES INCLUDING SULFOPEROXYCARBOXYLIC ACIDS

CROSS REFERENCE TO RELATED APPLICATIONS

This application is a continuation of U.S. patent application Ser. No. 13/221,613 filed Aug. 30, 2011, which is a continuation in part of U.S. patent application Ser. No. 12/413,189, filed on Mar. 27, 2009, now U.S. Pat. No. 8,344,026, which claims priority to U.S. Provisional Application Ser. No. 61/040,444, filed on Mar. 28, 2008 and entitled "SULFOPEROXYCARBOXYLIC ACIDS, THEIR PREPARATION AND METHODS OF USE AS BLEACHING AND ANTIMICROBIAL AGENTS." The entire contents of these earlier-filed patent applications are hereby expressly incorporated herein by reference including, without limitation, each of the specification, claims, and abstract, as well as any figures, tables, or drawings thereof.

FIELD OF THE INVENTION

The present invention relates to detergents, e.g., laundry detergents, incorporating sulfoperoxycarboxylic acid compounds.

BACKGROUND

Peroxycarboxylic acids are known for use as antimicrobials (inhibition, sanitizing, disinfecting, and sterilizing) and bleaching agents. However, conventional peroxycarboxylic acids have inherent disadvantages of limited storage stability and water solubility. Further, most peroxycarboxylic acids have an unpleasant odor. Thus, a need exists for storage stable, low or no odor, water soluble peroxycarboxylic acid compounds and compositions that also possess cleaning and detergency, antimicrobial (inhibition, sanitizing, disinfecting, and sterilizing) and bleaching properties.

SUMMARY

In some aspects, the present invention relates to novel sulfoperoxycarboxylic acids, and methods for making them. The compounds of the invention are storage stable, have low or no-odor, and are water soluble. Further, the compounds of the present invention can be derived from non-petroleum based, renewable oils.

In some aspects, the present invention provides methods for using the compounds of the present invention as detergents, bleaching and/or antimicrobial agents. In some aspects, the present invention provides methods for using the compounds of the invention as antimicrobial agents that can inhibit or sanitize or disinfect or sterilize woven or non-woven textile fabrics. In some aspects, the present invention provides methods for using the compounds of the invention as coupling agents. In some aspects, the present invention provides methods for using the compounds of the present invention as woven or non-woven textile laundering detergents. In yet some other aspects, the present invention provides methods for low foaming bleach hydrotropes and detergents for laundering woven or non-woven textile fabrics in commercially available wash systems used in the consumer or industrial or institutional market places; including, but not limited to, continuous or batch: tunnel washers, washer extractors, textile-presoak wash systems, and for top or side loading washing machines. In yet some additional aspects, the present invention provides for using compounds of the present invention for multi-utility wash machines that can presoak, wash, extract, dry, or any combination thereof.

In some embodiments, the compounds and compositions of the present invention are suitable for use as low temperature bleaches, e.g., at about 40 degrees Celsius. In some embodiments, the compounds of the present invention are suitable for use as pH optimized peroxygen bleaches, in combination with alkaline detergents. In some embodiments, the present invention includes a method for using the compounds and compositions of the present invention as color safe, textile tolerant bleaches for textiles, e.g., wools and cotton.

In some embodiments, the novel sulfoperoxycarboxylic acids are provided in a composition including about 0.05 wt % to about 50 wt % of the novel sulfoperoxycarboxylic acid compound; about 0.1 wt % to about 75 wt % of an oxidizing agent; about 0.1 wt % to about 40 wt % of a $C_1$-$C_{22}$ carboxylic acid in combination with one $C_1$ to $C_{22}$ peroxycarboxylic acid; about 0.50 wt % to about 70 wt % of a surfactant; about 0.0 wt % to about 5 wt % of an acid; and about 0.0 to about 10 wt % of a viscosity reducer.

DETAILED DESCRIPTION

Figure 1:
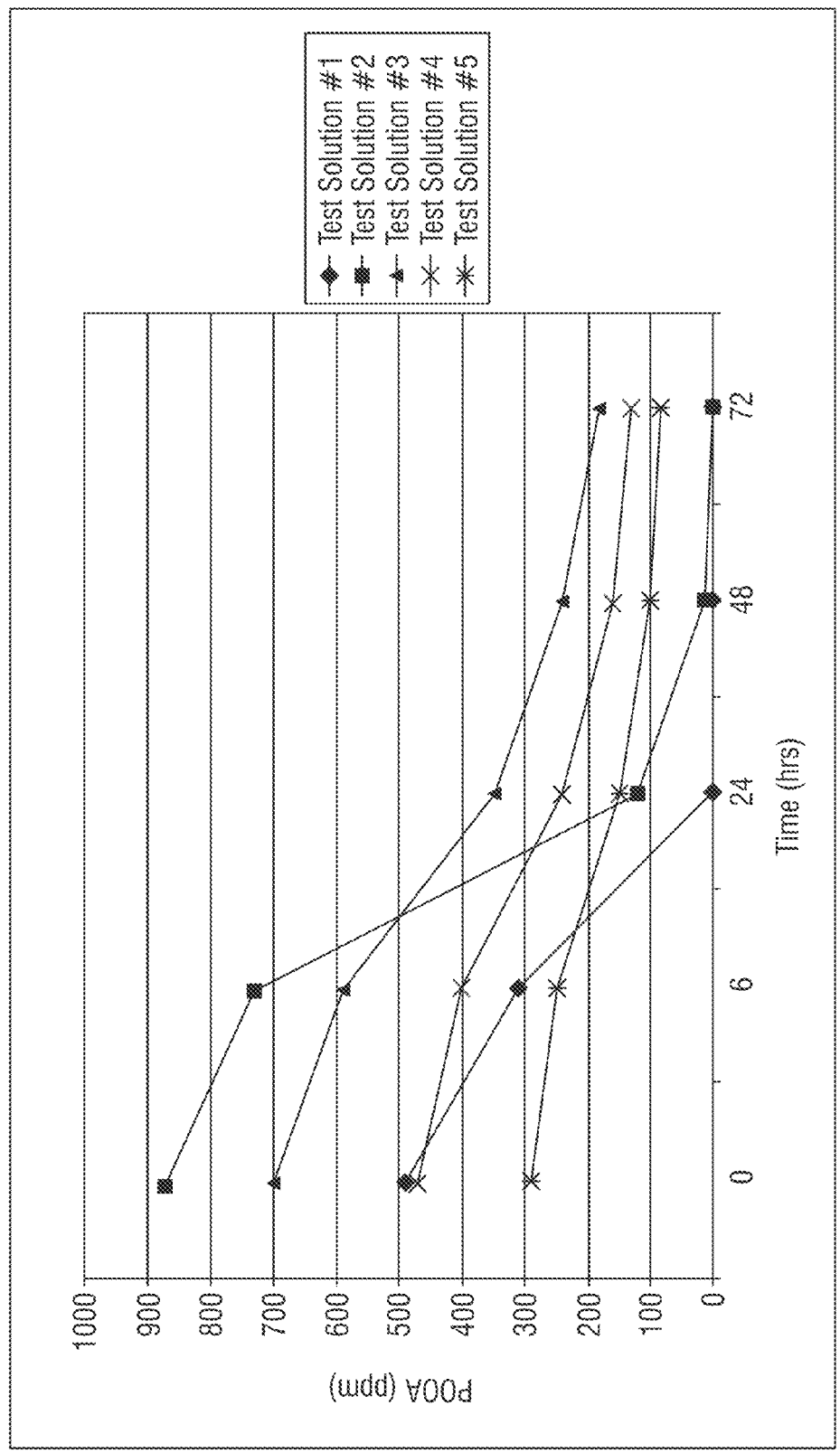
FIG. 1 is a graphical depiction of the stability profile of peroxyoctanoic acid over time when contacted with different test solutions.

The present invention relates to sulfoperoxycarboxylic acids of Formula I, and methods of making and using them. In some embodiments, the sulfoperoxycarboxylic acids of the invention are not sulfonated at the terminal position of the carboxylic acid chain. Unlike conventional peroxycarboxylic acids, it has been found that the sulfoperoxycarboxylic acids of the present invention are low-odor, water soluble, and storage stable. The compounds of the present invention can be used as a pure solid powder, or blended with additional functional ingredients, for example, chelators, buffers, or other cleaning agents. They can also be incorporated into liquid, solid, or gel formulas. The compounds and compositions of the present invention have many uses including, but not limited to, detergents, antimicrobials, bleaches, and coupling agents.

So that the invention maybe more readily understood, certain terms are first defined.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions or different reaction levels for a composition resulting from a particular initial mixture. Whether or not modified by the term "about", the claims include equivalents to the quantities.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

As used herein, the phrases "objectionable odor," "offensive odor," or "malodor," refer to a sharp, pungent, or acrid odor or atmospheric environment from which a typical person withdraws if they are able to. Hedonic tone provides a measure of the degree to which an odor is pleasant or unpleasant. An "objectionable odor," "offensive odor," or "malodor" has an hedonic tone rating it as unpleasant as or more unpleasant than a solution of 5 wt-% acetic acid, propionic acid, butyric acid, or mixtures thereof.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant" or "plant product" includes any plant substance or plant-derived substance. Plant products include, but are not limited to, seeds, nuts, nut meats, cut flowers, plants or crops grown or stored in a greenhouse, house plants, and the like. Plant products include many animal feeds.

As used herein, the phrase "meat product" refers to all forms of animal flesh, including the carcass, muscle, fat, organs, skin, bones and body fluids and like components that form the animal. Animal flesh includes, but is not limited to, the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET).

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc., or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a composition according to the present invention.

As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthroscopes) and related equipment, and the like, or combinations thereof.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, a "laundry machine" refers to any device for laundering woven or non-woven textile fabrics in commercially available or experimental wash systems used in the consumer and/or industrial and/or institutional markets; including, but not limited to, continuous washers (e.g., tunnel type continuous batch washers), batch washer extractors, textile-presoak wash systems, steam systems, dry-wash devices and other dry cleaning devices, and/or top or side loading washing machines (e.g., those used in the residential or small institutional markets). This includes laundering systems that are multi-utility wash machines, e.g., those that can presoak, wash, extract, steam, dry, or any combination thereof. A typical laundry facility may consist of multiple single washing machines or continuous load washers (e.g., tunnel washers), or a combination thereof.

As used herein, a "textile" is any woven or non-woven fabric or article, or garment including, but not limited to, all types found in the consumer, industrial, and/or institutional markets including, but not limited to, those made of cotton, poly-cotton blends, wool, aramids, polyurethanes, olefins, polyactids, nylons, silk, hemp, rayon, flax, jute, acrylics, polyesters, those made from many other synthetic or natural fibers and mixtures thereof.

As used herein, the term "phosphorus-free" or "substantially phosphorus-free" refers to a composition, mixture, or ingredient that does not contain phosphorus or a phosphorus-containing compound or to which phosphorus or a phosphorus-containing compound has not been added. Should phosphorus or a phosphorus-containing compound be present through contamination of a phosphorus-free composition, mixture, or ingredients, the amount of phosphorus shall be less than 0.5 wt %. More preferably, the amount of phosphorus is less than 0.1 wt %, and most preferably the amount of phosphorus is less than 0.01 wt %.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "caustic free" or "alkali caustic free" or "substantially caustic" or "substantially alkali caustic free" refers to a composition, mixture, or ingredient that does not contain significant residual and titrate-able carbonate alkalinity from alkali metal hydroxides such as sodium hydroxide or potassium hydroxide, or does not contain an alkali metal hydroxide-containing compound or to which alkali metal hydroxide-containing compound has not been added. The pH of such compositions or mixtures may be below a pH of about 9.0, below a pH of about 8.0 or below a pH of about 7.0. Should an alkali metal hydroxide-containing compound be present through contamination of an alkali metal hydroxide-free composition, mixture, or ingredients, the amount of alkali metal hydroxide or caustic component shall be less than about 0.5 wt %, or less than about 0.2 wt %.

In some embodiments, an alkali metal hydroxide may be used in the composition, mixture, or ingredients for neutralization, stabilization, or pH adjustment purposes. If an alkali metal hydroxide is included for such a purpose, the amount of alkali metal hydroxide or caustic component shall be less than about 10.0 wt %, than about 5.0 wt %, or than about 2.0 wt %.

As used herein, the terms "chelating agent" and "sequestrant" refer to a compound that forms a complex (soluble or not) with water hardness ions (from the wash water, soil and substrates being washed) in a specific molar ratio. Chelating agents that can form a water soluble complex include sodium tripolyphosphate, ethylenediaminetetraacetic acid (EDTA), diethylene triamine pentaacetic acid (DTPA), nitrilotriacetic acid (NTA), citrate, and the like. Sequestrants that can form an insoluble complex include sodium triphosphate, zeolite A, and the like. As used herein, the terms "chelating agent" and "sequestrant" are synonymous.

As used herein, the term "free of chelating agent" refers to a composition, mixture, or ingredients that do not contain a chelating agent or sequestrant or to which a chelating agent or sequestrant has not been added. Should a chelating agent or sequestrant be present through contamination of a composition, mixture, or ingredient that is free of chelating agent, the amount of a chelating agent or sequestrant shall be less than 2 wt-%. In another embodiment, such an amount of a chelating agent or sequestrant is less than 1 wt-%. In other embodiments, such an amount of a chelating agent or sequestrant is less than 0.5 wt-% and in yet other embodiments, such an amount of a chelating agent or sequestrant is less than 0.1 wt-%.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills Mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. or within 60 seconds at 50° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C. or within 60 seconds at 50° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbiostatic. A sanitizer and a disinfectant are, by definition, agents which provide antimicrobial or microbiocidal activity. In contrast, a preservative is generally described as an inhibitor or microbiostatic composition As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including hetero aromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

As used herein the term, "consisting essentially of" in reference to a composition refers to the listed ingredients and does not include additional ingredients that, if present, would affect the cleaning, disinfecting or sterilizing ability of the composition. The term "consisting essentially of" may also refer to a component of the composition. For instance, a surfactant package may consist essentially of two or more surfactants and such surfactant package would not include any other ingredients that would affect the effectiveness of that surfactant package—either positively or negatively. As used herein the term "consisting essentially of" in reference to a method of cleaning refers to the listed steps and does not include additional steps (or ingredients if a composition is included in the method) that, if present, would affect the cleaning ability of the cleaning method.

The present invention contemplates the possibility of omitting any components listed herein. The present invention further contemplates the omission of any components even though they are not expressly named as included or excluded from the invention.

Compounds of the Invention

The present invention relates, at least in part, to sulfoperoxycarboxylic acids, compositions thereof, and the use thereof in a variety of bleaching, disinfecting and cleaning applications. The sulfoperoxycarboxylic acids of the present invention are also useful as coupling agents. Further, certain compounds of the present invention can be derived from non-petroleum based, renewable oils, e.g., castor, toll, soybean, canola, olive, peanut, tallow, rapeseed, and palm oils.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

Without wishing to be bound by any particular theory, it is thought that mid-chain sulfonated peracids, e.g., mid-chain sulfonated peracids with a C10-C18 carbon backbone have a substantially greater solubility compared to terminally sulfonated peracids of a similar chain length, even at an acidic pH. For example, at a pH of 4, the terminally sulfonated peracid, 11-sulfoundecane peroxoic acid has a relatively low solubility of about 1.3%. At the same pH, the mid chain sulfonated peracid, persulfonated oleic acid has a solubility of greater than about 50%. This is unexpected as an increase in peracid chain length is thought to lead to a decrease in solubility. The issue of low solubility when using long chain peracids has been addressed by increasing the pH to above 7. However, at increased pH antimicrobial efficacy is substantially reduced. Further, bleaching efficacy decreases proportionally with every pH unit increase over about 7. Thus, solubility at an acidic pH (lower than about 7) is beneficial to the mid-chain sulfonated peracids of the present invention.

The sulfoperoxycarboxylic acids of the present invention can be used alone, or can be combined with additional ingredients. In some embodiments, compositions of the present invention can include one or more of the sulfoperoxycarboxylic acids of the present invention.

Peroxycarboxylic (or percarboxylic) acids generally have the formula $R(CO_3H)_n$, where, for example, R is an alkyl, arylalkyl, cycloalkyl, aromatic, or heterocyclic group, and n is one, two, or three, and named by prefixing the parent acid with peroxy. Percarboxylic acids can be made by the direct, acid catalyzed equilibrium action of hydrogen peroxide with the carboxylic acid, by autooxidation of aldehydes, or from acid chlorides, and hydrides, or carboxylic anhydrides with hydrogen or sodium peroxide. The R group can be saturated or unsaturated as well as substituted or unsubstituted.

The chemical structures herein are drawn according to the conventional standards known in the art. Thus, where an atom, such as a carbon atom, as drawn appears to have an unsatisfied valency, then that valency is assumed to be satisfied by a hydrogen atom, even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center may be of either (R)- or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present invention may exist in unsolvated as well as solvated forms with acceptable solvents such as water, THF, ethanol, and the like. In general, the solvated forms are considered equivalent to the unsolvated forms for the purposes of the present invention.

In some aspects, the present invention pertains to sulfoperoxycarboxylic acids of Formula I:

(Formula I)

$$R_1-CH-R_2-COOOH$$
$$\phantom{R_1-CH-}|$$
$$\phantom{R_1-C}SO_3^-X^+$$

wherein $R_1$ is hydrogen, or a substituted or unsubstituted alkyl group;

$R_2$ is a substituted or unsubstituted alkyl group;

X is hydrogen, a cationic group, or an ester forming moiety;

or salts or esters thereof.

In some embodiments, $R_1$ is a substituted or unsubstituted $C_m$ alkyl group; X is hydrogen a cationic group, or an ester forming moiety; $R_2$ is a substituted or unsubstituted $C_n$ alkyl group; m=1 to 10; n=1 to 10; and m+n is less than 18, or salts, esters or mixtures thereof.

In some embodiments, $R_1$ is hydrogen. In other embodiments, $R_1$ is a substituted or unsubstituted alkyl group. In some embodiments, $R_1$ is a substituted or unsubstituted alkyl group that does not include a cyclic alkyl group. In some embodiments, $R_1$ is a substituted alkyl group. In some embodiments, $R_1$ is an unsubstituted $C_1$-$C_9$ alkyl group. In some embodiments, $R_1$ is an unsubstituted $C_7$ or $C_8$ alkyl. In other embodiments, $R_1$ is a substituted $C_8$-$C_{10}$ alkyl group. In some embodiments, $R_1$ is a substituted $C_8$-$C_{10}$ alkyl group is substituted with at least 1, or at least 2 hydroxyl groups. In still yet other embodiments, $R_1$ is a substituted $C_1$-$C_9$ alkyl group. In some embodiments, $R_1$ is a substituted $C_1$-$C_9$ substituted alkyl group is substituted with at least 1 $SO_3H$ group.

In other embodiments, $R_1$ is a $C_9$-$C_{10}$ substituted alkyl group. In some embodiments, $R_1$ is a substituted $C_9$-$C_{10}$ alkyl group wherein at least two of the carbons on the carbon backbone form a heterocyclic group. In some embodiments, the heterocyclic group is an epoxide group.

In some embodiments, $R_2$ is a substituted $C_1$ to $C_{10}$ alkyl group. In some embodiments, $R_2$ is a substituted $C_8$-$C_{10}$ alkyl. In some embodiments, $R_2$ is an unsubstituted $C_6$-$C_9$ alkyl. In other embodiments, $R_2$ is a $C_8$ to $C_{10}$ alkyl group substituted with at least one hydroxyl group. In some embodiments, $R_2$ is a $C_{10}$ alkyl group substituted with at least two hydroxyl groups. In other embodiments, $R_2$ is a $C_8$ alkyl group substituted with at least one $SO_3H$ group. In some embodiments, $R_2$ is a substituted $C_9$ group, wherein at least two of the carbons on the carbon backbone form a heterocyclic group. In some embodiments, the heterocyclic group is an epoxide group. In some embodiments, $R_1$ is a $C_8$-$C_9$ substituted or unsubstituted alkyl, and $R_2$ is a $C_7$-$C_8$ substituted or unsubstituted alkyl.

In some embodiments, the compound of the invention is selected from the group consisting of:

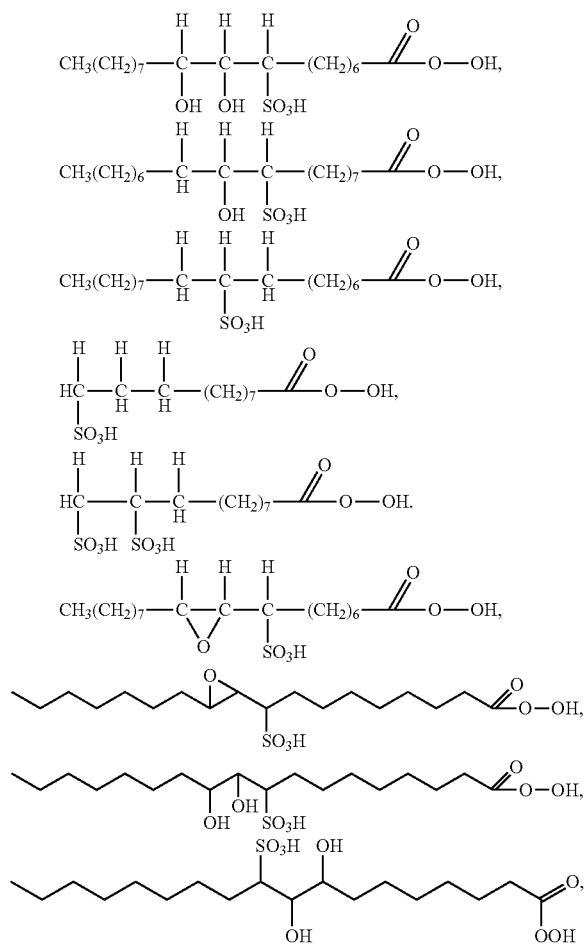

salts, esters, and mixtures and derivatives thereof.

In other embodiments, the compound of the invention is selected from the group consisting of:

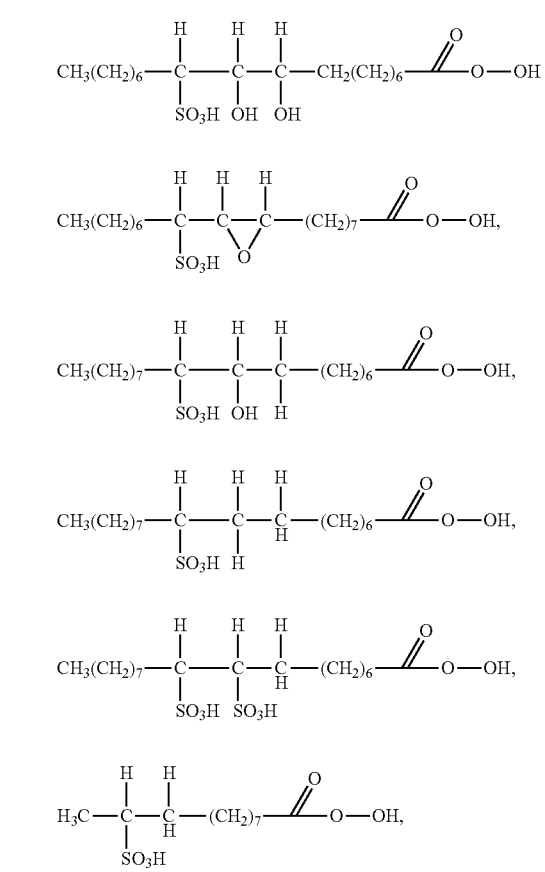

and mixtures and derivatives thereof.

Compounds of the invention are also shown in Table 1 below.

TABLE 1

| Sulfonated Peroxyacid Compounds | |
|---|---|
| ID | Structure/Name of Compound |
| A | 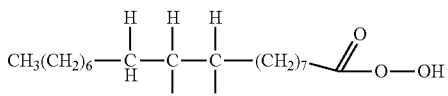
10-Hydroxy-9-sulfooctadecaneperoxoic acid |
| B | 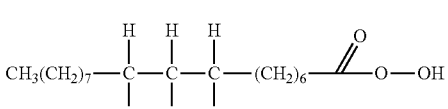
9,10-Dihydroxy-8-sulfooctadecaneperoxoic acid |
| C | 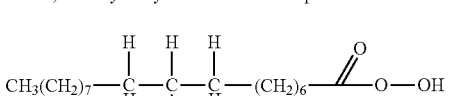
9-Sulfooctadecaneperoxoic acid |

TABLE 1-continued

Sulfonated Peroxyacid Compounds

| ID | Structure/Name of Compound |
|---|---|
| D | 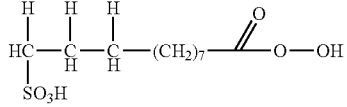<br>11-Sulfoundecaneperoxoic acid |
| E | 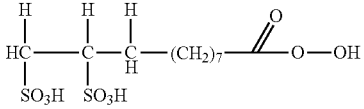<br>10,11-Disulfoundecaneperoxoic acid |
| F | 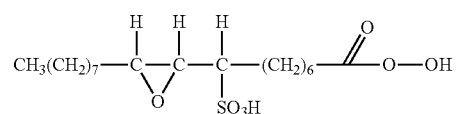<br>8-(3-octyloxiran-2-yl)-8-sulfooctaneperoxoic acid |
| G | 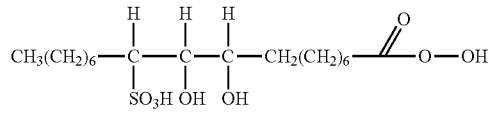<br>9,10-Dihydroxy-11-sulfooctadecaneperoxoic acid |
| H | 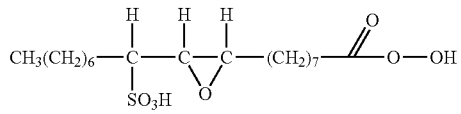<br>8-(3-octyloxiran-2-yl)-8-sulfooctaneperoxoic acid |
| I | 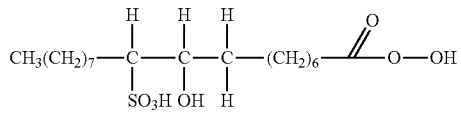<br>9-Hydroxy-10-sulfooctadecaneperoxoic acid |
| J | 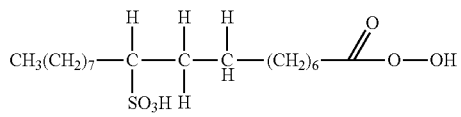<br>10-Sulfooctadecaneperoxoic acid |
| K | 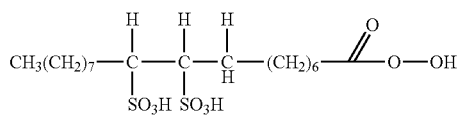<br>9,10-Disulfooctadecaneperoxoic acid |
| L | 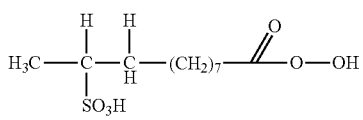<br>10-Sulfoundecaneperoxoic acid |

TABLE 1-continued

Sulfonated Peroxyacid Compounds

| ID | Structure/Name of Compound |
|---|---|
| M | 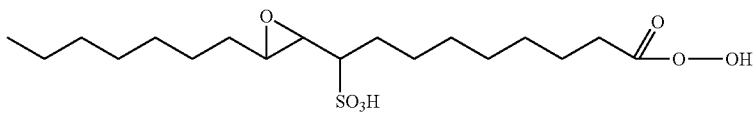<br>9-(3-(heptyloxiran-2-yl)-9-sulfononaneperoxoic acid |
| N | 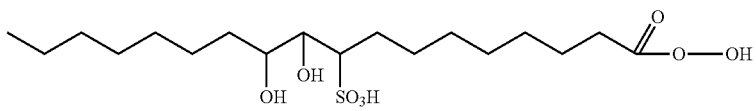<br>10,11-dihydroxy-9-sulfooctadecaneperoxoic acid |
| O | 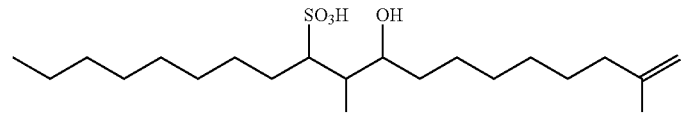<br>8,9-dihydroxy-10-sulfooctadecaneperoxoic acid |

In some embodiments, the starting material for the preparation of the compounds of the present invention is a sulfonated fatty acid. Without wishing to be bound by any particular theory, it is thought that the sulfo-group is inert in an oxidative environment. Further, it is thought that the hydrophility of the sulfo-group is not as impacted by pH as other substituents. In some embodiments, the sulfonated percarboxylic acids of the present invention are formed from commercially available sulfonated fatty acids. In other embodiments, the compounds of the present invention are formed from commercially available non-sulfonated fatty acids, which can be sulfonated. In some embodiments, the starting fatty acid will be sulfonated prior to conversion to a peroxycarboxylic acid. In other embodiments, the starting fatty acid will be sulfonated at the same time or after the formation of the peroxycarboxylic acid. Sulfonated fatty acids suitable for use in forming compounds of the present invention include, but are not limited to, 11-sulfoundecanoic acid, 10,11-disulfoundecanoic acid, sulfonated oleic acid, sulfonated linoleic acid, sulfonated palmitoleic acid and sulfonated stearic acid.

Without wishing to be bound by any particular theory, it is thought that the peracid formed from certain commercially available sulfonated oleic acid starting materials includes a mixture of the compounds of the present invention. It is thought that this is due, in part, to the nature of the sulfonated oleic acid starting material. That is, it is thought that because the sulfonated oleic acid starting material is derived from naturally occurring sources, it is not chemically pure, i.e., does not contain only one form of the sulfonated oleic acid. Thus, without wishing to be bound by any particular theory it is thought that sulfonated peroleic acid formed (hereinafter referred to as the "sulfonated peroleic acid product") can include a mixture of Compounds A, N, I, and O as the primary components. Without wishing to be bound by any particular theory it is thought that in some embodiments, the sulfonated peroleic acid product includes about 20-25 wt % Compound A (10-Hydroxy-9-sulfooctadecaneperoxoic acid) about 20-25 wt % Compound N (10,11-dihydroxy-9-sulfooctadecaneperoxoic acid), about 20-25 wt % Compound I (9-Hydroxy-10-sulfooctadecaneperoxoic acid), and about 20-25 wt % Compound O (8,9-dihydroxy-10-sulfooctadecaneperoxoic acid). The remainder of the product is thought to include about 5 to about 10 wt % of a mixture of these compounds.

The sulfoperoxyacids can be formed using a variety of reaction mechanisms. For example, in some embodiments, the peracids are formed by the direct acid catalyzed equilibrium action of hydrogen peroxide with the starting materials.

In some embodiments, the sulfonated carboxylic acids for use in forming the compounds of the present invention are not sulfonated at the α position. As used herein, the term "α position" refers to the carbon on the carbon backbone of the percarboxylic acid chain that is directly connected to, viz. immediately next to, the carboxylic acid group. It has been found that having the sulfonate group at the α position of the fatty acid prohibits the oxidation and/or perhydrolysis of the carboxylic acid group to form the corresponding peroxycarboxylic acid. Without wishing to be bound by any particular theory, it is thought that the α-sulfo group makes the carboxylic acid group on the fatty acid electronically deficient, and thus oxidation and/or perhydrolysis and formation of the corresponding percarboxylic acid requires extremely low pHs. Upon neutralization or even moderate elevation of these pHs, it is thought that the peracids very rapidly hydrolyze back to the parent acids, rendering them impractical for most applications.

Sulfonated Peroxycarboxylic Acid Compositions

In some aspects, the present invention relates to compositions including a sulfonated peroxycarboxylic acid compound, or mixture thereof, of Formula I. The compositions of the present invention can be used as detergent and/or bleaching compositions for a variety of substrates and surfaces, e.g., woven or non-woven textiles, hard surfaces. The compositions of the present invention can also be used as sanitizing or disinfectant or sterilizing or sporicidal or for other antimicrobial purposes. Further, compounds of the present invention can be used as coupling agents in compositions for various applications, e.g., food contact sanitizing, hard surface disinfection, textile disinfection. In some embodiments, compositions containing compounds of the present invention can be multipurpose. That is, the compositions of the present invention can, for example, act as multipurpose combination systems; including, antimicrobials and detergents and bleaches, or as both coupling agents and antimicrobials and bleaches, and detergent and bleaching mixtures, and the like.

The compositions of the present invention also show enhanced stability compared to conventional peroxygen containing compositions. In some embodiments, the compositions of the present invention are stable for at least about 1 year at room temperature. In some embodiments, the compositions of the present invention are stable at about 100° F. for at least 30 days. In other embodiments, the compositions of the present invention are stable at about 140° F. for at least 30 days. For example, 11-sulfoundecanoic peroxyacid (Compound D) is stable as a powder system at about 140° F. for at least 30 days.

The compositions of the present invention have no or low odor. For example, in some embodiments, compositions of the present invention have an odor less unpleasant than (e.g., as measured by an hedonic tone rating) than 5, 4, 3, 2, or 1 wt-% acetic acid in water. In other embodiments, the compositions of the present invention have no odor detectable by a user.

In some embodiments, the compositions of the present invention include a sulfonated peracid or mixture thereof of Formula I, and at least one additional ingredient. Additional ingredients suitable for use with the compositions of the present invention include, but are not limited to, oxidizing agents, carboxylic acids, surfactants, stabilizing agents (e.g., metal chelators), and mixtures thereof. The compounds and compositions of the invention can also be used in conjunction with conventional cleaning agents, e.g., alkaline detergents.

In some embodiments, the compositions of the present invention can be used as a sanitizing composition for articles cleaned using a clean in place (CIP) technique. Such compositions can include an oxidizing agent, a stabilizing agent, an acidulant and a surfactant or mixture thereof, in the following concentrations.

TABLE A

| Concentrate CIP Sanitizer by Weight % | | | |
|---|---|---|---|
| Oxidizing Agent | 0.1-10 | 2-8 | 5-7 |
| Stabilizing Agent | 0.1-10 | 0.5-5 | 1-2 |
| Acidulant | 0-50 | 10-40 | 20-30 |
| Surfactant | 0-50 | 10-40 | 25-35 |

In other embodiments, the compositions of the present invention can be used as a textile disinfectant/sanitizer. Such compositions can include oxidizing agent, stabilizing agent and a carboxylic acid in the following concentrations.

TABLE B

| Concentrate Textile Disinfectant/Sanitizer by Weight % | | | |
|---|---|---|---|
| Oxidizing Agent | 10-75 | 25-60 | 30-50 |
| Stabilizing Agent | 0.1-10 | 0.5-5 | 2-4 |
| Carboxylic Acid | 1-40 | 10-30 | 20-25 |

In other embodiments, the compositions of the present invention can be used as a textile combined cleaning, bleaching, and disinfectant. Such compositions can include oxidizing agent, stabilizing agent, carboxylic acid, surfactant, bleach, acidulant, and viscosity reducing agent in the following concentrations.

TABLE C

| Concentrate Textile Detergent/Bleach/Disinfectant by Weight % | | | |
|---|---|---|---|
| Oxidizing Agent | 0.1-75 | 2-40 | 5-30 |
| Stabilizing Agent | 0.01-10 | 0.05-5 | 0.08-2 |
| Bleach | 0.05-75 | 0.10-30 | 1.0-20 |
| Carboxylic Acid | 0.1-40 | 0.5-30 | 1-20 |
| Surfactant | 0.5-70 | 2-50 | 10-35 |
| Viscosity Reducing Agent | 0-20 | 0.5-15 | 1-10 |

Oxidizing Agents

In some aspects, the compositions of the present invention include a compound of Formula I. In some embodiments, the compositions of the present invention further include at least one oxidizing agent. In some embodiments, the compositions of the present invention are substantially free of an oxidizing agent. When present, the present composition can include any of a variety of oxidizing agents, for example, hydrogen peroxide and/or any inorganic or organic peroxide or peracid. The oxidizing agent can be present at an amount effective to convert a sulfonated carboxylic acid to a sulfonated peroxycarboxylic acid. In some embodiments, the oxidizing agent can also have antimicrobial activity. In other embodiments, the oxidizing agent is present in an amount insufficient to exhibit antimicrobial activity.

In some embodiments, the compositions of the present invention include about 0.001 wt % oxidizing agent to about 99 wt % oxidizing agent. In other embodiments, the compositions of the present invention include about 1 wt % to about 60 wt % oxidizing agent. In some embodiments, the compositions of the invention include about 50 wt % to about 80 wt % oxidizing agent. In other embodiments, the compositions of the invention include about 15 wt % to about 30 wt % oxidizing agent. In yet other embodiments, the compositions of the present invention include about 25 wt % oxidizing agent. It is to be understood that all ranges and values between these ranges and values are encompassed by the present invention.

Examples of inorganic oxidizing agents include the following types of compounds or sources of these compounds, or alkali metal salts including these types of compounds, or forming an adduct therewith: hydrogen peroxide, urea-hydrogen peroxide complexes or hydrogen peroxide donors of: group 1 (IA) oxidizing agents, for example lithium peroxide, sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2)_2(OH)_4] \cdot 6H_2O$ (also called sodium perborate tetrahydrate); sodium peroxyborate tetrahydrate of the formula $Na_2B_2(O_2)_2[(OH)_4] \cdot 4H_2O$ (also called sodium perborate trihydrate); sodium peroxyborate of the formula $Na_2[B_2(O_2)_2(OH)_4]$ (also called sodium perborate monohydrate); group 14 (IVA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group VIIa oxidizing agents such as sodium periodate, potassium perchlorate. Other active inorganic oxygen compounds can include transition metal peroxides; and other such peroxygen compounds, and mixtures thereof.

Examples of organic oxidizing agents include, but are not limited to, perbenzoic acid, derivatives of perbenzoic acid, t-butyl benzoyl hydroperoxide, benzoyl hydroperoxide, or any other organic based peroxide and mixtures thereof, as well as sources of these compounds. Other examples include, but are not limited to, peracids including C1-C12 percarboxylic acids such as peracetic acid, performic acid, percarbonic acid, peroctanoic acid, and the like; per-diacids or per-triacids such as peroxalic acid, persuccinic acid, percitric acid, perglycolic acid, permalic acid and the like; and aromatic peracids such as perbenzoic acid, or mixtures thereof.

In some embodiments, the compositions of the present invention employ one or more of the inorganic oxidizing agents listed above. Suitable inorganic oxidizing agents include ozone, hydrogen peroxide, hydrogen peroxide adduct, group IIIA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

Carboxylic and Percarboxylic Acids

In some embodiments, the compositions of the present invention include at least one sulfoperoxycarboxylic acid of the present invention, and at least one carboxylic and/or percarboxylic acid. In some embodiments, the compositions of the present invention include at least two, at least three, or at least four or more carboxylic and/or percarboxylic acids.

In some embodiments, the carboxylic acid for use with the compositions of the present invention includes a $C_1$ to $C_{22}$ carboxylic acid. In some embodiments, the carboxylic acid for use with the compositions of the present invention is a $C_5$ to $C_{11}$ carboxylic acid. In some embodiments, the carboxylic acid for use with the compositions of the present invention is a $C_1$ to $C_4$ carboxylic acid. Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof.

In some embodiments, the compositions of the present invention include about 0.1 wt % to about 80 wt % of a carboxylic acid. In other embodiments, the compositions of the present invention include about 1 wt % to about 60 wt % of a carboxylic acid. In yet other embodiments, the compositions of the present invention include about 20 wt %, about 30 wt %, or about 40 wt % of a carboxylic acid. In some embodiments, the compositions of the present invention include about 5 wt % to about 10 wt % of acetic acid. In other embodiments, the compositions of the present invention include about 5 wt % to about 10 wt % of octanoic acid. In other embodiments, the compositions of the present invention include a combination of octanoic acid and acetic acid.

In some embodiments, the compositions of the present invention include a compound of Formula I, and at least one peroxycarboxylic acid. Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, or the peroxyacids of their branched chain isomers, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof. In some embodiments, the compositions of the invention utilize a combination of several different peroxycarboxylic acids. For example, in some embodiments, the composition includes one or more $C_1$ to $C_4$ peroxycarboxylic acids and one or more $C_5$ to $C_{11}$ peroxycarboxylic acids. In some embodiments, the $C_1$ to $C_4$ peroxycarboxylic acid is peroxyacetic acid and the $C_5$ to $C_{11}$ acid is peroxyoctanoic acid.

In some embodiments, the compositions of the present invention include peroxyacetic acid. Peroxyacetic (or peracetic) acid is a peroxycarboxylic acid having the formula: $CH_3COOOH$. Generally, peroxyacetic acid is a liquid having an acrid odor at higher concentrations and is freely soluble in water, alcohol, ether, and sulfuric acid. Peroxyacetic acid can be prepared through any number of methods known to those of skill in the art including preparation from acetaldehyde and oxygen in the presence of cobalt acetate. A solution of peroxyacetic acid can be obtained by combining acetic acid with hydrogen peroxide. A 50% solution of peroxyacetic acid can be obtained by combining acetic anhydride, hydrogen peroxide and sulfuric acid.

In some embodiments, the compositions of the present invention include peroxyoctanoic acid, peroxynonanoic acid, or peroxyheptanoic acid In some embodiments, the compositions include peroxyoctanoic acid. Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid can be prepared through any number of methods known to those of skill in the art. A solution of peroxyoctanoic acid can be obtained by combining octanoic acid and hydrogen peroxide and a hydrotrope, solvent or carrier.

In some embodiments, the compositions of the present invention include about 0.1 wt % to about 90 wt % of one or more peroxycarboxylic acids. In other embodiments, the compositions of the present invention include about 1 wt % to about 25 wt % of one or more peroxycarboxylic acids. In yet other embodiments, the compositions of the present invention include about 5 wt % to about 10 wt % of one or more peroxycarboxylic acids. In some embodiments, the compositions of the present invention include about 1 wt % to about 25 wt % of peroxyacetic acid. In other embodiments, the compositions of the present invention include about 0.1 wt % to about 10 wt % of peroxyoctanoic acid. In still yet other embodiments, the compositions of the present invention include a mixture of about 5 wt % peroxyacetic acid, and about 1.5 wt % peroxyoctanoic acid.

Surfactants

In some embodiments, the compositions of the present invention include a surfactant. Surfactants suitable for use with the compositions of the present invention include, but are not limited to, nonionic surfactants, anionic surfactants, and zwitterionic surfactants. In some embodiments, the compositions of the present invention include about 10 wt % to about 50 wt % of a surfactant. In other embodiments the compositions of the present invention include about 15 wt % to about 30% of a surfactant. In still yet other embodiments, the compositions of the present invention include about 25 wt % of a surfactant. In some embodiments, the compositions of the present invention include about 100 ppm to about 1000 ppm of a surfactant.

Nonionic Surfactants

Suitable nonionic surfactants suitable for use with the compositions of the present invention include alkoxylated surfactants. Suitable alkoxylated surfactants include alkoxylates made from ethylene (EO), propylene (PO), and butylene (BO) oxides. Suitable alkoxylated surfactants include homo or copolymers or terpolymers, capped EO/PO/BO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC11; mixtures thereof, or the like. More specifically the composition of the present invention can include alkoxylated primary or secondary alcohol having from 8 to 18 carbon atoms reacted with from 2 to 12 moles of ethylene, and/or propylene, and/or butylene oxide. In an embodiment the nonionic has from 3 to 18 moles of alkylene oxides, in another embodiment from 3 to about 10 moles of ethylene oxide, and in yet another embodiment about 7 moles of EO. These materials are commercially available and well-known nonionic surfactants. The following materials are useful: lauryl alcohol ethoxylated with 3 moles of ethylene oxide (EO), coco alcohol ethoxylated with 3 moles EO, stearyl alcohol ethoxylated with 5 moles EO, mixed $C_{12}$-$C_{15}$ alcohol ethoxylated with 7 moles EO, mixed secondary $C_{11}$-$C_{15}$ alcohol ethoxylated with 7 moles EO, mixed $C_9$-$C_{11}$ linear alcohol ethoxylated with 6 moles EO and the like. In an embodiment the nonionic has from 8 to 15 carbon atoms in the alkyl group. When this alkyl group is used a nonionic is the mixed $C_{12}$-$C_{15}$ alcohol ethoxylated with 7 moles EO. In an embodiment it comprises the alcohol alkoxylates, particularly the alcohol ethoxylates and propoxylates, especially the mixed ethoxylates and propoxylates, particularly with 3-7 oxyethylene (EO) units and 3-7 oxypropylene (PO) units such as the alcohol Dehypon™ available from Cognis Corporation, having 5 EO units and 4 PO units. These materials may be present in a wide range of concentrations, such as, for example, from 0.1 to 25% by weight of the concentrate or solution, from 1 to 25% by weight of the concentrate or solution, 1 to 20% by weight of the concentrate or solution, 2 to 15% by weight of the concentrate or solution, or 4 to 12% by weight of the concentrate or solution.

Nonionic surfactants include synthetic or natural alcohols that are alkoxylated (with ethylene and/or propylene and/or butylenes oxide) to yield a variety of $C_6$-$C_{24}$ alcohol ethoxylates and/or propoxylates and/or butoxylates (preferably $C_6$-$C_{14}$ alcohol ethoxylates and/or propoxylates and/or butoxylates having 1 to about 20 alkylene oxide groups (preferably about 9 to about 20 alkylene oxide groups); $C_6$-$C_{24}$ alkylphenol ethoxylates (preferably $C_8$-$C_{10}$ alkylphenol ethoxylates) having 1 to about 100 ethylene oxide groups (preferably about 12 to about 20 ethylene oxide groups); and $C_6$-$C_{24}$ alkylpolyglycosides (preferably $C_6$-$C_{20}$ alkylpolyglycosides) having 1 to about 20 glycoside groups (preferably about 9 to about 20 glycoside groups).

Semi-Polar Nonionic Surfactants

The semi-polar type of nonionic surface active agents are another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

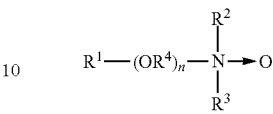

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, isododecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents; including alkylbenzene sulfonates.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R-O-(CH_2CH_2O)_n(CH_2)_m-CO_2X \qquad (3)$$

in which R is a $C_8$ to $C_{22}$ alkyl group or

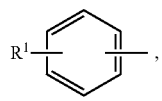

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

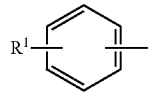

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Anionic surfactants include $C_6$-$C_{24}$ alkylbenzene sulfonates; $C_6$-$C_{24}$ olefin sulfonates; $C_6$-$C_{24}$ paraffin sulfonates; cumene sulfonate; xylene sulfonate; $C_6$-$C_{24}$ alcohol sulfates (preferably $C_6$-$C_{12}$ alcohol sulfates); and $C_6$-$C_{24}$ alcohol ether sulfates having 1 to about 20 ethylene oxide groups.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

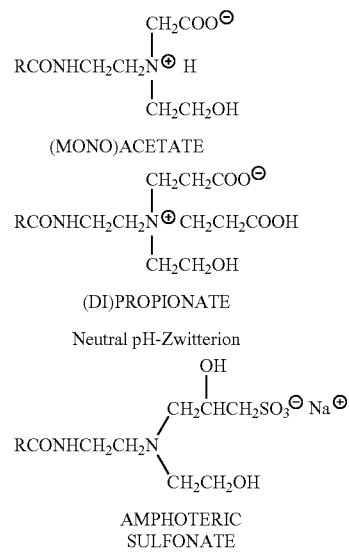

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$($CH_2$—$CH_2$—$CO_2Na)_2$—$CH_2$—$CH_2$—OH or $C_{12}$-alkyl-C(O)—N(H)—$CH_2$—$CH_2$—$N^+$($CH_2$—$CO_2Na)_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

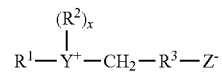

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

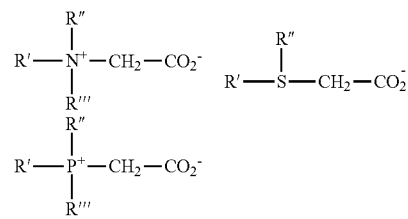

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO_3^-)$, in which R is a $C_6-C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

In an embodiment, the compositions of the present invention include a betaine. For example, the compositions can include cocoamidopropyl betaine.

Other Additional Ingredients

In some embodiments, the compositions of the present invention can include other additional ingredients. Additional ingredients suitable for use with the compositions of the present invention include, but are not limited to, acidulants, stabilizing agents, e.g., chelating agents or sequestrants, buffers, detergents, wetting agents, defoaming agents, thickeners, foaming agents, solidification agents, aesthetic enhancing agents (i.e., colorants, odorants, or perfumes) and other cleaning agents. These additional ingredients can be preformulated with the compositions of the invention or added to the system before, after, or substantially simultaneously with the addition of the compositions of the present invention. Additionally, the compositions can be used in conjunction with one or more conventional cleaning agents, e.g., an alkaline detergent.

Acidulants

In some embodiments, the compositions of the present invention include an acidulant. The acidulant can act as a catalyst for conversion of carboxylic acid to peroxycarboxylic acid. The acidulant can be effective to form a concentrate composition with pH of about 0.01 to about 7 or less, a pH of about 1 to about 6, or a pH of about 2 to about 5. The acidulant can be effective to form a use composition with pH of about 4 to about 9, about 5 to about 8, about 5.5 to about 7.5. In some embodiments, an acidulant can be used to lower the pH of an alkaline cleaning solution to a pH of about 10, about 10 or less, about 9, about 9 or less, about 8, about 8 or less, about 7, about 7 or less, about 6, or about 6 or less. In an embodiment, the acidulant includes an inorganic acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, benzene sulfonic acid, linear alkyl benzene sulphonic acid, cumene sulfonic acid, xylene sulfonic acid, formic acid, acetic acid, glycolic acid, mono, di, or tri-halocarboyxlic acids, picolinic acid, dipicolinic acid, and mixtures thereof. In some embodiments, the compositions of the present invention are free or substantially free of a phosphorous based acid.

In some embodiments, the acidulant selected can also function as a stabilizing agent. Thus, the compositions of the present invention can be substantially free of an additional stabilizing agent.

In certain embodiments, the present composition includes about 0.5 to about 80 wt-% acidulant, about 1 to about 50 wt %, about 5 to about 30 wt-% acidulant, or about 7 to about 14 wt-% acidulant. It is to be understood that all values and ranges between these values and ranges are encompassed by the compositions of the present invention.

Stabilizing Agents

In some embodiments, the compositions of the present invention include one or more stabilizing agents. The stabilizing agents can be used, for example, to stabilize the peracid and hydrogen peroxide and prevent the premature oxidation of this constituent within the composition of the invention.

In some embodiments, an acidic stabilizing agent can be used. Thus, in some embodiments, the compositions of the present invention can be substantially free of an additional acidulant.

Suitable stabilizing agents include, for example, chelating agents or sequestrants. Suitable sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid).

In some embodiments, the compositions of the present invention include dipicolinic acid as a stabilizing agent. Compositions including dipicolinic acid can be formulated to be free or substantially free of phosphorous. It has also been observed that the inclusion of dipicolinic acid in a composition of the present invention aids in achieving the phase stability of the compositions, compared to other conventional stabilizing agents, e.g., 1-hydroxy ethylidene-1,1-diphosphonic acid $(CH_3C(PO_3H_2)_2OH)$ (HEDP).

When nonionic surfactants having an ethylene oxide (EO) hydrophilic block are used in compositions of the invention and/or when certain other anionic and/or certain other amine oxide surfactants, some formulations may phase separate or suffer from visible cloudiness or haziness. In the event of such phase separation or visible cloudiness, a small amount of a hydrotrope, such as sodium cumene sulfonate ("SCS") may be added to the composition. Up to about 10 weight percent, up to about 8 weight percent, up to about 5 weight percent, and up to about 3 weight percent hydrotrope may be added to clear and/or eliminate phase separation of the formulation.

In other embodiments, the sequestrant can be or include phosphonic acid or phosphonate salt. Suitable phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(m-ethylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g, HEDP are included in the compositions of the present invention.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), $(N[CH_2PO_3H_2]_3)$, available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N,N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In certain embodiments, the present composition includes about 0.01 to about 10 wt-% stabilizing agent, about 0.4 to about 4 wt-% stabilizing agent, about 0.6 to about 3 wt-% stabilizing agent, about 1 to about 2 wt-% stabilizing agent. It is to be understood that all values and ranges within these values and ranges are encompassed by the present invention.

Wetting or Defoaming Agents

Also useful in the compositions of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention.

Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfonated or sulfated derivatives; fatty acids and/or their soaps such as alkali, alkaline earth metal soaps; and phosphates and phosphate esters such as alkyl and alkaline diphosphates, and tributyl phosphates among others; and mixtures thereof.

In some embodiments, the compositions of the present invention can include antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 20 wt-%, from about 0.01 wt-% to 5 wt-%, or from about 0.01 wt-% to about 1 wt-%.

In some embodiments, the compositions of the present invention can include antifoaming agents or defoaming agents which are based on alcohol alkoxylates that are stable in acid environments and are oxidatively stable. To this end one of the more effective antifoaming agents are the alcohol alkoxylates having an alcohol chain length of about C8-12, and more specifically C9-11, and having poly-propylene oxide alkoxylate in whole or part of the alkylene oxide portion. Commercial defoamers commonly available of this type include alkoxylates such as the BASF Degressal's; especially Degressal SD20.

Thickening or Gelling Agents

The compositions of the present invention can include any of a variety of known thickeners. Suitable thickeners include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. Other suitable thickeners include synthetic materials, for example, polyacrylates, polyacrylamides, polyalkylene glycols and derivatives including polyethylene glycols or polypropylene glycols, polyvinyl derivatives such as polyvinyl alcohols and/or polyvinyl acetates, or co-polymers thereof, and other polyvinyl derivatives, and mixtures thereof. Polycarboxylic acids are also useful as thickening agents in compositions of the invention. ACUS OL® 445 is a partially neutralized, liquid detergent polymer. Other polyacrylic acids of molecular weight 4500 (CRITERION 2005) and 8000 (CRITERION 2108) can be purchased from Kemira Chemicals, Kennesaw, Ga. Other thickening agents include, but are not limited to, Soakalan CP5 available from BASF, Coatex DE185, and Isol Dispersant HN44. In some embodiments, the thickener included is non oxidizable and storage stable under the pH conditions of the invention. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition. However, as a general guideline, the viscosity of thickener within the present composition ranges from about 0.1 wt-% to about 5 wt-%, from about 0.1 wt-% to about 1.0 wt-%, or from about 0.1 wt-% to about 0.5 wt-%.

Solidification Agents

The present compositions can include a solidification agent, which can participate in maintaining the compositions in a solid form. In some embodiments, the solidification agent can form and/or maintain the composition as a solid. In other embodiments, the solidification agent can solidify the composition without unacceptably detracting from the eventual release of the sulfonated peroxycarboxylic acid. The solidification agent can include, for example, an organic or inorganic solid compound having a neutral inert character or making a functional, stabilizing or detersive contribution to the present composition. Suitable solidification agents include solid or paste polyethylene glycols (PEG), solid or paste polypropylene glycols, solid EO/PO block copolymer, amide, urea (also known as carbamide), nonionic surfactant (which can be employed with a coupler), anionic surfactant, starch that has been made water-soluble (e.g., through an acid or alkaline treatment process), cellulose that has been made water-soluble, inorganic agent, poly(maleic anhydride/methyl vinyl ether), polymethacrylic acid, other generally functional or inert materials with high melting points, mixtures thereof, and the like;

Suitable glycol solidification agents include a solid polyethylene glycol or a solid polypropylene glycol, which can, for example, have molecular weight of about 1,400 to about 30,000. In certain embodiments, the solidification agent includes or is solid PEG, for example PEG 1500 up to PEG 20,000. In certain embodiments, the PEG includes PEG 1450, PEG 3350, PEG 4500, PEG 8000, PEG 20,000, and the like. Suitable solid polyethylene glycols are commercially available from Union Carbide under the tradename CARBOWAX.

Suitable amide solidification agents include stearic monoethanolamide, lauric diethanolamide, stearic diethanolamide, stearic monoethanol amide, cocodiethylene amide, an alkylamide, mixtures thereof, and the like. In an embodiment, the present composition can include glycol (e.g., PEG) and amide.

Suitable nonionic surfactant solidification agents include nonylphenol ethoxylate, linear alkyl alcohol ethoxylate, ethylene oxide/propylene oxide block copolymer, mixtures thereof, or the like. Suitable ethylene oxide/propylene oxide block copolymers include those sold under the Pluronic tradename (e.g., Pluronic 108 and Pluronic F68) and commercially available from BASF Corporation. In some embodiments, the nonionic surfactant can be selected to be solid at room temperature or the temperature at which the composition will be stored or used. In other embodiments, the nonionic surfactant can be selected to have reduced aqueous solubility in combination with the coupling agent. Suitable couplers that can be employed with the nonionic surfactant solidification agent include propylene glycol, polyethylene glycol, mixtures thereof, or the like.

Suitable anionic surfactant solidification agents include linear alkyl benzene sulfonate, alcohol sulfate, alcohol ether sulfate, alpha olefin sulfonate, mixtures thereof, and the like. In an embodiment, the anionic surfactant solidification agent is or includes linear alkyl benzene sulfonate. In an embodiment, the anionic surfactant can be selected to be solid at room temperature or the temperature at which the composition will be stored or used.

Suitable inorganic solidification agents include phosphate salt (e.g., alkali metal phosphate), sulfate salt (e.g., magnesium sulfate, sodium sulfate or sodium bisulfate), acetate salt (e.g., anhydrous sodium acetate), Borates (e.g., sodium borate), Silicates (e.g., the precipitated or fumed forms (e.g., Sipernat 50® available from Degussa), carbonate salt (e.g., calcium carbonate or carbonate hydrate), other known hydratable compounds, mixtures thereof, and the like. In an embodiment, the inorganic solidification agent can include organic phosphonate compound and carbonate salt, such as an E-Form composition.

In some embodiments, the compositions of the present invention can include any agent or combination of agents that provide a requisite degree of solidification and aqueous solubility can be included in the present compositions. In other embodiments, increasing the concentration of the solidification agent in the present composition can tend to increase the hardness of the composition. In yet other embodiments, decreasing the concentration of solidification agent can tend to loosen or soften the concentrate composition.

In some embodiments, the solidification agent can include any organic or inorganic compound that imparts a solid character to and/or controls the soluble character of the present composition, for example, when placed in an aqueous environment. For example, a solidifying agent can provide controlled dispensing if it has greater aqueous solubility compared to other ingredients in the composition. Urea can be one such solidification agent. By way of further example, for systems that can benefit from less aqueous solubility or a slower rate of dissolution, an organic nonionic or amide hardening agent may be appropriate.

In some embodiments, the compositions of the present invention can include a solidification agent that provides for convenient processing or manufacture of the present composition. For example, the solidification agent can be selected to form a composition that can harden to a solid form under ambient temperatures of about 30 to about 50° C. after mixing ceases and the mixture is dispensed from the mixing system, within about 1 minute to about 3 hours, or about 2 minutes to about 2 hours, or about 5 minutes to about 1 hour.

The compositions of the present invention can include solidification agent at any effective amount. The amount of solidification agent included in the present composition can vary according to the type of composition, the ingredients of the composition, the intended use of the composition, the quantity of dispensing solution applied to the solid composition over time during use, the temperature of the dispensing solution, the hardness of the dispensing solution, the physical size of the solid composition, the concentration of the other ingredients, the concentration of the cleaning agent in the composition, and other like factors. Suitable amounts can include about 1 to about 99 wt-%, about 1.5 to about 85 wt-%, about 2 to about 80 wt-%, about 10 to about 45 wt-%, about 15% to about 40 wt-%, about 20% to about 30 wt-%, about 30% to about 70%, about 40% to about 60%, up to about 50 wt-%, about 40% to about 50%

Carriers

In some embodiments, the compositions of the present invention include a carrier. The carrier provides a medium which dissolves, suspends, or carries the other components of the composition. For example, the carrier can provide a medium for solubilization, suspension, or production of a sulfonated peroxycarboxylic acid and for forming an equilibrium mixture. The carrier can also function to deliver and wet the composition of the invention on an object. To this end, the carrier can contain any component or components that can facilitate these functions.

In some embodiments, the carrier includes primarily water which can promote solubility and work as a medium for reaction and equilibrium. The carrier can include or be primarily an organic solvent, such as simple alkyl alcohols, e.g., ethanol, isopropanol, n-propanol, benzyl alcohol, and the like. Polyols are also useful carriers, including glycerol, sorbitol, and the like.

Suitable carriers include glycol ethers. Suitable glycol ethers include diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether (commercially available as DOWANOL EPH™ from Dow Chemical Co.), propylene glycol phenyl ether (commercially available as DOWANOL PPH™ from Dow Chemical Co.), and the like, or mixtures thereof. Additional suitable commercially available glycol ethers (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™

Low Gravity, CELLOSOLVE™ acetate, CELLOSOLVE™, Ester EEP™ FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™ Methyl PROPASOL™ acetate, Methyl PROPASOL™, Propyl CARBITOL™, Propyl CELLOSOLVE™, Propyl DIPROPASOL™ and Propyl PROPASOL™.

In some embodiments, the carrier makes up a large portion of the composition of the invention and may be the balance of the composition apart from the sulfonated peroxycarboxylic acid, oxidizing agent, additional ingredients, and the like. The carrier concentration and type will depend upon the nature of the composition as a whole, the environmental storage, and method of application including concentration of the sulfonated peroxycarboxylic acid, among other factors. Notably the carrier should be chosen and used at a concentration which does not inhibit the efficacy of the sulfonated peroxycarboxylic acid in the composition of the invention for the intended use, e.g., bleaching, sanitizing, disinfecting.

In certain embodiments, the present composition includes about 5 to about 90 wt-% carrier, about 10 to about 80 wt % carrier, about 20 to about 60 wt % carrier, or about 30 to about 40 wt % carrier. It is to be understood that all values and ranges between these values and ranges are encompassed by the present invention.

Additional Function Ingredients

In some embodiments, the compositions include additional functional ingredients. Additional functional ingredients suitable for inclusion in the compositions include, but are not limited to, optical brighteners, soil antiredeposition agents, antifoam agents, low foaming surfactants, defoaming surfactants, pigments and dyes, softening agents, antistatic agents, anti-wrinkling agents, dye transfer inhibition/color protection agents, odor removal/odor capturing agents, soil shielding/soil releasing agents, ultraviolet light protection agents, fragrances, sanitizing agents, disinfecting agents, water repellency agents, insect repellency agents, anti-pilling agents, souring agents, mildew removing agents, allergicide agents, and mixtures thereof. In some embodiments, the additional functional ingredient or ingredients is formulated in the compositions. In other embodiments, the additional functional ingredient or ingredients is added separately during a cleaning process.

Color Stabilizing Agent

In some embodiments, the compositions optionally include a color stabilizing agent. A color stabilizing agent can be any component that is included to inhibit discoloration or browning of the composition. In some embodiments, a color stabilizing agent may be included in the compositions at an amount of from about 0.01 to about 5 wt %, from about 0.05 to about 3 wt %, and from about 0.10 to about 2 wt %.

Optical Brighteners

In some embodiments, the compositions optionally include an optical brightener. Brighteners are added to laundry detergents to replace whitening agents removed during washing and to make the clothes appear cleaner. Optical brighteners may include dyes that absorb light in the ultraviolet and violet region (usually 340-370 nm) of the electromagnetic spectrum, and re-emit light in the blue region (typically 420-470 nm). These additives are often used to enhance the appearance of the color of a fabric, causing a perceived "whitening" effect, making materials look less yellow by increasing the overall amount of blue light reflected. In some embodiments, optical brighteners suitable for inclusion in the compositions, include, but are not limited to, triazine-stilbenes (di-, tetra- or hexa-sulfonated), coumarins, imidazolines, diazoles, triazoles, benzoxazolines, biphenyl-stilbenes, and mixtures thereof. One or more optical brighteners may be used in the compositions. In some embodiments, optical brighteners are included in the compositions at an amount of from about 0.1 to about 5 wt %, from about 0.15 to about 3 wt %, or from about 0.2 to about 2 wt %. Examples of commercially available optical brighteners suitable for use in the compositions include, but are not limited to, DMS-X and CBS-X, a distyryl biphenyl derivative, both available from Vesta-Intracon BV.

Soil Antiredeposition Agents

In some embodiments, the compositions may optionally include antiredeposition agents. Without wishing to be bound by any particular theory, it is thought that antiredeposition agents aid in preventing loosened soil from redepositing onto cleaned fabrics. Antiredeposition agents may be made from complex cellulosic materials such as carboxymethylcellulose (CMC), or synthetic materials such as polyethylene glycol and polyacrylates. In other embodiments, polyphosphate builders may be included as an antiredeposition agent.

Use Compositions

The compositions of the present invention include concentrate compositions and use compositions. For example, a concentrate composition can be diluted, for example with water, to form a use composition. In an embodiment, a concentrate composition can be diluted to a use solution before applying to an object. For reasons of economics, the concentrate can be marketed and an end user can dilute the concentrate with water or an aqueous diluent to a use solution.

The level of active components in the concentrate composition is dependent on the intended dilution factor and the desired activity of the sulfonated peroxycarboxylic acid compound. Generally, a dilution of about 1 fluid ounce to about 10 gallons of water to about 10 fluid ounces to about 1 gallon of water is used for aqueous compositions of the present invention. In some embodiments, higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 40 ounces of concentrate per 100 gallons of water.

In some embodiments, when used in a laundry application, the concentrated compositions can be diluted at a dilution ratio of about 0.1 g/L to about 100 g/L concentrate to diluent, about 0.5 g/L to about 10.0 g/L concentrate to diluent, about 1.0 g/L to about 4.0 g/L concentrate to diluent, or about 1.0 g/L to about 2.0 g/L concentrate to diluent.

In other embodiments, a use composition can include about 0.01 to about 10 wt-% of a concentrate composition and about 90 to about 99.99 wt-% diluent; or about 0.1 to about 1 wt-% of a concentrate composition and about 99 to about 99.9 wt-% diluent.

Amounts of an ingredient in a use composition can be calculated from the amounts listed above for concentrate compositions and these dilution factors. In some embodiments, for example when used in a laundry application, the concentrated compositions of the present invention are diluted such that the sulfopercarboxylic acid is present at from about 20 ppm to about 80 ppm. In other embodiments, the concentrated compositions of the present invention are diluted such that the sulfopercarboxylic acid is present at about 20 ppm, about 40 ppm, about 60 ppm, about 80 ppm, about 500 ppm, about 1000 ppm, or about 10,000 to about 20,000 ppm. It is to be understood that all values and ranges between these values and ranges are encompassed by the present invention.

Methods Employing the Sulfoperoxycarboxylic Acid Compounds and Compositions

In some aspects, the present invention includes methods of using the sulfoperoxycarboxylic acid compounds and compositions of the present invention. In some embodiments, these methods employ the antimicrobial and/or bleaching activity of the sulfoperoxycarboxylic acid. For example, the invention includes a method for reducing a microbial population, a method for reducing the population of a microorganism on skin, a method for treating a disease of skin, a method for reducing an odor, and/or a method for bleaching. These methods can operate on an article, surface, in a body or stream of water or a gas, or the like, by contacting the article, surface, body, or stream with a sulfoperoxycarboxylic acid compound or composition of the invention. Contacting can include any of numerous methods for applying a compound or composition of the invention, such as spraying the compounds or compositions, immersing the article in the compounds or compositions, foam or gel treating the article with the compounds or composition, or a combination thereof.

In some aspects, a composition of the present invention includes an amount of sulfoperoxycarboxylic acid of the present invention effective for killing one or more of the food-borne pathogenic bacteria associated with a food product, including, but not limited to, *Salmonella typhimurium*, *Salmonella javiana*, *Campylobacter jejuni*, *Listeria monocytogenes*, and *Escherichia coli* O157:H7, yeast, and mold. In some embodiments, the compositions of the present invention include an amount of sulfoperoxycarboxylic acid effective for killing one or more of the pathogenic bacteria associated with a health care surfaces and environments including, but not limited to, *Salmonella typhimurium*, *Staphylococcus aureus*, methicillin resistant *Staphylococcus aureus, Salmonella choleraesurus, Pseudomonas aeruginosa, Escherichia coli*, mycobacteria, yeast, and mold. The compounds and compositions of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compounds and compositions of the present invention, as described above, have activity against a wide variety of human pathogens. The present compounds and compositions can kill a wide variety of microorganisms on a food processing surface, on the surface of a food product, in water used for washing or processing of food product, on a health care surface, or in a health care environment.

The compounds of the invention can be used for a variety of domestic or industrial applications, e.g., to reduce microbial or viral populations on a surface or object or in a body or stream of water. The compounds can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media; hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compounds of the invention can also be applied to soft surfaces such as food and skin (e.g., a hand). The present compounds can be employed as a foaming or nonfoaming environmental sanitizer or disinfectant.

The compounds and compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compounds can also be used in veterinary products such as mammalian skin treatments or in products for sanitizing or disinfecting animal enclosures, pens, watering stations, and veterinary treatment areas such as inspection tables and operation rooms. The present compounds can be employed in an antimicrobial foot bath for livestock or people. The compounds of the present invention can also be employed as an antimicrobial teat dip.

In some aspects, the compounds of the present invention can be employed for reducing the population of pathogenic microorganisms, such as pathogens of humans, animals, and the like. The compounds exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens can cause a variety of diseases and disorders, including mastitis or other mammalian milking diseases, tuberculosis, and the like. The compounds of the present invention can reduce the population of microorganisms on skin or other external or mucosal surfaces of an animal. In addition, the present compounds can kill pathogenic microorganisms that spread through transfer by water, air, or a surface substrate. The compounds need only be applied to the skin, other external or mucosal surfaces of an animal water, air, or surface.

In some embodiments, the compounds and compositions of the present invention can be used to reduce the population of prions on a surface. Prions are proteinaceous infections particles free of nucleic acid. Prions are known to cause several brain diseases including kuru, Creutzfeldt-Jakob disease, Gerstmann-Straussler-Scheinker disease, and fatal familial insomnia in humans; scrapie in sheep; bovine spongiform encephalopathy (Mad Cow Disease) in cattle; transmissible mink encephalopathy in mink; chronic wasting disease in deer and elk; and feline spongiform encephalopathy in cats. These diseases lead to symptoms including dementia, ataxia, behavioral disturbances, dizziness, involuntary movement, and death. Prions can be transmitted by exposure to infected tissue and brain tissue, spinal cord tissue, pituitary tissue, and eye tissue in particular. In some embodiments, the compounds and compositions of the present invention can be used to reduce a population of prions according to a method as described in U.S. Pat. No. 7,470,655, the entire contents of which are hereby incorporated by reference.

The antimicrobial compounds can also be used on foods and plant species to reduce surface microbial populations; used at manufacturing or processing sites handling such foods and plant species; or used to treat process waters around such sites. For example, the compounds can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compounds of the invention can be used to treat produce transport waters such as those found in flumes, pipe transports, cutters, slicers, blanchers, retort systems, washers, and the like. Particular foodstuffs that can be treated with compounds of the invention include eggs, meats, seeds, leaves, fruits and vegetables. Particular plant surfaces include both harvested and growing leaves, roots, seeds, skins or shells, stems, stalks, tubers, corms, fruit, and the like. The compounds may also be used to treat animal carcasses to reduce both pathogenic and non-pathogenic microbial levels.

The antimicrobial compounds can also be used to treat waste water where both its antimicrobial function and its oxidant properties can be utilized. Aside from the microbial issues surrounding waste water, it is often rich in malodorous compounds of reduced sulfur, nitrogen or phosphorous. A strong oxidant such as the present invention converts these compounds efficiently to their odor free derivatives e.g. the sulfates, phosphates and amine oxides. These same properties are very useful in the pulp and paper industry where the property of bleaching is also of great utility.

In some aspects, the compounds of the present invention can be employed for epoxidations. The polymer industry is a major consumer of peracids, especially peroxyacetic acid but the typical equilibrium peroxyacetic acid also includes some strong acid residues which are problematic for the epoxide derivatives. A stable peracid isolate is therefore potentially of great utility in this industry.

In some aspects, the compounds and compositions of the present invention are useful in the cleaning or sanitizing of containers, processing facilities, or equipment in the food service or food processing industries. The compounds and compositions have particular value for use on food packaging materials and equipment, and especially for cold or hot aseptic packaging. Examples of process facilities in which the compound of the invention can be employed include a milk line dairy, a continuous brewing system, food processing lines such as pumpable food systems and beverage lines, etc. Food service wares can be disinfected with the compound of the invention. For example, the compounds can also be used on or in ware wash machines, low temperature ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash and low temperature ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compounds and compositions can also be used on or in other industrial equipment and in other industrial process streams such as heaters, cooling towers, boilers, retort waters, rinse waters, aseptic packaging wash waters, and the like. The compounds can be used to treat microbes and odors in recreational waters such as in pools, spas, recreational flumes and water slides, fountains, and the like.

A filter containing the compound can reduce the population of microorganisms in air and liquids. Such a filter can remove water and air-borne pathogens such as *Legionella*.

The present compounds can be employed for reducing the population of microbes, fruit flies, or other insect larva on a drain or other surface.

The compounds of the present invention can also be employed by dipping food processing equipment into the use solution, soaking the equipment for a time sufficient to sanitize the equipment, and wiping or draining excess solution off the equipment, The compound may be further employed by spraying or wiping food processing surfaces with the use solution, keeping the surfaces wet for a time sufficient to sanitize the surfaces, and removing excess solution by wiping, draining vertically, vacuuming, etc.

The compounds of the present invention may also be used in a method of sanitizing hard surfaces such as institutional type equipment, utensils, dishes, health care equipment or tools, and other hard surfaces.

The antimicrobial compounds can be applied to microbes or to soiled or cleaned surfaces using a variety of methods. These methods can operate on an object, surface, in a body or stream of water or a gas, or the like, by contacting the object, surface, body, or stream with a compound of the invention. Contacting can include any of numerous methods for applying a compound, such as spraying the compound, immersing the object in the compound, foam or gel treating the object with the compound, or a combination thereof.

A concentrate or use concentration of a compound of the present invention can be applied to or brought into contact with an object by any conventional method or apparatus for applying an antimicrobial or cleaning compound to an object. For example, the object can be wiped with, sprayed with, foamed on, and/or immersed in the compound, or a use solution made from the compound. The compound can be sprayed, foamed, or wiped onto a surface; the compound can be caused to flow over the surface, or the surface can be dipped into the compound. Contacting can be manual or by machine. Food processing surfaces, food products, food processing or transport waters, and the like can be treated with liquid, foam, gel, aerosol, gas, wax, solid, or powdered stabilized compounds according to the invention, or solutions containing these compounds.

Laundry Applications

In some aspects, the compounds and compositions can also be employed in washing and bleaching and sanitizing or disinfecting or sterilizing articles, e.g., woven and non-woven textile articles, garments, fabrics, and the like, which have become contaminated. The articles are contacted with the compositions of the invention at use temperatures in the range of about 4° C. to 80° C., for a period of time effective to reduce microbial populations to the level of sanitizing, disinfecting, or sterilizing the articles. Additionally, in some aspects the compounds and compositions can be employed as a sporicidal agent.

In other aspects, the compositions can be used to treat articles that are soiled, stained, in need of refreshing to remove odors, and/or that are in need of brightening. In yet other aspects, the compositions may be used to treat articles by introducing a surface enhancing additive to the article. For example, the compositions may be used to treat an article with optical brighteners, water absorption or de-absorption aides, soil repellents, insecticides, fungicides, anti-wrinkle agents, softeners, odor removal/odor capturing agents, soil shielding/soil releasing agents, anti-pilling agents, mildew control agents, and combinations thereof.

In some embodiments, the compositions can be used to wash, bleach and/or antimicrobially treat articles at a temperature of about 30° C. to about 50° C. or about 40° C. For example, in some embodiments, the compounds of the present invention can be injected into a laundering cycle— including but not limited to the pre-wash, wash, souring, extraction, softening, or rinse, or combinations thereof, —waters of a laundry machine and contacted with contaminated fabric for a time sufficient to effect microbial reductions on the fabric; including inhibition, sanitization, disinfection, sterilization, or as a sporicidal agent. Likewise, the compounds and compositions can also be employed in post washing cycles such as steam tunnels, ironers, or dryers to impart the same antimicrobial and bleaching efficacies. In some embodiments, the contaminated fabric is contacted with the compounds and compositions of the present invention for about 5 to about 30 minutes. Excess solution can then be removed by rinsing and/or centrifuging and/or pressing and/or drying the fabric.

In some aspects, the compounds and compositions of the present invention can be used as a combination detergent to remove soils from a textile substrate, and/or as an antimicrobial agent (including as a sanitizer, disinfectant, sporicidal reduction, or sterilant) and/or as a bleaching agent to whiten or lighten or remove stains from a substrate, e.g., hard surface, or fabric. Any combination of the aforementioned washing processes can be employed in aspects of the present invention. The compounds of the present invention can be used to bleach or remove stains from any conventional woven or non-woven textile, including but not limited to, cotton, poly-cotton blends, wool, aramids, polyurethanes, olefins, polyactids, nylons, silk, rayon, flax, jute, acrylics, and polyesters. The compounds of the present invention are also textile tolerant, i.e., they will not substantially degrade the textile to which they are applied. The compounds of the present invention can be used to remove a variety of stains from a variety of sources including, but not limited to, cosmetics, lipstick, pigment/sebum, pigment/lanolin, soot, olive oil, mineral oil, motor oil, blood, make-up, red wine, tea, ketchup, mustards, curries, body soils (sebum, urine, fecal matter, etc.), and combinations thereof. It is noted than when preparing compositions of the invention useful as a combination detergent, bleach, and effective microbial reducer for use on textiles that the composition may be substantially nitrogen-based chelant free, phosphorous and/or phosphate and/or phosphonate free, and heavy metals—specifically transition metals, post-transition metals, and metalloids—with an atomic number above 38.

In some aspects, the compounds and compositions of the present invention can be used as a bleaching agent to whiten or lighten or remove stains from a substrate, e.g., hard surface, or fabric. The compounds of the present invention can be used to bleach or remove stains from any conventional textile, including but not limited to, cotton, poly-cotton blends, wool, aramids, polyurethanes, olefins, polyactids, nylons, silk, rayon, flax, jute, acrylics, and polyesters. The compounds of the present invention are also textile tolerant, i.e., they will not substantially degrade the textile to which they are applied. The compounds of the present invention can be used to remove a variety of stains from a variety of sources including, but not limited to, cosmetics, lipstick, pigment/sebum, pigment/lanolin, soot, olive oil, mineral oil, motor oil, blood, make-up, red wine, tea, ketchup, mustards, curries, body soils (sebum, urine, fecal matter, etc.), and combinations thereof.

In some embodiments, the compounds of the present invention can be used as a low odor, acidic bleaching and/or detersive agent at an acidic pH, e.g., about 1, 2, 3, and up to about 7. In some embodiments, the compounds of the present invention can be used as a low odor bleaching agent at a neutral pH, i.e., about 7. In some embodiments, the compounds of the present invention can be used at an alkaline pH, e.g., about 8, 9, or 10. In still yet other embodiments, the compounds of the present invention can be used as an acidic bleaching agent that can act as an all in one sour, bleaching and antimicrobial product.

The compounds and compositions of the present invention can be used alone to treat the articles, e.g., woven or non-woven textiles, or can be used in conjunction with conventional detergents suitable for the articles to be treated. The compounds and compositions of the invention can be used with conventional detergents in a variety of ways, for example, the compounds and compositions of the invention can be formulated with a conventional detergent. In other embodiments, the compounds and compositions of the invention can be used to treat the article as a separate additive from a conventional detergent. When used as a separate additive, the compounds and compositions of the present invention can contact the article to be treated at any time. For example, the compounds and compositions of the invention can contact the article before, after, or substantially simultaneously as the articles are contacted with the selected detergent.

In some embodiments, when used as a bleaching and/or sanitizing/disinfecting/sporicidal/sterilant agent for a laundry application, a compound or mixture of compounds of the present invention will be present in a composition at about 5 ppm to about 10,000 ppm. In other embodiments, when used as a bleaching and/or sanitizing/disinfecting agent for a laundry application, a compound or mixture of compounds of the present invention will be present in a composition at about 25 ppm to about 5000 ppm. In other embodiments, when used as a bleaching and/or sanitizing/disinfecting agent for a laundry application, a compound or mixture of compounds of the present invention will be present in a composition at about 100 ppm up to about 1000 ppm. In other embodiments, when used as a bleaching and/or sanitizing/disinfecting agent in a laundry application, a compound or mixture thereof of the present invention will be present at about 20, about 40, about 60, or about 80 ppm. In still yet other embodiments, a compound or mixture of compounds of the present invention itself will be used as a bleaching agent, i.e., the compound or mixture of compounds will be present in a composition at about 100 wt %.

Clean in Place

Other hard surface cleaning applications for the compounds of the present invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like. CIP systems include the internal components of tanks, lines, pumps and other process equipment used for processing typically liquid product streams such as beverages, milk, and juices.

Generally, the actual cleaning of the in-place system or other surface (i.e., removal of unwanted offal therein) is accomplished with a different material such as a formulated detergent which is introduced with heated water. After this cleaning step, the instant composition would be applied or introduced into the system at a use solution concentration in unheated, ambient temperature water. CIP typically employ flow rates on the order of about 40 to about 600 liters per minute, temperatures from ambient up to about 70° C., and contact times of at least about 10 seconds, for example, about 30 to about 120 seconds. The present composition can remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its activity. These materials are useful at any conceivable temperatures.

A method of sanitizing substantially fixed in-place process facilities includes the following steps. The use solution of the invention is introduced into the process facilities at a temperature in the range of about 4° C. to 60° C. After introduction of the use solution, the solution is held in a container or circulated throughout the system for a time sufficient to sanitize the process facilities (e.g., to kill undesirable microorganisms). After the surfaces have been sanitized by means of the present composition, the use solution is drained. Upon completion of the sanitizing step, the system optionally may be rinsed with other materials such as potable water. The composition can be circulated through the process facilities for 10 minutes or less.

The present method can include delivering the present composition via air delivery to the clean-in-place or other surfaces such as those inside pipes and tanks. This method of air delivery can reduce the volume of solution required.

Methods for Contacting a Food Product

In some aspects, the present invention provides methods for contacting a food product with a sulfoperoxycarboxylic acid compounds or composition employing any method or apparatus suitable for applying such a compound or composition. For example, in some embodiments, the food product is contacted by a compound of the present invention with a spray of the compound, by immersion in the compound, by foam or gel treating with the compound. Contact with a spray, a foam, a gel, or by immersion can be accomplished by a variety of methods known to those of skill in the art for applying antimicrobial agents to food. Contacting the food product can occur in any location in which the food product might be found, such as field, processing site or plant, vehicle, warehouse, store, restaurant, or home. These same methods can also be adapted to apply the compounds of the present invention to other objects.

The present methods require a certain minimal contact time of the compound with food product for occurrence of significant antimicrobial effect. The contact time can vary with concentration of the use compound, method of applying the use compound, temperature of the use compound, amount of soil on the food product, number of microorganisms on the food product, type of antimicrobial agent, or the like. The exposure time can be at least about 5 to about 15 seconds. In some embodiments, the exposure time is about 15 to about 30 seconds. In other embodiments, the exposure time is at least about 30 seconds.

In some embodiments, the method for washing a food product employs a pressure spray including a compound of the present invention. During application of the spray solution on the food product, the surface of the food product can be moved with mechanical action, e.g., agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the microorganisms. The spray solution, before application, can also be heated to a temperature of about 15 to 20° C., for example, about 20 to 60° C. to increase efficacy. The spray stabilized compound can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One automatic spray application involves the use of a spray booth. The spray booth substantially confines the sprayed compound to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the stabilized compounds of the invention. These steam jets can be used in combination with cooling water to ensure that the treatment reaching the food product surface is less than 65° C., e.g., less than 60° C. The temperature of the spray on the food product is important to ensure that the food product is not substantially altered (cooked) by the temperature of the spray. The spray pattern can be virtually any useful spray pattern.

Immersing a food product in a liquid stabilized compound of the present invention can be accomplished by any of a variety of methods known to those of skill in the art. For example, the food product can be placed into a tank or bath containing the stabilized compound. Alternatively, the food product can be transported or processed in a flume of the stabilized compound. The washing solution can be agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the stabilized compound can be rinsed, drained, or evaporated off the food product.

In other embodiments, a food product can be treated with a foaming version a the compound of the present invention. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, including, for example, alkyl aryl sulfonates, quaternary ammonium compounds, alkyl sarcosines, betaines and alkyl amides. The foaming surfactant is typically mixed at time of use with the washing solution. Use solution levels of the foaming agents are from about 50 ppm to about 2.0 wt-%. At time of use, compressed air can be injected into the mixture, then applied to the food product surface through a foam application device such as a tank foamer or an aspirated wall mounted foamer.

In some embodiments, a food product can be treated with a thickened or gelled version of a compound of the present invention. In the thickened or gelled state the washing solution remains in contact with the food product surface for longer periods of time, thus increasing the antimicrobial efficacy. The thickened or gelled solution will also adhere to vertical surfaces. The compound or the washing solution can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

Methods for Beverage, Food, and Pharmaceutical Processing

The sulfoperoxycarboxylic acid compounds and compositions of the present invention can be used in the manufacture of beverage, food, and pharmaceutical materials including fruit juice, dairy products, malt beverages, soybean-based products, yogurts, baby foods, bottled water products, teas, cough medicines, drugs, and soft drinks. The compounds of the present invention can be used to sanitize, disinfect, act as a sporicide for, or sterilize bottles, pumps, lines, tanks and mixing equipment used in the manufacture of such beverages. Further, the sulfoperoxycarboxylic acid antimicrobial compounds of the present invention can be used in aseptic, cold filling operations in which the interior of the food, beverage, or pharmaceutical container is sanitized or sterilized prior to filling. In such operations, a container can be contacted with the sanitizing sulfoperoxycarboxylic acid compound, typically using a spray, dipping, or filling device to intimately contact the inside of the container with the sulfoperoxycarboxylic acid compound, for a sufficient period of time to reduce microorganism populations within the container. The container can then be emptied of the amount of sanitizer or sterilant used. After emptying, the container can be rinsed with potable water or sterilized water and again emptied. After rinsing, the container can be filled with the beverage, food, or pharmaceutical. The container can then be sealed, capped or closed and then packed for shipment for ultimate sale. The sealed container can be autoclaved or retorted for added microorganism kill In food, beverage, or pharmaceutical manufacturing, fungal microorganisms of the genus *Chaetomium* or *Arthrinium*, and spores or bacteria of the genus *Bacillus* spp. can be a significant problem in bottling processes, particularly in cold aseptic bottling processes. The sulfoperoxycarboxylic acid compounds of the present invention can be used for the purpose of controlling or substantially reducing (by more than a 5 $\log_{10}$ reduction) the number of *Chaetomium* or *Arthrinium* or *Bacillus* microorganisms in beverage or food or pharmaceutical bottling lines using cold aseptic bottling techniques.

In such techniques, metallic, aluminum or steel cans can be filled, glass bottles or containers can be filled, or plastic (PET or PBT or PEN) bottles, and the like can be filled using cold aseptic filling techniques. In such processes, the sulfoperoxycarboxylic acid materials of the invention can be used to sanitize the interior of beverage containers prior to filling with the carbonated (or noncarbonated) beverage. Typical carbonated beverages in this application include, but are not limited to, cola beverages, fruit beverages, ginger ale beverages, root beer beverages, iced tea beverages which may be non-carbonated, and other common beverages considered soft drinks. The sulfoperoxycarboxylic acid materials of the invention can be used to sanitize both the tanks, lines, pumps, and other equipment used for the manufacture and storage of the soft drink material and also used in the bottling or containers for the beverages. In an embodiment, the sulfoperoxycarboxylic acid sanitizing materials are useful for killing both bacterial and fungal microorganisms that can be present on the surfaces of the production equipment and beverage containers.

The sulfoperoxycarboxylic acid compounds of the present invention can effectively kill microorganisms (e.g., >1 $\log_{10}$ or up to about 5 $\log_{10}$ reduction in 30 seconds) from a concentration level of at least about 50 ppm, for example, about 150, about 500 ppm or about 1000 ppm of a sulfoperoxycarboxylic acid compound. In an embodiment, the sulfoperoxycarboxylic acid compound, excluding water, would be present at a concentration of about 0.001 to about 1 wt-%, for example, about 0.01 to about 0.15 wt-%, or about 0.05 to about 0.1 wt-%.

All acid, salt, base and other ionic and non-ionic forms of the compounds described are included as compounds of the invention. For example, if a compound is shown as an acid herein, the salt forms of the compound are also included. Likewise, if a compound is shown as a salt, the acid and/or basic forms are also included.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference. The invention is further illustrated by the following examples, which should not be construed as further limiting.

EXAMPLES

Some of the following Examples were performed using a sulfonated peroleic acid product. Without wishing to be bound by any particular theory, it is thought that the peracid formed from a commercially available sulfonated oleic acid starting material includes a mixture of the compounds of the present invention. It is thought that this is due, in part, to the nature of the sulfonated oleic acid starting material. That is, it is thought that because the sulfonated oleic acid starting material is derived from naturally occurring sources, it is not chemically pure, i.e., does not contain only one form of the sulfonated oleic acid. Thus, without wishing to be bound by any particular theory it is thought that sulfonated peroleic acid (hereinafter referred to as the "sulfonated peroleic acid product") used in these examples included a mixture of about 20-25 wt % Compound A (10-Hydroxy-9-sulfooctadecaneperoxoic acid) about 20-25 wt % Compound N (10,11-dihydroxy-9-sulfooctadecaneperoxoic acid), about 20-25 wt % Compound I (9-Hydroxy-10-sulfooctadecaneperoxoic acid), and about 20-25 wt % Compound O (8,9-dihydroxy-10-sulfooctadecaneperoxoic acid). The remainder of the peracid composition is thought to include about 5 to about 10 wt % of a mixture of these compounds.

Example 1

Use of a Sulfoperoxycarboxylic Acid as a Coupler Under High Level Disinfection Application Conditions Peroxyoctanoic acid (POOA) stability experiments were performed under high level disinfection (HLD) conditions to evaluate the stability of a composition of the present invention including a sulfonated peroleic acid product, compared with known commercially available disinfectants.

Octave FS®, a peroxyoctanoic containing product, commercially available from Ecolab Inc. was tested against Formulas A, B, and C, and mixtures thereof. Formula A was a mixture of: 2.5 wt % Dequest 2010 (commercially available from thermPhos), peracid grade; 61 wt % hydrogen peroxide (35%); 2.50 wt % sulfuric acid (98%); 6.0 wt % octanoic acid, 19 wt % Hostapur SAS (40%) (commercially available from Clariant); and 9.00 wt % SXS-40 (commercially available from Stepan Company). Formula B was a mixture of about 20 wt % of the sulfonated peroleic acid product, about 10% peroctanoic acid, about 15 wt % octanoic acid, and about 0.5 wt % hydrogen peroxide. Formula C was a mixture of about 25 wt % of the sulfonated peroleic acid product, and about 0.50 wt % hydrogen peroxide. Mixtures of Formulas A, B, and C were also tested. The test solutions were diluted with DI water to make a solution with about 1000 ppm POOA present at a pH of about 6.5. The table below shows the five solutions tested, and the amount of sulfonated peroleic acid product, POOA, and hydrogen peroxide available in ppm in each of the solutions as tested.

TABLE 2

| | Test solution composition | | | | |
|---|---|---|---|---|---|
| | #1 | #2 | #3 | #4 | #5 |
| Octave FS ® (wt %) | 10.00 | 0 | 0 | 0 | 0 |
| Formula A (wt %) | 0 | 4.2 | 0 | 0 | 0 |
| Formula B (wt %) | 0 | 0 | 0.88 | 0.55 | 0.33 |
| Formula C (wt %) | 0 | 0 | 0.22 | 0.55 | 0.77 |
| Final weight with added DI water (g) | 100 | 100 | 100 | 100 | 100 |
| Sulfonated peroleic acid product (ppm) | 0 | 0 | 2318 | 2459 | 2554 |
| POOA (ppm) | 1000 | 1000 | 800 | 500 | 300 |
| $H_2O_2$ | 8050 | 8928 | 55 | 55 | 55 |

The samples were stored at 40° C. and the amount of POOA present was measured by high performance liquid chromatography at the selected times. The following table shows the results of the HPLC analysis of the samples at various times.

TABLE 3

| | Test solution | | | | |
|---|---|---|---|---|---|
| Time (hrs) | 1 POOA (ppm) | 2 POOA (ppm) | 3 POOA (ppm) | 4 POOA (ppm) | 5 POOA (ppm) |
| 0 | 490 | 870 | 700 | 470 | 290 |
| 6 | 310 | 730 | 590 | 400 | 250 |
| 24 | 0 | 120 | 350 | 240 | 150 |
| 48 | 0 | 10 | 240 | 160 | 100 |
| 72 | 0 | 0 | 180 | 130 | 80 |
| 9 days | 0 | 0 | 20 | 0 | 0 |

These results are also graphically depicted in FIG. 1. As can be seen from the table above, and FIG. 1, the test solutions including a compound of the present invention, i.e., test solutions 3, 4, and 5, lost less POOA over the course of the first 24 hours compared to the other two test solutions. Even after 48 hours, a greater amount of POOA remained in the test solutions including a compound of the present invention, than in the other solutions tested. For each of the test solutions including a compound of the present invention, it was shown that the loss of POOA in the solutions was not linear, and that the decomposition rate of POOA slowed down dramatically at higher ratios of the sulfonated peroleic acid product to POOA.

Figure 2:
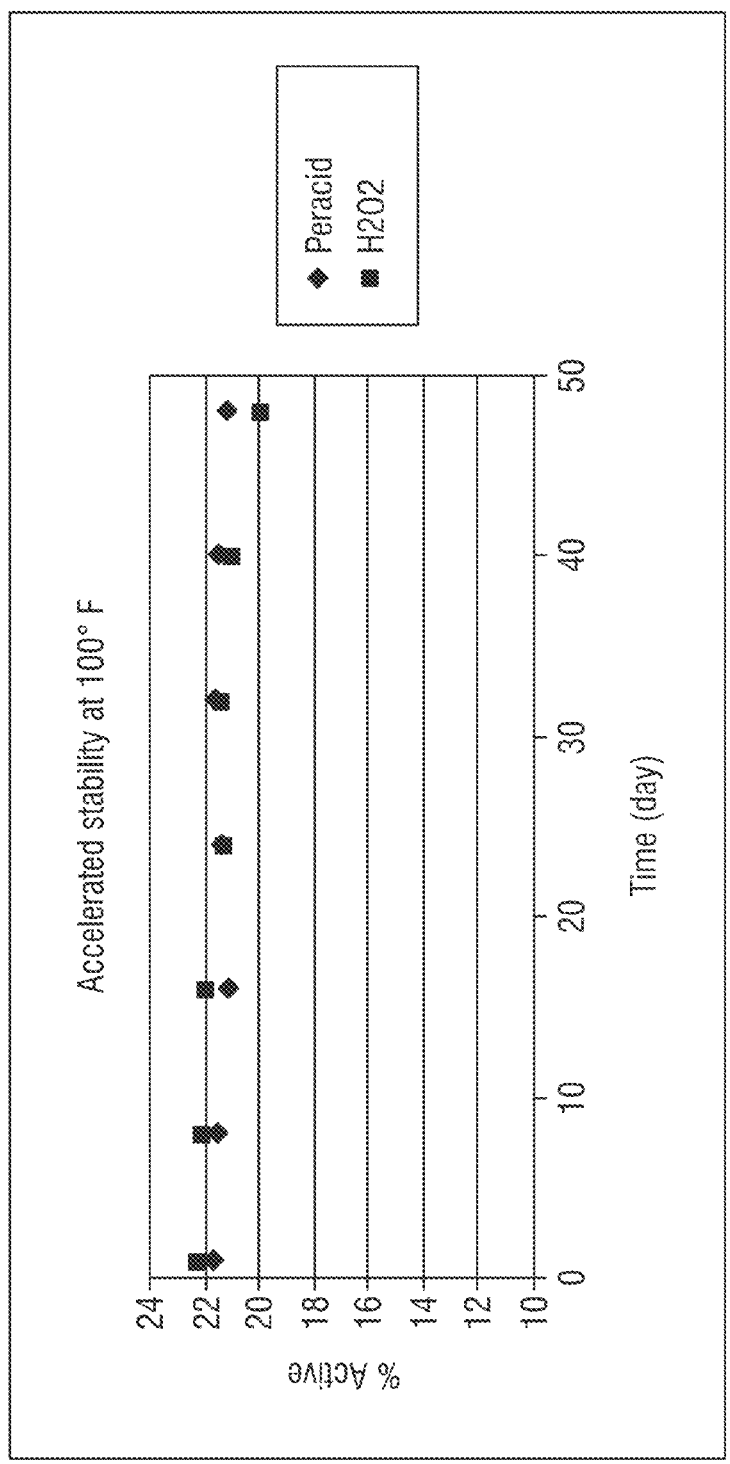
FIG. 2 is a graphical depiction of the stability of an exemplary composition of the present invention over time at an elevated temperature.

Another stability study was performed to evaluate the stability of a composition of the present invention at an elevated temperature, i.e., 100° F. A solution including about 2 wt % of the sulfonated peroleic acid product, and about 55 wt % $H_2O_2$, among other ingredients, was used. The amount of the sulfonated peroleic acid product and $H_2O_2$ was measured over the course of 48 days. The results are shown in FIG. 2. As can be seen in this figure, the peracid compound, the sulfonated peroleic acid product maintained its activity over the course of the trial, even at this accelerated temperature.

Yet another stability study was performed to evaluate the stability of peroxyoctanoic acid when contacted by a compound of the present invention, i.e., the sulfonated peroleic acid product, under ambient conditions. For this study, the pH was constant at about 6 to about 6.5. Three different formulas were tested for this study: Formula D included about 5 grams of a mixture of the sulfonated peroleic acid product, peroxyoctanoic acid, hydrogen peroxide and sodium cumene sulfate, among other ingredients; Formula E included about 0.5 g of a mixture of the sulfonated peroleic acid product, and peroxyoctanoic acid; and Formula F included Octave®, commercially available from Ecolab Inc. The amount of active peroxyoctanoic acid available at various times over the course of 15 days was measured. The results are shown in the table below.

TABLE 4

| Time (days) | Formula D POOA (ppm) | Formula E POOA (ppm) | Formula F POOA (ppm) |
|---|---|---|---|
| 0 | 590 | 640 | 570 |
| 1 | 550 | 590 | 500 |
| 4 | 470 | 480 | 360 |
| 6 | 420 | 400 | 240 |
| 8 | 410 | 360 | 160 |
| 11 | 360 | 270 | 70 |
| 14 | 310 | 230 | 30 |

Figure 3:
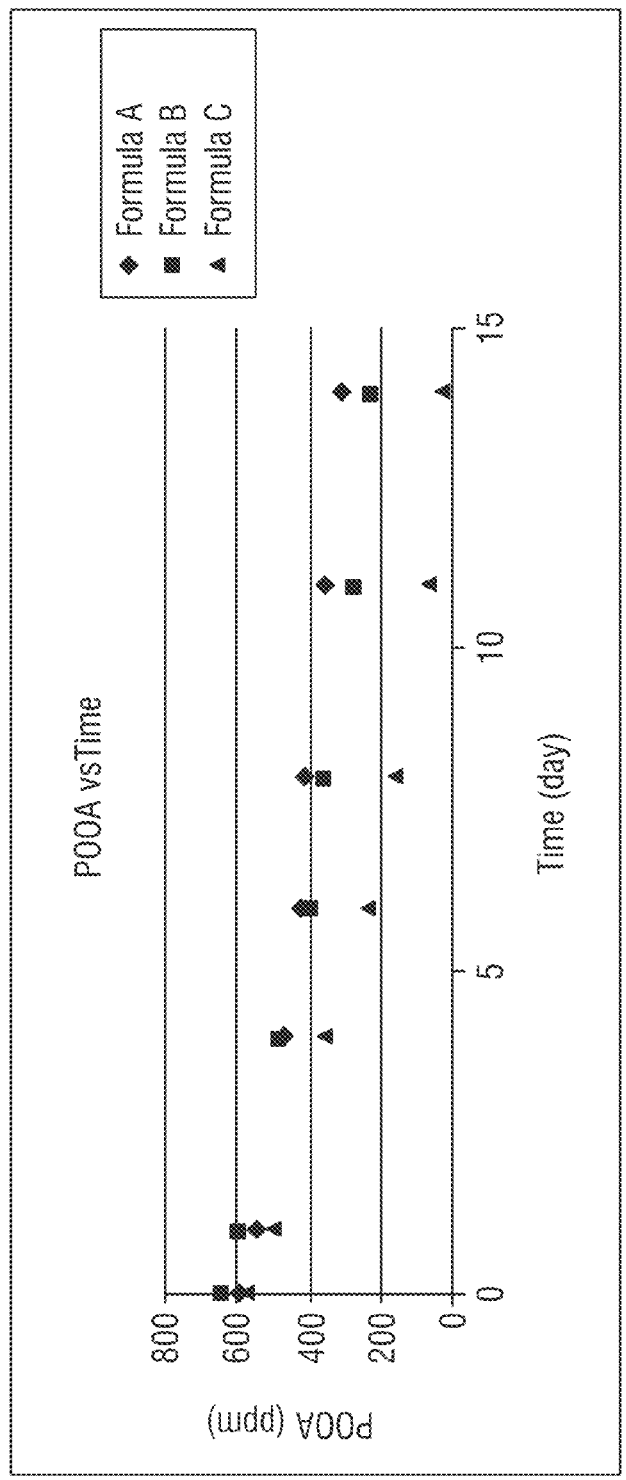
FIG. 3 is a graphical depiction of the ability of selected compositions of the present invention to stabilize percarboxylic acids over time.

These results are also graphically depicted in FIG. 3. As can be seen in this table, and figure, the formulas including a compound of the present invention, i.e., Formulas D and E, retained a higher level of POOA over the course of 15 days. Thus, without wishing to be bound by any particular theory it is thought that the addition of a composition including compounds of the present invention acts to stabilize other percarboxylic acids present in the composition.

Example 2

Use of a Sulfoperoxycarboxylic Acid as a Bleaching Agent

The use of a compound of the present invention as a bleaching agent was evaluated. The soil removal ability of the cleaning composition was determined by washing with artificially soiled fabric swatches. The soiled swatches were purchased from a manufacturer or distributor (e.g. Test Fabrics, Inc., West Pittston, Pa.). Soil types such as olive oil, sebum, makeup, wine are characteristic of natural soils found in laundry applications.

Soiled swatches were washed with the cleaning composition in a device such as a Terg-o-tometer (United States Testing Co., Hoboken, N.J.). The Terg-o-tometer is a laboratory washing device that consists of multiple pots that reside in a single temperature-controlled water bath, with overhead agitators under time and speed control. Wash test parameters include: wash temperature, wash duration, pH, mechanical agitation, dose of cleaning composition, water hardness, wash formula, and cloth/liquor ratio. After completing the appropriate exposure times the fabric samples were removed. The test chemistries were immediately flushed, and the swatches rinsed with cold synthetic 5 grain water until 5 cycles of fills and rinses were complete. The swatches were then laid flat and dried overnight on white polyester-cotton towels before reflectance readings were taken using a spectrophotometer, e.g., Hunter ColorQuest XE (reflectance) Spectrophotometer.

To determine the percent (%) soil removal (SR), e.g., bleaching ability, the reflectance of the fabric sample was measured on a spectrophotometer. The "L value" is a direct reading supplied by the spectrophotometer. L generally is indicative of broad visible spectrum reflectance, where a value of 100% would be absolute white. The % soil removal is calculated from the difference between the initial (before washing) lightness (L) value and the final L value (after washing):

$$SR = ((L_{final} - L_{initial})/(96 - L_{initial})) \times 100\%$$

A bleach test was run comparing a composition including a sulfonated peroleic acid product with the following commercially available bleaching/cleaning compositions: Ozonit®, and Oxysan® both available from Ecolab Inc. Ozonit® represents a 4.5% peroxyacetic acid product while Oxysan® represents a 0.6% peroxyoctanoic acid product. Formula A was a composition including about 2 wt % of sulfonated peroleic acid product, about 5 wt % peroxyacetic acid and about 1.5 wt % of peroxyoctanoic acid. Formula A was used at a concentration of 1200 ppm and further treated in two of the three cases with additional acetic acid to produce lowered pH test solutions. Ozonit® was used at a concentration of 2000 ppm. Oxysan® was tested at concentrations of 1272 and 2545 ppm. All of the wash solutions were further treated with Detergent MP® and TurboCharge II®, both available from Ecolab Inc and used at 500 and 750 ppm respectively. The bath/wash temperature was maintained at 100° F. Detergent MP® and TurboCharge II provide a common alkaline builder detergent base. The results from the bleaching test are shown in the table below.

TABLE 5

| Bleach Type | Stain Removal (%) from Cotton | | | Conc. of Bleach (mg/L) | pH |
| --- | --- | --- | --- | --- | --- |
| | Tea | Red Wine | Ketchup | | |
| Ozonit® | 29 | 59 | 27 | 2000 | 9.50 |
| Oxysan® | 21 | 66 | 19 | 1272 | 8.00 |
| 1X Oxysan® | 33 | 69 | 27 | 2545 | 8.00 |
| Formula A, pH 8.0 | 37 | 73 | 38 | 1000 | 8.00 |
| Formula A, pH 8.5 | 38 | 72 | 41 | 1000 | 8.50 |
| Formula A, pH 9.0 | 34 | 69 | 36 | 1000 | 9.00 |

As can be seen from this table, the compositions of Formula A achieved a higher percent stain removal than the commercially available solutions tested at all pH levels tested, especially in the cases of ketchup which represents a hydrophobic stain.

Formula A was also tested using a full scale Wash Wheel Bleach Test. The test was run with a commercial 35 lb side loading washing machine (UniMac UX35PVXR). Multi-paneled pre-stained test sheets (Ecomon No. 1 & Ecomon No. 4 included 14 bleachable and 12 pigment/unbleachable stained panels) were added to the otherwise empty machine before initiating a 20 minute washing program (typically at 40° C.). The chemistries were added in a 30 second staggered sequence via the overhead dispensing cups once the machine was filled with 48 L of 5 grain synthetic soft water. The initial chemistry added was the alkaline detergent product (about 84 g of Turboemulsion, commercially available from Ecolab Inc.). The bleaching chemistry was then added ~30 seconds after the surfactant-caustic blend and a 20 minute wash cycle was begun. After the wash cycle the machine was drained and 3 rinse cycles were executed. The sheets were retrieved and air dried at 70° F., overnight before measuring each swatch panel's reflectance with a Hunter ColorQuest XE (reflectance) Spectrophotometer (UV filter "IN"). The results are shown in the table below.

TABLE 6

| | L Reflectance Values | | | | [5]Stain Removal, % | |
| --- | --- | --- | --- | --- | --- | --- |
| | Initial stained swatch | [3]Turboemulsion only | TE + [6]Formula A | TE + [4]Ozonit | TE + Formula A | TE + Ozonit |
| Bleachable Stains | | | | | | |
| Tea on CO | 80.64 | 80.67 | 91.62 | 88.94 | 71.48 | 54.01 |
| Tea on PES/CO | 80.43 | 79.24 | 91.17 | 88.28 | 68.96 | 50.40 |
| Red Wine on CO | 73.66 | 85.94 | 93.03 | 92.06 | 86.72 | 82.36 |
| Red Wine on PES/CO, aged | 73.82 | 82.98 | 91.71 | 90.67 | 80.67 | 75.97 |
| Coffee on CO | 78.92 | 90.72 | 93.10 | 92.70 | 83.04 | 80.70 |
| Coffee on PES/CO | 79.77 | 92.27 | 93.62 | 93.28 | 85.34 | 83.26 |
| Black currant juice on CO | 64.40 | 88.37 | 93.54 | 92.82 | 92.22 | 89.94 |
| Black currant juice on PES/CO | 63.57 | 85.02 | 93.30 | 92.07 | 91.68 | 87.89 |
| Blood on CO IEC 456, aged | 46.25 | 89.51 | 90.60 | 91.48 | 89.14 | 90.91 |
| Blood on CO IEC 456, not aged | 49.36 | 93.06 | 93.81 | 93.88 | 95.30 | 95.45 |
| Blood/Milk/Ink on CO | 45.26 | 61.00 | 51.10 | 51.89 | 11.51 | 13.06 |
| Cocoa on CO IEC 456, not aged | 75.22 | 83.76 | 83.47 | 83.27 | 39.72 | 38.74 |
| Blood/Milk/Soot on CO | 58.87 | 86.37 | 69.87 | 70.54 | 29.62 | 31.44 |
| Egg/Soot on CO | 62.87 | 76.36 | 76.09 | 75.81 | 39.89 | 39.05 |
| average/14 | 66.65 | 83.95 | 86.15 | 85.55 | 68.95 | 65.23 |

TABLE 6-continued

|  | L Reflectance Values | | | | Stain Removal, %[5] | |
|---|---|---|---|---|---|---|
|  | Initial stained swatch | [3]Turboemulsion only | TE + [6]Formula A | TE + [4]Ozonit | TE + Formula A | TE + Ozonit |
| Unbleachable Stains | | | | | | |
| Pigment/Lanolin on CO | 71.98 | 80.90 | 78.63 | 80.55 | 27.70 | 35.68 |
| Pigment/Lanolin on PES/CO | 66.65 | 82.38 | 73.28 | 81.72 | 22.60 | 51.35 |
| Pigment/Sebum on CO | 73.19 | 87.70 | 84.02 | 86.76 | 47.49 | 59.48 |
| Pigment/Sebum on PES/CO | 70.64 | 87.97 | 77.82 | 86.74 | 28.33 | 63.49 |
| Soot/Olive Oil on CO | 47.93 | 69.90 | 62.45 | 64.87 | 30.21 | 35.23 |
| Soot/Olive Oil on PES/CO | 40.77 | 62.89 | 56.23 | 58.57 | 27.99 | 32.23 |
| Soot/Mineral Oil on CO | 59.76 | 72.35 | 68.93 | 71.80 | 25.30 | 33.21 |
| Soot/Mineral Oil on PES/CO | 55.62 | 80.15 | 73.89 | 78.78 | 45.25 | 57.36 |
| Used Motor Oil on CO | 65.91 | 73.06 | 70.99 | 71.77 | 16.89 | 19.47 |
| Used Motor Oil on PES/CO | 61.10 | 68.27 | 64.08 | 66.01 | 8.53 | 14.08 |
| Makeup on CO | 84.81 | 90.06 | 89.50 | 90.14 | 41.94 | 47.63 |
| Makeup on PES/CO | 85.16 | 92.57 | 91.91 | 92.14 | 62.24 | 64.42 |
| average/12 | 70.85 | 86.01 | 81.49 | 84.62 | 32.04 | 42.80 |

Notes:
[3]Turboemulsion (TE) is a commercially available all-in-one emulsion of alkaline metal chelators emulsified with a surfactant blend made by Ecolab, Inc. and was used in this test at 1750 ppm.
[4]Ozonit is a Peracetic acid -Hydrogen peroxide bleach disinfectant used at a concentration of 2000 ppm. Ozonit is a blend of Peracetic acid and Hydrogen peroxide made by Ecolab, Inc.
[5]The "Stain Removal, %" was calculated using the following formula: SR = ((Lfinal- Lintial)/(96-Lintial)) × 100% CO: Cotton; PES/CO: Polyester-Cotton blend As can be seen from this table, Formula A averages superior bleaching to Ozonit®. Although the superiority on these "bleachable" stains is only 3.7 points (5.4%), on those stains which better resist wash removal e.g. tea, the difference was as many as 17 points (24%) higher.

Another full scale wash testing was conducted using a wash wheel (full size side loading washing machine), but rather than individual soiled swatches this test utilized multipaneled sheets combining 14 "bleachable" stained swatches (Ecomon 4) and a second sheet which combined 12 "unbleachable" pigment/hydrocarbon stained swatches (Ecomon 1). These panels are custom made for Ecolab by wfk Testgewebe Gmbh of Bruggen, Germany. This extensive bleach test utilized a design experiment which varied concentrations sometimes simultaneously with temperatures etc. Following completion of the specified wash time, all Ecomon sheets were rinsed thoroughly, dried and their broad spectrum light reflectivities were measured, again with UV filtering to removal possible interference from optical brightener effects. Unlike the tergotometer data, the % stain removal wasn't calculated but was rather directly measured from the reflectance instrument (Minolta CM-2610d Spektrophotometer). A "Y" value representing broad spectrum reflectivity was reported. The higher the "Y" value, the whiter the material, and therefore, the greater the bleaching or stain removal.

In this test, Formula A was compared to Ozonit®, Ozonit Super® (a 15% peroxyacetic acid product available from Ecolab) and Oxysan® these were variously combined with the following commercially available alkaline-builder cleaning agents: Triplex Emulsion®, available from Ecolab Inc.; Turbo Usona®, available from Ecolab Inc.; Ozonit Super®, available from Ecolab Inc.; and Oxysan®, available from Ecolab Inc. The results are shown in the tables below.

TABLE 7

| | Bleaching Results | | | | | | | | |
|---|---|---|---|---|---|---|---|---|---|
| Procedure | Tea on CO | Tea on PES/CO | Red Wine on CO aged | Red Wine on PES/CO aged | Coffee on CO | Coffee on ES/CO | Black Currant Juice on CO | Black Currant Juice on PES/CO | Ave. |
| 1.5 ml/l [2]Triplex Emulsion + 1 ml/l Formula A Conditions: 15' 40° C. | 72.7 | 70.0 | 75.4 | 74.6 | 80.2 | 84.6 | 82.5 | 84.1 | 78.0 |
| 1.5 ml/l Triplex Emulsion + 2 ml/l Formula A Conditions: 15' 40° C. | 80.6 | 79.6 | 82.5 | 80.5 | 83.5 | 86.0 | 85.5 | 86.1 | 83.0 |

TABLE 7-continued

Bleaching Results

| Procedure | Tea on CO | Tea on PES/CO | Red Wine on CO aged | Red Wine on PES/CO aged | Coffee on CO | Coffee on ES/CO | Black Currant Juice on CO | Black Currant Juice on PES/CO | Ave. |
|---|---|---|---|---|---|---|---|---|---|
| 1.5 ml/l Triplex Emulsion + 2.5 ml/l Formula A Conditions: 20' 40° C. | 82.6 | 83.1 | 84.3 | 80.9 | 84.3 | 86.0 | 86.2 | 86.3 | 84.2 |
| 1.5 ml/l Triplex Emulsion + 1 ml/l Ozonit Super Conditions: 10' 70° C. | 78.5 | 79.0 | 82.2 | 82.1 | 84.8 | 86.2 | 86.7 | 86.5 | 83.3 |
| 4 ml/l ³Turbo Usona + 2 ml/l ⁴Ozonit Performance Conditions: 20' 40° C. | 80.8 | 80.5 | 81.5 | 79.0 | 81.1 | 84.2 | 82.0 | 80.8 | 81.2 |
| 4 ml/l Turbo Usona + 4 ml/l ⁵Oxysan Conditions: 20' 40° C. | 79.2 | 77.9 | 78.9 | 76.3 | 79.9 | 83.3 | 77.6 | 75.9 | 78.6 |
| 4 ml/l Turbo Usona + 2 ml/l Formula A Conditions: 15' 40° C. | 82.2 | 81.7 | 82.1 | 80.5 | 82.6 | 85.2 | 82.6 | 82.6 | 82.4 |
| LSD | 1.8 | 3 | 1.9 | 2.4 | 1.1 | 0.8 | 1.7 | 1.8 | 1.9 |

TABLE 8

Bleaching results

| | 1.5 ml/l ²Triplex Emulsion + 1 ml/l Formula A Conditions: 15' 40° C. | 1.5 ml/l Triplex Emulsion + 2 ml/l Formula A Conditions: 15' 40° C. | 1.5 ml/l Triplex Emulsion + 2.5 ml/l Formula A Conditions: 20' 40° C. | 1.5 ml/l Triplex Emulsion + 1 ml/l Ozonit Super Conditions: 10'70° C. | 4 ml/l ³Turbo Usona + 2 ml/l ⁴Ozonit Performance Conditions: 20' 40° C. | 4 ml/l Turbo Usona + 4 ml/l ⁵Oxysan Conditions: 20' 40° C. | 4 ml/l Turbo Usona + 2 ml/l Formula A Conditions: 15' 40° C. | LSD |
|---|---|---|---|---|---|---|---|---|
| Pigment/Lanolin on CO | 54.3 | 55.6 | 56.8 | 67.3 | 57.5 | 56.6 | 54.8 | 6.1 |
| Pigment/Lanolin on PES/CO | 53.4 | 51.4 | 48.8 | 60.6 | 46.1 | 44.9 | 46.2 | 5.8 |
| Pigment/Sebum on CO | 68.3 | 59.7 | 59.6 | 67.5 | 60.1 | 58.0 | 60.9 | 6.7 |
| Pigment/Sebum on PES/CO | 66.0 | 54.2 | 54.7 | 73.4 | 53.2 | 50.5 | 54.3 | 6.3 |
| Soot/Olive Oil on CO | 47.7 | 42.5 | 32.2 | 46.9 | 24.7 | 25.1 | 24.3 | 7.8 |
| Soot/Olive Oil on PES/CO | 33.8 | 28.5 | 24.2 | 38.4 | 15.7 | 14.4 | 13.0 | 9.6 |
| Soot/Min. Oil on CO | 36.9 | 34.3 | 36.0 | 34.0 | 33.4 | 30.6 | 30.6 | 4.5 |
| Soot/Min. Oil on PES/CO | 42.4 | 43.9 | 35.8 | 46.6 | 31.0 | 32.7 | 37.7 | 8.2 |

TABLE 8-continued

Bleaching results

|  | 1.5 ml/l [2]Triplex Emulsion + 1 ml/l Formula A Conditions: 15' 40° C. | 1.5 ml/l Triplex Emulsion + 2 ml/l Formula A Conditions: 15' 40° C. | 1.5 ml/l Triplex Emulsion + 2.5 ml/l Formula A Conditions: 20' 40° C. | 1.5 ml/l Triplex Emulsion + 1 ml/l Ozonit Super Conditions: 10'70° C. | 4 ml/l [3]Turbo Usona + 2 ml/l [4]Ozonit Performance Conditions: 20' 40° C. | 4 ml/l Turbo Usona + 4 ml/l [5]Oxysan Conditions: 20' 40° C. | 4 ml/l Turbo Usona + 2 ml/l Formula A Conditions: 15' 40° C. | LSD |
|---|---|---|---|---|---|---|---|---|
| Used Motor Oil on CO | 42.7 | 43.9 | 42.6 | 46.0 | 44.0 | 44.9 | 46.3 | 2.6 |
| Used Motor Oil on PES/CO | 37.7 | 34.7 | 33.7 | 36.4 | 32.2 | 33.5 | 33.8 | 1.6 |
| Make up on CO | 75.3 | 74.1 | 75.7 | 84.1 | 73.3 | 72.4 | 73.5 | 4 |
| Make up on PES/CO | 79.8 | 77.9 | 76.8 | 86.6 | 75.7 | 74.0 | 76.9 | 3.8 |
| Lipstick on CO | 87.6 | 87.4 | 87.3 | 87.7 | 85.9 | 86.9 | 87.3 | 1.4 |
| Lipstick on PES/CO |  |  |  |  |  |  |  | 3.0470618 |
| Average | 53.2 | 50.1 | 48.1 | 57.3 | 45.6 | 44.8 | 46.0 | 5.6 |

Notes:
1. Y-value refers to a reflectance value calculated by the Minolta CM-2610d Spektrophotometer. It is very similar to the L-value calculated by the Hunter Lab's Spectrophotometers.
[2]Triplex Emulsion is a commercially available all-in-one emulsion of alkaline metal chelators emulsified with a surfactant blend made by Ecolab, Inc. (Europe).
[3]Turbo Usona is a commercially available all-in-one emulsion of alkaline metal chelators emulsified with a surfactant blend made by Ecolab, Inc. (Europe).
[4]Ozonit Super is a Peracetic acid -Hydrogen peroxide bleach disinfectant, made by Ecolab, Inc. (Europe).
[5]Oxysan is a Peracetic acid -Hydrogen peroxide bleach disinfectant which also contains Peroxyoctanoic acid, and is made by Ecolab, Inc. (Europe).
CO: Cotton
PES/CO: Polyester-Cotton blend As can be seen from these results, overall the samples washed with compositions of the present invention, i.e., Formula A, achieved similar bleaching compared with commercially available bleaching agents.

Example 3

Use of a Sulfoperoxycarboxylic Acid as a Bleaching Agent

A bleach test was run comparing a composition including a sulfoperoxycarboxylic acid of the present invention, i.e., 11-sulfoundecaneperoxoic acid (Compound D) with the following commercially available bleaching/cleaning compositions: Tsunami 100®, available from Ecolab Inc.; Oxonia Active®, available from Ecolab Inc.; hydrogen peroxide (35%); and PAP-70®, available from Solvay. These chemistries were used as is except for pH adjustments to pH 8 using sodium bicarbonate, and pH 12 by the addition of sodium hydroxide, in 5 grain hard water.

Fabric swatches soiled with tea, blood, or wine were used for this example. The soil swatches were washed using the same experimental procedure described above in Example 2. However, for this example, the soil swatches were washed for 10 minutes at 120° F. The pH of the wash solution for all samples was about 9. The percent soil removal (SR) was determined according to the method described above in Example 2. The following table shows the results of this study.

TABLE 9

| Bleach Type | pH | Temp(F.) | Wash Time (min) | % SR | Bleach mg/L use solution | Use Solution Available Oxygen (ppm) |
|---|---|---|---|---|---|---|
| Removal of Tea Stains | | | | | | |
| Composition Including Compound D | 9 | 120 | 10 | 37 | 1350 | 56 |
| Tsunami 100 ® | 9 | 120 | 10 | 34 | 770 | 56 |
| Oxonia Active ® | 9 | 120 | 10 | 27 | 410 | 56 |
| $H_2O_2$ (35%) | 9 | 120 | 10 | 24 | 340 | 56 |
| PAP-70 | 9 | 120 | 10 | 63 | 1386 | 56 |
| Water (control) | 9 | 120 | 10 | 11 | 0 | 56 |
| Removal of Blood Stains | | | | | | |
| Composition Including Compound D | 9 | 120 | 10 | 90 | 1350 | 56 |
| Tsunami 100 ® | 9 | 120 | 10 | 81 | 770 | 56 |
| Oxonia Active ® | 9 | 120 | 10 | 80 | 410 | 56 |
| $H_2O_2$ (35%) | 9 | 120 | 10 | 82 | 340 | 56 |
| PAP-70 | 9 | 120 | 10 | 88 | 1386 | 56 |
| Water (control) | 9 | 120 | 10 | 36 | 0 | 0 |
| Removal of Red Wine Stains | | | | | | |
| Composition including Compound D | 9 | 120 | 10 | 62 | 1350 | 56 |
| Tsunami 100 ® | 9 | 120 | 10 | 57 | 770 | 56 |
| Oxonia Active ® | 9 | 120 | 10 | 41 | 410 | 56 |
| $H_2O_2$ (35%) | 9 | 120 | 10 | 45 | 340 | 56 |

TABLE 9-continued

| Bleach Type | pH | Temp(F.) | Wash Time (min) | % SR | Bleach mg/L use solution | Use Solution Available Oxygen (ppm) |
|---|---|---|---|---|---|---|
| PAP-70 | 9 | 120 | 10 | 74 | 1386 | 56 |
| Water (control) | 9 | 120 | 10 | 36 | 0 | 56 |

As can be seen from this table, with respect to tea stains, the PAP-70® composition achieved the greatest soil removal. The composition containing a compound of the present invention achieved the next highest percent soil removal. With respect to blood stains, the composition containing the sulfoperoxycarboxylic acid of the present invention achieved the greatest soil removal. However, all concentrated oxidizers performed well in removing the blood stains. With respect to the red wine stains, the sulfoperoxycarboxylic acid of the present invention performed well compared to the PAP-70®.

Example 4

Stability Studies

The stability of a sulfoperoxycarboxylic acid of the present invention, i.e., 11-sulfoundecaneperoxoic acid (Compound D), was compared to that of phthalimidoperoxyhexanoic acid (PAP). The stability data for the PAP sample were taken from U.S. Pat. No. 5,994,284, assigned to Clariant GmbH. Samples of the compound of the present invention were stored for four (4) weeks at various temperatures. The loss of active oxygen was measured by titrimetry. The results are shown in the table below.

TABLE 10

| Compound | Storage Time (weeks) | Temperature (° C.) | Loss of Active Oxygen (%) |
|---|---|---|---|
| Compound D | 4 | Room Temp. | 0.78 |
| Compound D | 4 | 38 | 7.9 |
| Compound D | 4 | 50 | 15.7 |
| PAP | 4 | 25 | 1.4 |
| PAP | 4 | 40 | 2.0 |
| PAP | 4 | 50 | 12.0 |

As can be seen from this table, the compound of the present invention was more stable, i.e., lost less active oxygen, at room temperature, i.e., about 23° C., than the PAP at 25° C.

Example 5

Bleaching Performance of Various Formulas of the Present Invention

A test was run to compare the bleaching properties of compositions of the present invention with the following commercially available bleaching agents: Ozonit®, available from Ecolab Inc.; and PAP®, available from Clariant. The following compositions of the present invention were used: Formula A, which included about 25 wt % of the sulfonated peroleic acid product, about 70 wt % $H_2O_2$ (35%), and about 5 wt % HEDP 60; Formula B which included about 24 wt % of a mixture of the sulfonated peroleic acid product and peroxyoctanoic acid, about 72 wt % $H_2O_2$ (35%), and about 4 wt % HEDP 60; and Formula C which included about 20 wt % of a mixture of the sulfonated peroleic acid product and peroxyoctanoic acid, about 62 wt % $H_2O_2$ (35%), about 4 wt % HEDP 60, and about 13 wt % acetic acid. These formulas were compared with the commercially available bleaching agents at 40° C. at a pH of between 7 to 8. The Ozonit® was also tested at 60° C.

Figure 4:
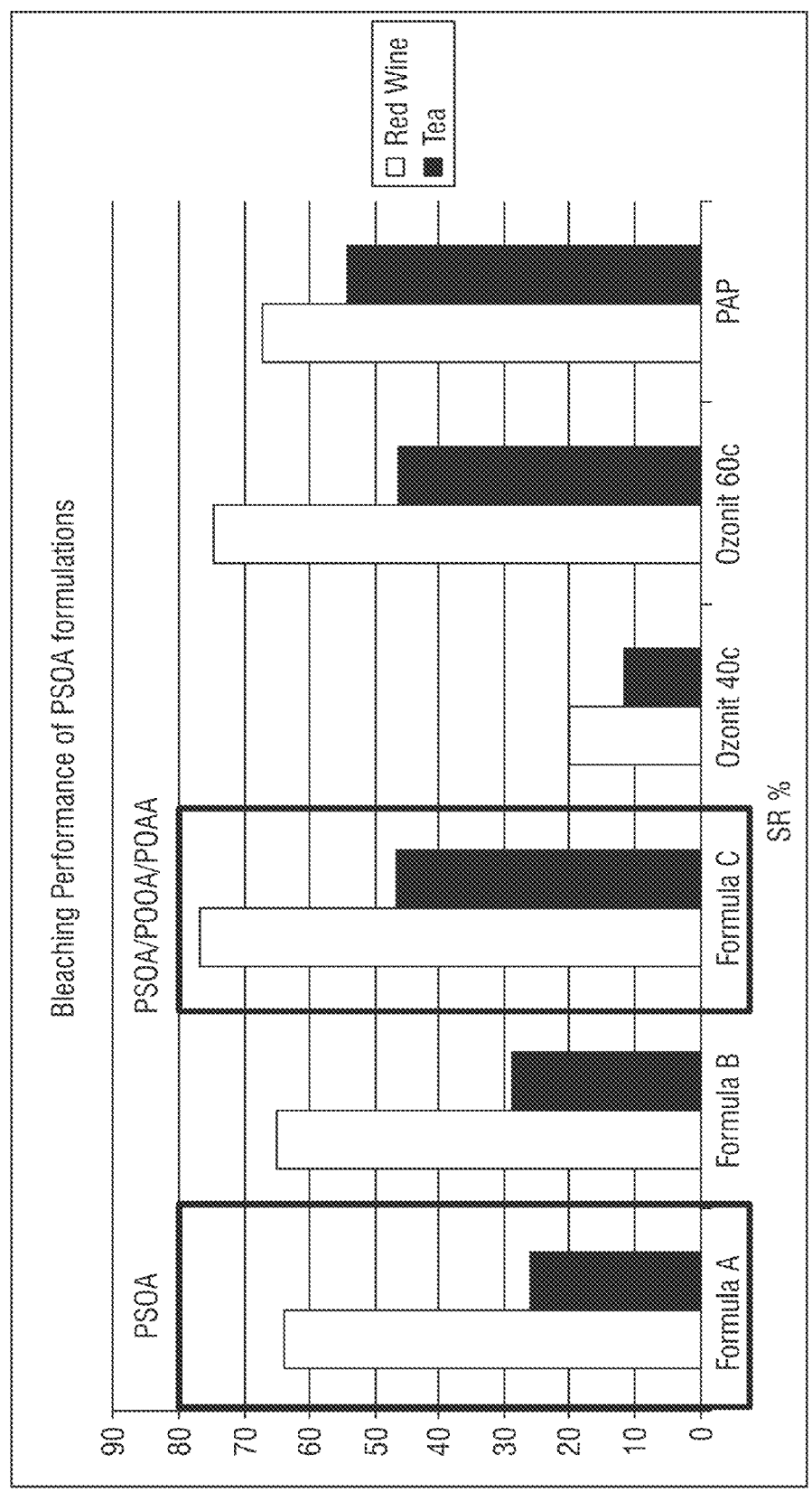
FIG. 4 is a graphical depiction of the bleaching performance of compositions of the present invention compared to commercially available bleaching agents.

To measure the bleaching ability of the formulations, a bleaching test as described in Example 2 was performed. The results are shown in FIG. 4. As can be seen in this figure, Formulas A, B and C had far superior bleaching ability compared to Ozonit® at 40° C. When the Ozonit® was used at 60° C., Formulas A, B, and C had very similar bleaching ability. Formula C also had similar bleaching performance compared to the PAP. Thus, Formulas A, B, and C showed equal, if not better, bleaching properties compared to known commercially available bleaching agents at 40° C.

Example 6

Antimicrobial Studies (a) Bactericidal Efficacy

An experiment was performed to determine the bactericidal efficacy of a composition according to the present invention, with and without a surfactant, as compared to other commercially available products. Formula A included about 1190 ppm of a sulfonated peroleic acid product, as well as peroxyoctanoic acid, and peracetic acid. The surfactant used for this example was Turboemulsion® (TE), commercially available from Ecolab Inc. The compositions were tested against *Clostridium difficile* ATCC 9689, MRSA ATCC 33592, *Enterococcus hirae* ATCC 10541, *Escheria coli* ATCC 11229, and *Pseudomonas aeruginosa* ATCC 15442, at 5 and 60 minute exposure times. The commercially available compositions, Ozonit®, and PAP were also tested. The following formulations were tested:

TABLE 11

| Test Formulation | Desired Concentration of Active Agent | Diluent | Test Use Solution (Volume of Test Substance/Total Volume) | pH |
|---|---|---|---|---|
| Formula A with surfactant | 1190 ppm | Sterile MilliQ Water | 0.194 g Formula A + 170 µL TE/100 g | 7.59 |
| Formula A without Surfactant | 1190 ppm | | 0.194 g Formula A/ 100 g | 8.53 |
| PAP ® | 1820 ppm | | 0.182 g PAP + 1.5 g TE/100 g | 8.50 |
| Ozonit ® | 2000 | | 0.200 g Ozonit + 1.5 g TE/100 g | 7.21 |

The test method followed was according to European Standard EN 13704: *Quantitative Suspension Test for the Evaluation of Sporicidal Activity of Chemical Disinfectants and Antiseptics Used in Food, Industrial, Domestic and Institutional Areas*. Generally, a test suspension of bacterial spores in a solution of interfering substance, simulating clean conditions, was added to a prepared sample of the test formulation diluted in hard water. The mixture was maintained at the specific temperature and time desired. At this contact time, an aliquot is taken; the sporicidal action in this portion was immediately neutralized or suppressed by a validated method. The number of surviving bacterial spores in each sample was determined and the reduction in viable counts was calculated.

The disinfectant properties of each of the formulations at 5 minutes at 40° C. are shown below in Table 12.

TABLE 12

| | System | | | |
|---|---|---|---|---|
| Test | Formula A with Surfactant | PAP | Ozonit | Formula A without Surfactant |
| MRSA | >6.66 | >6.66 | >6.66 | >6.66 |
| Enterococcus hirae ATCC 10541 | >6.26 | >6.26 | >6.26 | >6.26 |
| Escherichia coli ATCC 11229 | >6.74 | >6.74 | >6.74 | >6.74 |
| Pseudomonas aeruginosa ATCC 15442 | >6.32 | >6.32 | >6.32 | >6.32 |
| Clostridium difficile ATCC 9689 | >3.87 | 1.17 | 2.57 | 3.09 |

As can be seen from this table, the compositions of the present invention that were tested were as effective as a disinfectant as the commercially available formulations tested. Further, with respect to *Clostridium difficile*, the compositions of the present invention were more effective than the commercially available products tested.

(b) Stability and Sporicidal Efficacy at 14 Days

A test was run to determine the stability and sporicidal efficacy of a composition of the present invention against spores. The composition tested included the sulfonated peroleic acid product, and an amount of peroxyoctanoic acid. The test method used was the European Standard EN 13704: *Quantitative Suspension Test for the Evaluation of Sporicidal Activity of Chemical Disinfectants and Antiseptics Used in Food, Industrial, Domestic and Institutional Areas*, described above. The table below shows the results of this study.

TABLE 13

Sulfonated Peroleic Acid Product + POOA (14 day Retention)

DI Water
pH 6.5

| B. subtilis | C. difficile |
|---|---|
| Clean Conditions 20° C. | |
| 60 min | 60 min |
| Log reduction 3.84 | Log reduction 2.71 |

A composition including 30 ppm peroxyoctanoic acid was also tested. The composition of peroxyoctanoic acid alone did not result in a reduction.

Figure 5:
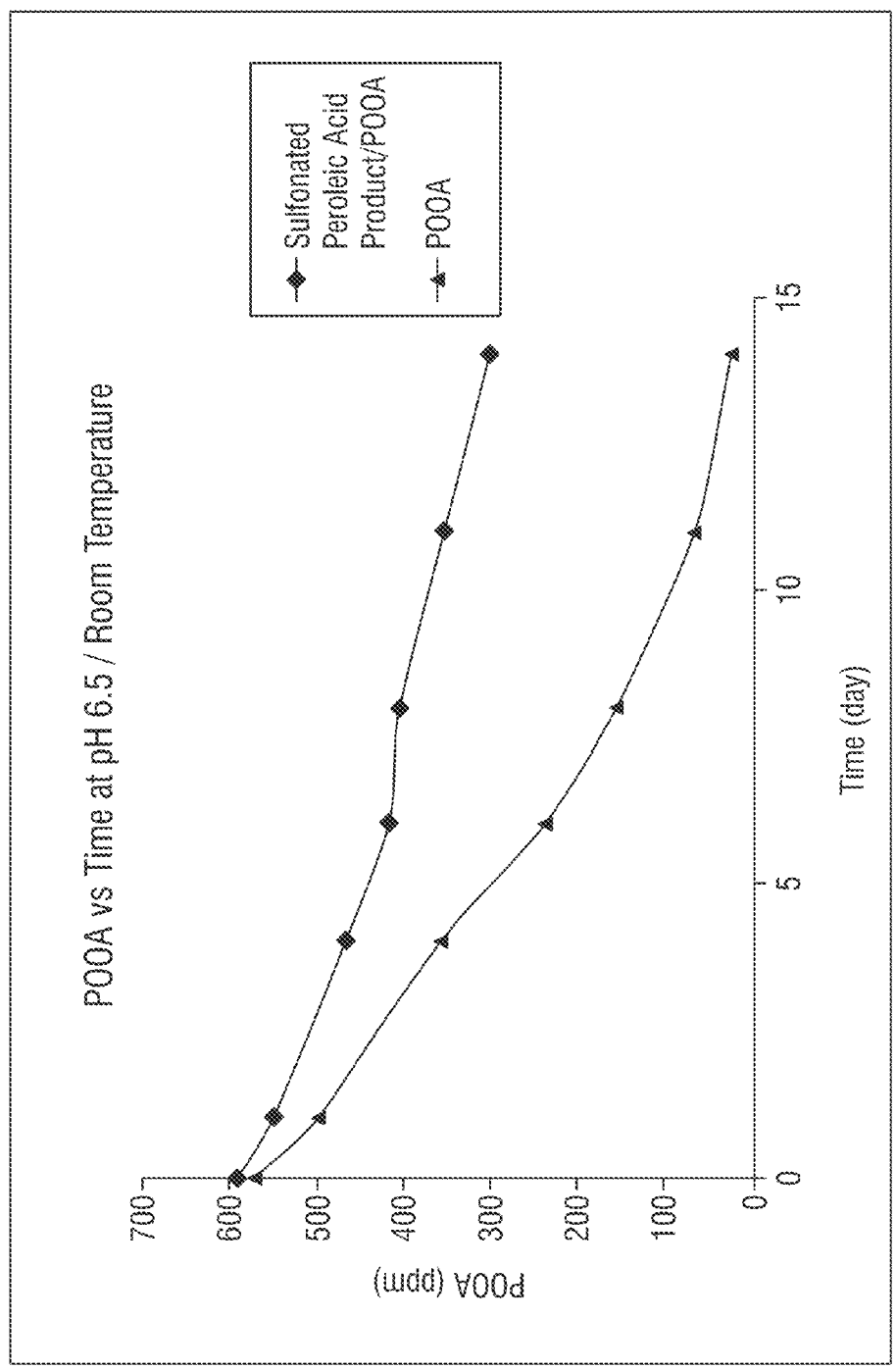
FIG. 5 is a graphical depiction of the stability profile of peroxyoctanoic acid in combination with exemplary compositions of the present invention.

FIG. 5 shows the stability impact that the compound of the present invention used, i.e., the sulfonated peroleic acid product, had on the amount of POOA over time during this study. As can be seen from this figure, the amount of POOA available over time was higher with the sample of POOA that was stabilized using a composition of the present invention, compared to a sample of POOA that was not stabilized using a composition of the present invention.

(c) Synergistic Effect of a Composition of the Present Invention with a Known Sanitizer For this study, the ASME 1052-96: Standard Test Method for Efficacy of Antimicrobial Agents against Viruses in Suspension was used. A composition including 1000 ppm peroxyacetic acid (POAA) was tested alone, and in combination with sulfonated peroleic acid product.

The POAA solution alone did not display complete inactivation of Poliovirus Type 1 after an exposure time of four minutes. The reductions in viral titer were ≤0.75 and ≤0.50 log 10. When the POAA solution was tested with 1000 ppm of the sulfonated peroleic acid product, the solution displayed complete inactivation of Poliovirus Type 1 after an exposure time of a few minutes, and was therefore efficacious against the virus. The reduction in viral titer was ≥5.75 log 10.

(d) Synergistic Effect of a Compound of the Present Invention with Peroxyoctanoic Acid For this study, the MS 103: Quantitative Tuberculocidal Test was used. The sulfonated peroleic acid product was tested alone, and in combination with peroxyoctanoic acid at various concentrations against *Mycobacterium bovis* BCG. The compositions were tested at a pH of 6.5 at room temperature. The results are shown in the table below.

TABLE 14

| Test Substance | Exposure Time | Log Reduction |
|---|---|---|
| 1000 ppm Sulfonated Peroleic | 2.5 min | 4.46 |
| Acid Product | 5 min | 5.11 |
| 300 ppm POOA | 2.5 min | 3.48 |
| | 5 min | <4.31 |
| 1000 ppm Sulfonated Peroleic | 2.5 min | >7.31 |
| Acid Product and 300 ppm POOA | 5 min | >7.31 |
| 1000 ppm Sulfonated Peroleic | 2.5 min | ≥7.31 |
| Acid Product and 150 ppm POOA | 5 min | >7.31 |

As can be seen from this table, the samples treated with both a composition of the present invention including the sulfonated peroleic acid product, and POOA had a higher log reduction of *Mycobacterium bovis* BCG than those samples treated with either the sulfonated peroleic acid product or POOA alone. Although it was found that the samples treated with just the sulfonated peroleic acid product did have a higher log reduction of bacteria than the samples treated with just POOA.

(e) Use of a Compound of the Invention as a Hospital Disinfectant

For this test, the AOAC Official Method 955.15—Testing Disinfectant Against *Staphylococcus aureus* and the AOAC Official Method 964.02—Testing Disinfectants Against *Pseudomonas aeruginosa* were used. The composition used included the sulfonated peroleic acid product, and peroxyoctanoic acid (POOA), at various concentrations. The following chart summarizes the test procedure used, and the results.

TABLE 15

| Test Substance | Desired Concentration | Diluent | Dilution (Volume of Test System/ Total Volume) | Test pH |
|---|---|---|---|---|
| Sulfonated Peroleic Acid Product + POOA | 1000 ppm Sulfonated Peroleic Acid Product 300 ppm POOA | 400 ppm Synthetic Hard Water | 2.910 g Sulfonated Peroleic Acid Product + 0.2345 g POOA/1500 g | 6.5 |
| | 1000 ppm Sulfonated Peroleic Acid Product 150 ppm POOA | | 0.1852 g Sulfonated Peroleic Acid Product + 0.4690 g POOA/1500 g | 6.5 |

TABLE 15-continued

| Test system | Test Substance | # Negative Tubes/# Carriers Tested |
|---|---|---|
| *Staphylococcus aureus* ATCC 6538 | 1000 ppm Sulfonated Peroleic Acid Product + 300 ppm POOA | 60/60 |
| *Staphylococcus aureus* ATCC 6538 | 1000 ppm Sulfonated Peroleic Acid Product + 150 ppm POOA | 60/60 |
| *Pseudomonas aeruginosa* ATCC 15442 | 1000 ppm Sulfonated Peroleic Acid Product + 300 ppm POOA | 60/60 |
| *Pseudomonas aeruginosa* ATCC 15442 | 1000 ppm Sulfonated Peroleic Acid Product + 150 ppm POOA | 60/60 |

As can be seen from this table, the compositions tested were effective against each of the test systems.

Example 7

Coupling Abilities of Compounds of the Present Invention

The ability of a composition of the present invention including the sulfonated peroleic acid product to couple octanoic acid was compared to the coupling abilities of two known commercially available coupling agents, NAS and linear alkylbenzene sulphonate (LAS).

Figure 6:
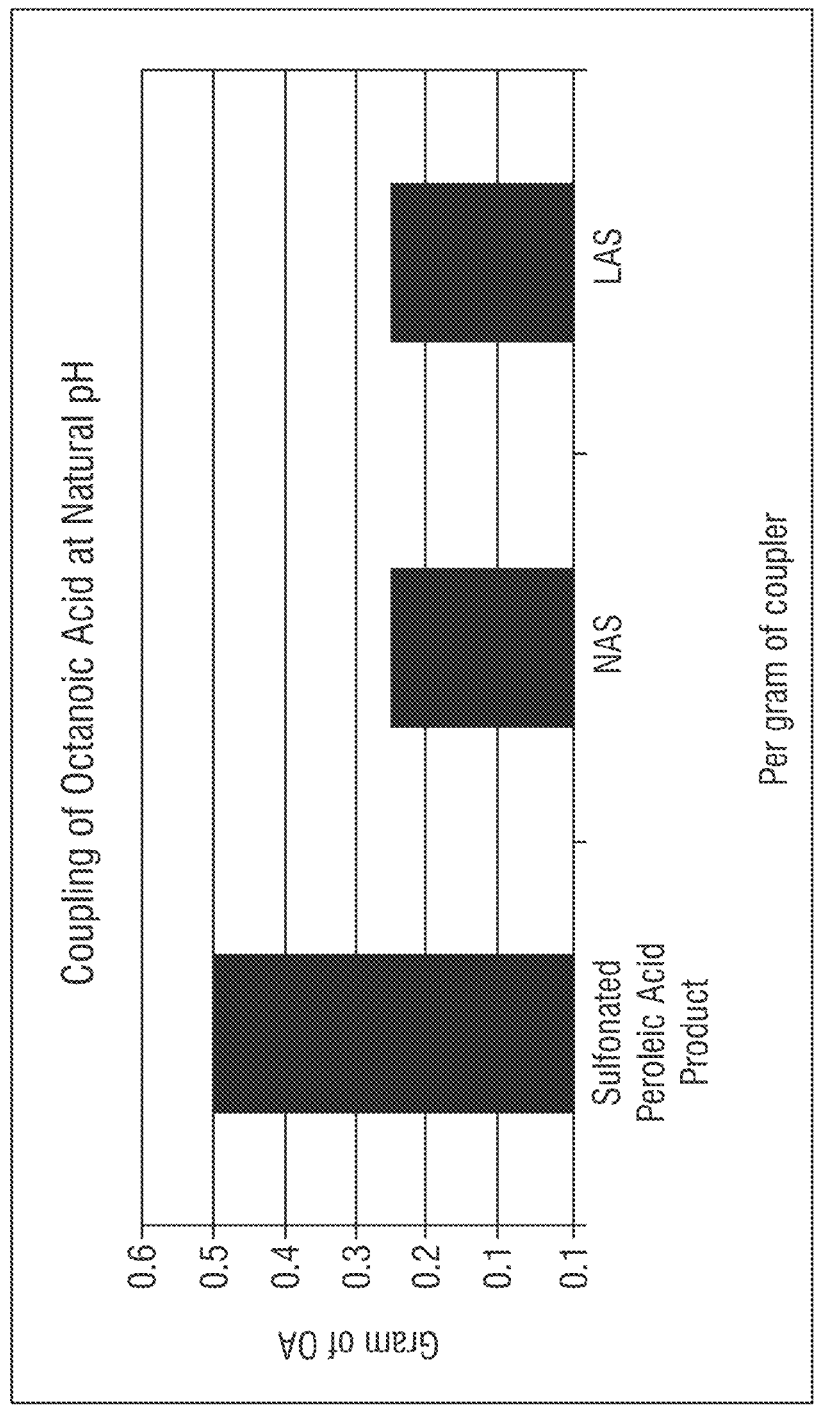
FIG. 6 is a graphical depiction of the coupling capabilities of a selected composition of the present invention.

The results can be seen in FIG. 6. As can be seen from this figure, one gram of the sulfonated peroleic acid product was able to couple twice as much octanoic acid compared to the other coupling agents tested.

Example 8

Formation of Sulfonated Carboxylic Acids and their Percarboxylic Salts

A study was run to determine the effect of the position of the sulfonate group on the carboxylic acid in forming a peracid. Specifically, a study was run to determine whether having the sulfonate group at the α position prohibits the oxidation and/or perhydrolysis of the carboxylic acid group to form the corresponding peroxycarboxylic acid.

Commercially available sulfonated fatty acid salts (methyl esters) are predominantly α sulfonated, including, for example, Alpha-Step PC-48 (commercially available from the Stepan Comp.), Alpha-Step MC-48 (MC-48)(commercially available from the Stepan Comp.), Alpha-Step BSS-45 (commercially available from the Stepan Comp.), and MES (commercially available from the Lion Corporation). Structurally, these compounds are sodium alphasulfo methyl $C_{12}$-$C_{18}$ esters and disodium alphasulfo $C_{12}$-$C_{18}$ fatty acid salts. Their structures are shown below:

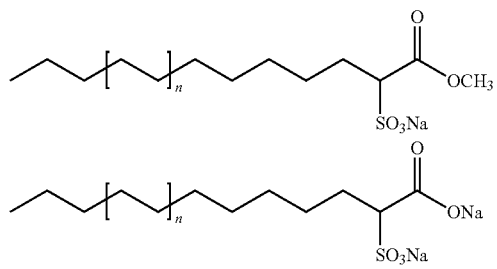

Sulfonated oleic acid is another commercially available sulfonated fatty acid. These compounds are mainly 8-sulfo-octadecenoic acid salts, with a minority of 9-sulfo-10-hydroxy-octadecanoic acid salts. They are not sulfonated at the α position. The structures of these types of compounds are shown below:

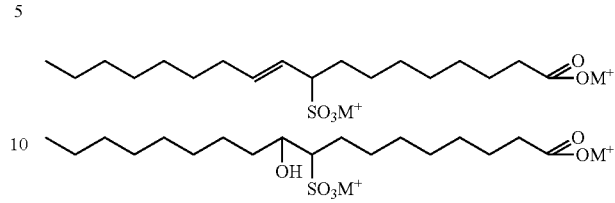

α-sulfonated fatty acids were prepared by the hydrolysis of the mixture of α-sulfonated fatty acid methyl ester and the acid (MC-48). To a beaker containing 25 g of MC-48, 12 g of 50% NaOH solution was added. The mixture was stirred at ambient temperatures for 3 hours. The mixture was then acidified by adding $H_2SO_4$ (50%) until the pH of the mixture reached about 0-1. The white solid precipitate was filtered, washed with cold water, and dried. The white solid powder yield was evaluated using $^{13}$C NMR (DMSO-$d_6$). The methyl group of the methyl ester in the raw material was not observed, indicating complete hydrolysis.

In order to try and form the peracid using an acid catalyzed hydroxide reaction the following reaction was performed. 0.5 g of the MC-48 derived fatty acid sulfonate, as prepared above, was weighed into a 50 ml beaker. To this beaker, 30 g of $H_2O_2$ (35%) was added. then, 5 g of $H_2SO_4$ (985) was slowly added, producing a clear solution. After sitting at 50° C. for 24 hours, the solution was analyzed to determine the presence of a peracid.

To determine the presence of a peracid, a kinetic iodometric titration similar to the method disclosed in Sully and Williams ("The Analysis of Per-Acids and Hydrogen Peroxide," *The Analyst*, 87:1037, p. 653 (August 1962)) was used. This method has demonstrated a lower detection limit of about 0.3 ppm for POAA. Given the molecular weight ratio of POAA to the perspective percarboxylic acid of PC-48, the detection limit was estimated to be about 1.4 ppm ($3.93 \times 10^{-6}$ M). No peracid formation was observed. This is equivalent to a percarboxylic acid formation constant (Keq) less than 0.002, suggesting substantially no peracid was formed.

Alternatively, formation of the peracid was determined using $^{13}$C NMR ($D_2O$). Using this technique, no carbonyl resonance signal from the peracid was observed.

Other α-sulfonated fatty acid sources such as Alpha-Step PC-48 and Alpha-Step BSS-45 were also reacted with $H_2O_2$ in a similar manner, and in both cases, no corresponding peracids were detected.

Non-α-sulfonated fatty acids were also tested to determine the likelihood of peracid formation. For the sulfonated oleic acid discussed above, the measured formation constant was 1.42. The sulfonated undecenoic acid was collected as a stable solid powder, so the formation constant was not measured. Although the formation constant of the peracid of sulfonated oleic acid is significantly lower than that of the most common commercialized peracid, peroxyacetic acid (Keq=2.70), it is still high enough to make practical yields.

Overall, without wishing to be bound by any particular theory, it is thought that the α-sulfo group prohibits the oxidation and/or perhydrolysis of the carboxylic acid group by $H_2O_2$ to the corresponding peracid. This may in part be due to its strong electron withdrawing effects.

Example 9

Clean in Place Sanitizing Compositions

A study was run to determine the efficacy of compositions of the present invention as sanitizers used in a clean in place cleaning method. A composition including about 5.85 wt % of the sulfonated peroleic acid product, and about 11.6% hydrogen peroxide, about 1 wt % of a chelating agent, about 12.75 wt % of $H_2SO_4$, about 13.6 wt % NAS-FAL (sodium octane sulfonate), and about 1.5 wt % of SXS (commercially available from the Stepan Company) was prepared. Synthetic hard water was used to dilute the test composition to the desired peracid concentration. The peracid was tested at concentrations of 1000 ppm, 750 ppm and 500 ppm. The pH of the use solutions were as follows:

| Concentration of Peracid in Use Solution | pH |
|---|---|
| 500 ppm peracid | 1.65 |
| 750 ppm | 1.46 |
| 1000 ppm | 1.38 |

The use solutions were tested against *Staphylococcus aureus* ATCC 6538 and *Pseudomonas aeruginosa* ATCC 15442. The organic soil used was 5% Fetal Bovine Serum. The exposure time of the test was 5 minutes at a temperature of 20±1° C. A neutralizer screen was also performed as part of the testing to verify that the neutralizer adequately neutralized the product and was not detrimental to the tested organisms. The plates were incubated at 35° C. for 48 hours with the test systems prior to exposure to the peracids. The results are shown in the table below.

TABLE 16

| Test Substance | # Negative Tubes/# Carriers Tested |
|---|---|
| *Staphylococcus aureus* ATCC 6538 | |
| 1000 ppm Peracid Composition | 60/60 |
| *Pseudomonas aeruginosa* ATCC 15442 | |
| 1000 ppm Peracid Composition | 60/60 |

| Test Controls | | |
|---|---|---|
| Control | Test System | Results |
| Negative Carrier | | 1 negative of 1 tested |
| Positive Carrier | *Staphylococcus aureus* ATCC 6538 | 1 positive of 1 tested |
| Positive Carrier | *Pseudomonas aeruginosa* ATCC 15442 | 1 positive of 1 tested |
| Organic Soil | | 1 negative of 1 tested |
| Neutralization (1000 ppm) | *Staphylococcus aureus* ATCC 6538 | 6 positive of 6 tested |
| Neutralization (1000 ppm) | *Pseudomonas aeruginosa* ATCC 15442 | 6 positive of 6 tested |
| Culture Enumeration | *Staphylococcus aureus* ATCC 6538 | $9.0 \times 10^8$ CFU/mL |
| Culture Enumeration | *Pseudomonas aeruginosa* ATCC 15442 | $1.0 \times 10^9$ CFU/mL |
| Carrier Enumeration | *Staphylococcus aureus* ATCC 6538 | $1.0 \times 10^6$ CFU/mL $1.0 \times 10^7$ CFU/Carrier |
| Carrier Enumeration | *Pseudomonas aeruginosa* ATCC 15442 | $2.3 \times 10^6$ CFU/mL $2.3 \times 10^7$ CFU/Carrier |

| Test Substance | # Negative Tubes/# Carriers Tested |
|---|---|
| *Staphylococcus aureus* ATCC 6538 | |
| 500 ppm Peracid Composition | 59/60 |
| 750 ppm Peracid Composition | 60/60 |
| *Pseudomonas aeruginosa* ATCC 15442 | |
| 500 ppm Peracid Composition | 58/60 |
| 750 ppm Peracid Composition | 60/60 |

| Test Controls | | |
|---|---|---|
| Control | Test System | Results |
| Negative Carrier | | 1 negative of 1 tested |
| Positive Carrier | *Staphylococcus aureus* ATCC 6538 | 1 positive of 1 tested |
| Positive Carrier | *Pseudomonas aeruginosa* ATCC 15442 | 1 positive of 1 tested |
| Organic Soil | | 1 negative of 1 tested |
| Neutralization | *Staphylococcus aureus* ATCC 6538 | 3 positive of 3 tested |
| Neutralization | *Pseudomonas aeruginosa* ATCC 15442 | 3 positive of 3 tested |
| Culture Enumeration | *Staphylococcus aureus* ATCC 6538 | $1.0 \times 10^9$ CFU/mL |
| Culture Enumeration | *Pseudomonas aeruginosa* ATCC 15442 | $1.0 \times 10^9$ CFU/mL |
| Carrier Enumeration | *Staphylococcus aureus* ATCC 6538 | $7.2 \times 10^5$ CFU/mL $7.2 \times 10^6$ CFU/Carrier |
| Carrier Enumeration | *Pseudomonas aeruginosa* ATCC 15442 | $2.0 \times 10^6$ CFU/mL $2.0 \times 10^7$ CFU/Carrier |

As can be seen from these results, the use solutions tested were effective disinfectants against both *Staphylococcus aureus*, and *Pseudomonas aeruginosa* at the concentrations tested.

Another study was run to determine the sanitizing efficacy of the test solution against *Staphylococcus aureus* ATCC 6538 and *Escherichia coli* ATCC 11229 after a 30 second exposure time. For this experiment the solutions were diluted to have a concentration of 50 ppm, 75 ppm or 100 ppm of the sulfonated peroleic acid product. The pH of the use solutions were as follows:

| Concentration of Peracid in Use Solution | pH |
|---|---|
| 50 ppm peracid | 2.70 |
| 75 ppm | 2.47 |
| 100 ppm | 2.30 |

The use solutions were tested against *Staphylococcus aureus* ATCC 6538 and *Escherichia coli* ATCC 11229. The exposure time was 30 seconds at a temperature of 25±1° C. A neutralizer screen was also performed as part of the testing to verify that the neutralizer adequately neutralized the product and was not detrimental to the tested organisms. The plates were incubated at 35° C. for 48 hours with the test systems prior to exposure to the peracids. The results are shown in the table below.

TABLE 17

| Test System | CFU/mL | $Log_{10}$ Growth | Average $Log_{10}$ Growth |
|---|---|---|---|
| Inoculum Numbers | | | |
| *Staphylococcus aureus* ATCC 6538 | $107 \times 10^6$, $109 \times 10^6$ | 8.03, 8.04 | 8.04 |
| *Escherichia coli* ATCC 11229 | $138 \times 10^6$, $151 \times 10^6$ | 8.14, 8.18 | 8.16 |

| Test Substance | Survivors (CFU/mL) | $Log_{10}$ Growth | Average $Log_{10}$ Growth | Log Reduction |
|---|---|---|---|---|
| *Staphylococcus aureus* ATCC 6538 | | | | |
| 50 ppm Peracid Composition | $28 \times 10^1$, $20 \times 10^1$ | 2.45, 2.30 | 2.38 | 5.66 |
| 75 ppm Peracid Composition | $0 \times 10^1$, $100 \times 10^1$ | <1.00, 3.00 | <2.00 | >6.04 |
| 100 ppm Peracid Composition | $0 \times 10^1$, $0 \times 10^1$ | <1.00, <1.00 | <1.00 | >7.04 |
| *Escherichia coli* ATCC 11229 | | | | |
| 50 ppm Peracid Composition | $0 \times 10^1$, $2 \times 10^1$ | <1.00, 1.30 | <1.15 | >7.01 |
| 75 ppm Peracid Composition | $0 \times 10^1$, $0 \times 10^1$ | <1.00, <1.00 | <1.00 | >7.16 |
| 100 ppm Peracid Composition | $0 \times 10^1$, $0 \times 10^1$ | <1.00, <1.00 | <1.00 | >7.16 |

As can be seen from these results the use solutions tested were effective sanitizers against both *Staphylococcus aureus* and *Escherichia coli*. The test solution containing 100 ppm of the sulfonated peroleic acid product was the most effective sanitizer.

Example 10

Foam Properties of Selected Compositions of the Present Invention

A study was performed to determine the foam properties of selected compositions of the present invention, compared to compositions including commercially available surfactants. The following compositions were prepared: Formula A included 50 ppm of the sulfonated peroleic acid product at a pH of 2.48; Formula B included 50 ppm of the sulfonated peroleic acid product at a pH6.75; Formula C included 64 ppm of a commercially available sulfonated oleic acid (SOA)(Lankropol OPA (50%) available from Akzo Nobel) at a pH of 2.48; Formula D included 64 ppm of a commercially available sulfonated oleic acid (Lankropol OPA (50%) available from Akzo Nobel) at a pH of 6.56; Formula E included 128 ppm of a commercially available sulfonated oleic acid (Lankropol OPA (50%) available from Akzo Nobel) at a pH of 2.48; Formula F included 128 ppm of a commercially available sulfonated oleic acid (Lankropol OPA (50%) available from Akzo Nobel) at a pH of 7.20; and Formula G included 93 ppm of sodium octane sulfonate (NAS) (commercially available from Ecolab) at a pH of 2.48. The foam heights were determined using the following method. First 3000 ml of each formula was prepared and gently poured into Glewwe cylinder. A ruler was attached to the side of the cylinder, and the solution was level with the bottom of the ruler. The pump was turned on. Foam height was estimated by reading the average level of foaming according to the ruler. Foam height readings were taken versus time with a stopwatch or timer. The pump was turned off and height of the foam was recorded at various times. The results are shown in the table below.

TABLE 18

| | Pump On Time (sec) | | | Pump Off Time (sec) | | |
|---|---|---|---|---|---|---|
| Sample | 30 Foam Height (inches) | 60 Foam Height (inches) | 300 Foam Height (inches) | 30 Foam Height (inches) | 60 Foam Height (inches) | 300 Foam Height (inches) |
| Formula A | 2.5 | 3.8 | 5.5 | 3.5 | 2.0 | 0.5 |
| Formula B | 1.5 | 2.0 | 2.5 | 0.2 | <0.1 | NA |
| Formula C | 4.0 | 6.2 | 9.2 | 8.7 | 8.5 | 5.5 |
| Formula D | 3.1 | 4.5 | 10 | 9.8 | 8.5 | 4.0 |
| Formula E | 2.6 | 4.5 | 8.5 | 8.2 | 8.0 | 5.0 |
| Formula F | 0.15 | 0.15 | 0.2 | <0.1 | <0.1 | <0.1 |
| Formula G | 1.0 | 1.0 | 1.2 | 0.4 | 0.2 | <0.1 |

As can be seen from these results, the formulas including compositions of the present invention, i.e., Formulas A and B had much lower foam heights than Formulas C and D which included the non-peracid form of the sulfonated material, i.e., sulfonated oleic acid. The reduced foam height of the compositions of the present invention is useful when using the compositions in applications where the production of foam is detrimental to the application, for example, in a clean in place cleaning and/or sanitizing application.

Example 11

Laundry Sanitizing Compositions

A study was run to determine the ability of a composition of the present invention to sanitize laundry. A composition containing the sulfonated peroleic acid product was tested against the commercially available cleaning compositions Ozonit®, commercially available from Ecolab Inc., and PAP-70®, available from Solvay. The compositions were tested against *Staphylococcus aureus* ATCC 6538 and *Pseudomonas aeruginosa* ATCC 15442 at 104° F. for 6 minutes. The test method was as follows. Fabric samples that had been rinsed with boiling water containing 300 grams sodium carbonate and 1.5 grams of a non-ionic wetting agent (e.g., Triton X-100), followed by a cold water rinse until all visible traces of the wetting agent were removed, were obtained. The fabric samples were allowed to completely dry. The fabric samples were then autoclaved to sterilize them.

The test substances were then prepared, and the fabric samples were inoculated with the test substances. The inoculated swatches were then dried. The samples were then secured in a laundrometer and agitated in wash water. The wash water was removed from the chamber of the laundrometer, and the wash water and fabric samples are evaluated for the reduction of the tested microorganism population.

The results are shown in the table below.

TABLE 19

| | System | | |
|---|---|---|---|
| Test | Composition including Sulfonated Peroleic Acid Product | PAP-70 ® | Ozonit ® |
| Sanitizer Screen | >3.82 | >3.82 | NA |
| Disinfectant (Cloth Carrier Screen) | 9 negative/ 9 total | 9 negative/ 9 total | 5 negative/ 9 total |

As can be seen from these results, both the composition of the present invention tested showed a greater than 3 log reduction in both the wash water and fabric carriers against *P. aeruginosa* and on the fabric carriers against *S. aureus*.

The present invention also relates to novel compounds and the synthesis thereof. Accordingly, the following examples are presented to illustrate how some of those compounds may be prepared.

Example 12

Stability Study

A study was performed to determine the stability of various sulfonated peracids in aqueous solutions. The sulfonated peracids were compared under the same controlled conditions to determine how the structural differences of the selected peracids impacted stability. The sulfonated peracids studied included both mid-chain sulfonated and terminally sulfonated peracids.

Each peracid was tested at a concentration of 50 ppm under ambient conditions. Each individual solution was prepared from the corresponding peracid concentrate by adding it to a 0.05 M pH 5.0 citrate buffer, and adjusting the final solution pH to 5.0 with the addition of a small amount of caustic. The terminally sulfonated peracids studied are shown in the table below.

| Name | Structure |
|---|---|
| 2-Sulfoperoxyacetic acid (2-SPOAA) | $HO_3S-CH_2-C(=O)-O-OH$ |
| 5-sulfoperoxyheptanoic acid (5-SPOHA) | $HO_3S-(CH_2)_3-C(=O)-O-OH$ |
| 6-sulfoperoxyhexanoic acid (6-SPOHXA) | $HO_3S-(CH_2)_5-C(=O)-O-OH$ |

| Name | Structure |
|---|---|
| 11-sulfoperoxyundecanoic acid (11-SPOUA) | $HO_3S$—(CH$_2$)$_{10}$—C(=O)—O—OH |

The above terminally sulfonated peracids were compared to the mid-chain sulfonated peracid, persulfonated oleic acid product (PSOA), described above.

It should be noted however, that the precursor for the 11-SPOUA, viz. 11-sulfoundecanoic acid, has limited solubility so less of the precursor was used to make the sulfonated peracid studied. The same amount of precursor acid was used for making each of the other sulfonated peracids tested.

Figure 7:
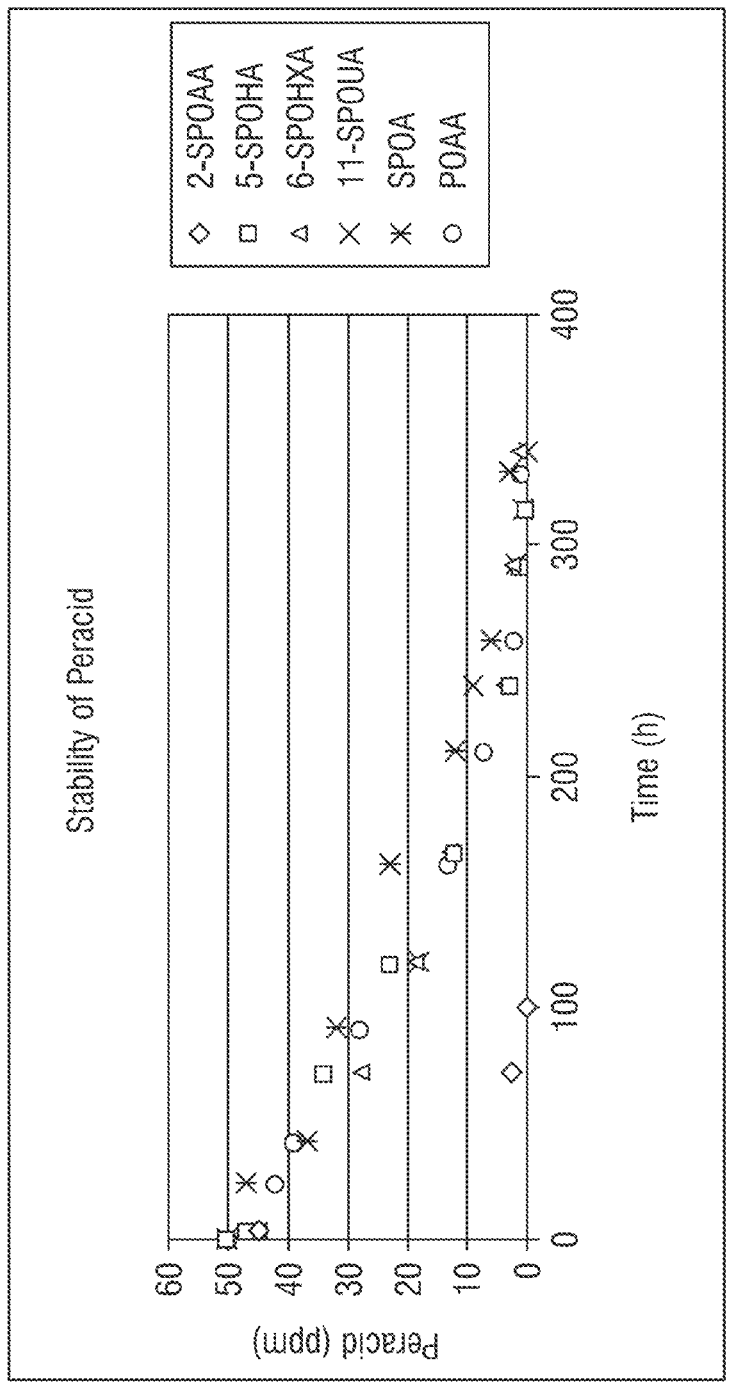
FIG. 7 is a graphical depiction of the stability of selected sulfonated peracids in aqueous solutions over time.

The peracid concentration over time was measured using a kinetic iodometric titration method. The stability of each of the sulfonated peracids is shown in FIG. 7. For comparison, 50 ppm peroxyacetic acid (POAA), at the same concentration and under the same conditions, was also included in the stability study. Based on the results seen in FIG. 7, the half time of each individual peracid was estimated and the results are summarized in the table below.

TABLE 20

| | Peracid | | | | | |
|---|---|---|---|---|---|---|
| | POAA | 2-SPOAA | 5-SPOHA | 6-SPOHXA | 11-SPOUA | PSOA |
| $t_{1/2}$ (hours) | 115 | 37 | 110 | 88 | 91 | 155 |

As can be seen from the table above, 5-SPOHA, 6-SPOHXA, and 11-SPOUA have similar stability profiles in aqueous solutions compared to that of POAA. The 2-SPOAA had a significantly shorter half life time.

Also as can be seen from these results, the stability of the mid-chain sulfonated PSOA was significantly better than that of POAA under the tested conditions. Without wishing to be bound by any particular theory, it is thought that the PSOA is the only peracid tested which has detergency, and which will form a micelle in an aqueous solution. Given that the sulfo group in the mid-chain sulfonated PSOA, is located near the center of the molecule, it is thought that the peroxycarboxylic portion is protected within a generally hydrophobic domain of vesicles or related microstructures when PSOA is dissolved in water. This results in a substantially greater stability and longer half-life than the terminally sulfonated peracids.

Example 13

Bleaching Study

A study was performed to determine the bleaching properties of various sulfonated percarboxylic acids in aqueous solutions. The sulfonated peracids were compared to a surfactant/builder only control, as well as to peroxyacetic acid.

The following sulfonated peracids were tested: 2-Sulfoperoxyacetic acid (2-SPOAA); 5-sulfoperoxyheptanoic acid (5-SPOHA); 6-sulfoperoxyhexanoic acid (6-SPOHXA); 11-sulfoperoxyundecanoic acid (11-SPOUA); and sulfonated peroleic acid product (PSOA). The individual sulfonated peracids were made, and allowed to incubate/equilibrate at 40° C. for 5 to 7 days. After determining the peracid concentrations, the respective peracid solutions were normalized for potential available oxygen as delivered by the peracids only. These solutions were tested for their bleaching power at 100° F., pH 7 and in 5 grain hard water over a 20 minute exposure. The table below shows the initial available oxygen from each peracid, as well as the percent of peracid titrated

TABLE 21

| | Composition | | | | | | |
|---|---|---|---|---|---|---|---|
| | POAA* | 2-SPOAA | 5-SPOHA | 6-SPOHXA | 11-SPOUA | PSOA | Buffer Control |
| Available Oxygen measured in peroxyacids' bleach concentrates formulae (ppm) | 32840 | 620 | 1300 | 1100 | 400 | 760 | 0 |
| Concentrate sample bleach solution Wt (g) | 0.19 | 10.00 | 4.81 | 5.70 | 15.60 | 8.20 | 0 |
| Volume of buffer concentrate used (8.5%/8.5%, NaHCO$_3$/Na$_2$CO$_3$) (mL) | 5.00** | 5.00 | 5.00 | 5.00 | 5.00 | 5.00 | 5.00 |
| Diluent (DI-H2O) mL | 120 | 120 | 120 | 120 | 120 | 120 | 120 |
| Available Oxygen from peroxyacids in bleach solutions | 50 | 50 | 50 | 50 | 50 | 50 | 0 |
| Total Bleach Use-Solution Volume (mL) | 125 | 125 | 125 | 125 | 125 | 125 | 125 |

*POAA: Peroxyacetic acid
**Required additional Acetic acid to reach pH target ~7.0

The sulfonated peracids were evaluated for their bleaching properties (also referred to herein as "soil removal" properties) by exposing soiled swatches including: tea on 100% cotton; tea on a cotton-polyester blend; and wine on 100% cotton. The soiled swatches were purchased from Test Fabrics, Inc., West Pittston, Pa. The exposure of the swatches to the various chemistries took place in a washing device known as a Terg-o-tometer (United States Testing Co., Hoboken, N.J.). The device provides 6 stainless steel 1 L beakers immersed in a temperature controlled water bath which was held at 100° F. for a 20 minute wash/bleach cycle. Each beaker includes an overhead agitator which rotates 180 degrees before reversing at a frequency of 100 hz. Each test solution contained sufficient bicarbonate-carbonate buffer to produce a pH of approximately 7+/−0.5 units for the 20 minute wash cycle.

After completing the 20 minute wash cycle the fabric samples were removed and immediately rinsed with cold synthetic 5 grain water until 5 cycles of fills and rinses were complete. The swatches were then laid flat and dried overnight on white polyester-cotton towels before reflectance readings were taken using a spectrophotometer, e.g., Hunter ColorQuest XE (reflectance) Spectrophotometer.

To determine the percent (%) soil removal (SR), e.g., bleaching ability, the reflectance of the fabric sample was measured on a spectrophotometer. The "L value" is a direct reading supplied by the spectrophotometer. L generally is indicative of broad visible spectrum reflectance, where a value of 100% would be absolute white. The % soil removal is calculated from the difference between the initial (before washing) lightness (L) value and the final L value (after washing):

$$SR=((L_{final}-L_{initial})/(96-L_{initial}))\times 100\%$$

The results of the soil removal/bleaching test are shown in the table below.

TABLE 22

| | Composition | | | | | | |
|---|---|---|---|---|---|---|---|
| | POAA (Peroxyacetic acid) | 2-SPOAA | 5-SPOHA | 6-SPOHXA | 11-SPOUA | PSOA | Buffer Control |
| SR (%) Tea on 100% cotton | 50 | 4 | 47 | 45 | 12 | 62 | 11 |
| SR (%) Tea on cotton-poly blend | 42 | −2 | 46 | 45 | 10 | 65 | 4 |
| SR (%) Red Wine on 100% cotton | 68 | 46 | 72 | 69 | 48 | 80 | 34 |

These results of the soil removal/bleaching test were also compared to the POAA control. The results are shown in the table below.

TABLE 23

| | Composition | | | | | | |
|---|---|---|---|---|---|---|---|
| | POAA (Peroxyacetic acid) | 2-SPOAA | 5-SPOHA | 6-SPOHXA | 11-SPOUA | PSOA | Buffer Control (BWC) |
| SR (%) Tea on 100% cotton | 0 | −46 | −3 | −5 | −38 | 12 | −39 |
| SR (%) Tea on cotton-poly blend | 0 | −44 | 3 | 2 | −32 | 22 | −39 |
| SR (%) Red Wine on 100% cotton | 0 | −22 | 4 | 1 | −20 | 12 | −34 |

Figure 8:
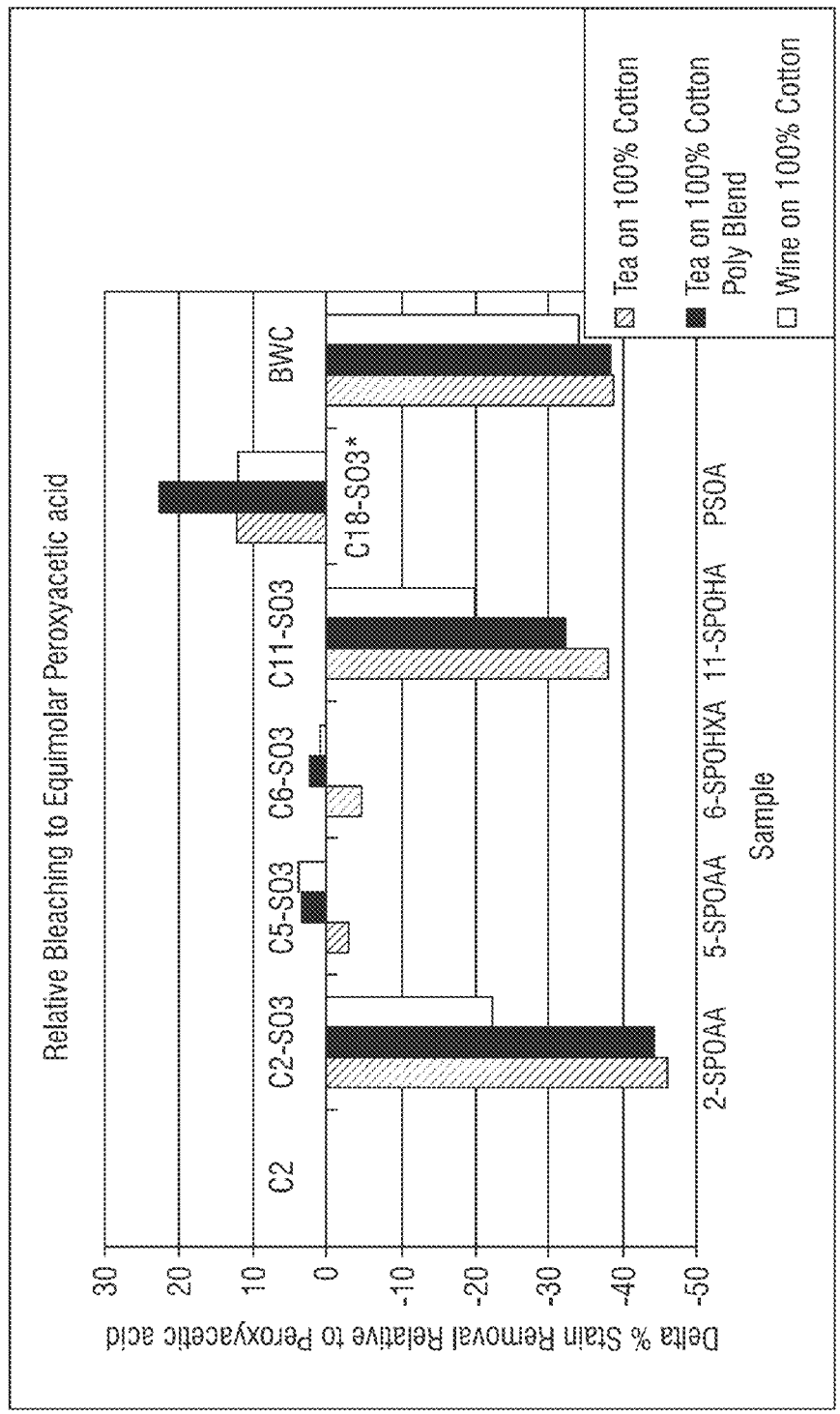
FIG. 8 is a graphical depiction of the bleaching abilities of selected sulfonated peracids compared to peroxyacetic acid.

FIG. 8 also graphically depicts these soil removal results relative to the soil removal achieved with an equimolar amount of peroxyacetic acid.

As can be seen from these results, with respect to bleaching, only the PSOA, a mid-chain sulfonated peracid, produced a significant improvement over peroxyacetic acid. The other terminally sulfonated peracids tested resulted in only small improvements over peroxyacetic acid in some cases, and in most cases produced a negative effect relative to equimolar peroxyacetic acid.

Example 14

Coupling Ability Study

A study was performed to determine the coupling/hydrotropic properties of various sulfonated peracids in aqueous solutions. The ability of the selected peracids to couple octanoic acid was measured.

The following sulfonated peracids were tested: 2-Sulfoperoxyacetic acid (2-SPOAA); 5-sulfoperoxyheptanoic acid (5-SPOHA); 6-sulfoperoxyhexanoic acid (6-SPOHXA); 11-sulfoperoxyundecanoic acid (11-SPOUA); and sulfonated peroleic acid product (PSOA). Twenty grams (20 g) of each peracid solution was diluted into a beaker containing hydrogen peroxide. Each peracid dissolved completely, except for 11-SPOUA which dissolved only partially. To each of these solutions, 0.4 grams of 1-octanoic acid was added. The octanoic acid initially floated to the tops of the solutions. The solutions were then stirred for 5-10 minutes with magnetic stir bars at 1,000 rpm. The solutions were then centrifuged for 20 minutes at 3,000-5,000 rpm. The lower phase of each solution was then collected. The lower phases were further clarified by filtration through 0.45 micron syringe filters. All of the filtrates appeared clear and homogenous. The filtered solutions were analyzed by liquid chromatography for 1-octaonic acid. The results are shown in the table below.

TABLE 23

| Solution | 1-Octanoic acid (ppm) |
|---|---|
| 2-SPOAA | 160 |
| 5-SPOHA | 230 |
| 6-SPOHXA | 240 |
| 11-SPOUA | 890 |
| PSOA | 13,200 |

As can be seen from these results, the mid-chain sulfonated peracid, PSOA, showed a far greater coupling ability for coupling octanoic acid compared to the other terminally sulfonated peracids tested. The mid-chain sulfonated PSOA had approximately a 1300% greater ability to couple octanoic acid compared to the next closest sulfonated peracid, 11-SPOUA.

Example 15

Contact Angle Study

A study was performed to measure the wetting properties of various sulfonated peracids in aqueous solutions, by measuring the contact angle of the individual solution on different surfaces.

The following sulfonated peracids were tested: 2-Sulfoperoxyacetic acid (2-SPOAA); 5-sulfoperoxyheptanoic acid (5-SPOHA); 6-sulfoperoxyhexanoic acid (6-SPOHXA); 11-sulfoperoxyundecanoic acid (11-SPOUA); and sulfonated peroleic acid product (PSOA).

A FTA32 Contact Angle Goniometer with image processing by FTA 32 software was used to measure the contact angle. The contact angle was measured on both stainless steel, and polypropylene surfaces. The peracid concentrates shown in the table below were diluted 250 times with DI water. However, the 11-SPOUA was diluted 85 times with DI water, given the lower levels of peracid precursor in the formula.

TABLE 24

| | Composition | | | | | |
|---|---|---|---|---|---|---|
| | 2-SPOAA | 5-SPOHA | 6-SPOHXA | 11-SPOUA | PSOA | Control |
| Peracid Titrated | 0.38% | 1.02% | 0.97% | 0.41% | 1.27% | NA |

The table below shows the contact angle observed for the tested peracids on both stainless steel and polypropylene surfaces. The results shown are the average of at least three contact angle measurements.

TABLE 25

| | Contact Angle (degree) | |
|---|---|---|
| Solution | Stainless Steel | Polypropylene |
| 2-SPOAA | 77 | 75 |
| 5-SPOHA | 68 | 75 |
| 6-SPOHXA | 77 | 84 |
| 11-SPOUA | 72 | 77 |
| PSOA | 52 | 56 |
| Control | 81 | 79 |

As can be seen from these results, only the mid-chain sulfonated PSOA had a significantly lower contact angle on both surfaces tested, compared to the control. The PSOA had about a 36% lower contact angle than the control on the stainless steel surface, and about a 29% lower contact angle than the control on the polypropylene surface. Without wishing to be bound by any particular theory, it is thought that a lower contact angle indicates a greater wetting ability, resulting in greater detergency.

Example 16

Antimicrobial Study

A study was performed to determine the antimicrobial efficacy of various sulfonated peracids. Use solutions containing 100 ppm of the following persulfonated acids were tested: 2-sulfoperoxyacetic acid (2-SPOAA); 5-sulfoperoxyheptanoic acid (5-SPOHA); 6-sulfoperoxyhexanoic acid (6-SPOHXA); 11-sulfoperoxyundecanoic acid (11-SPOUA); and sulfonated peroleic acid product (PSOA).

The use solutions were tested against $Staphylococcus$ $aureus$ ATCC 6538 and $Escherichia$ $coli$ ATCC 11229. The following test procedure was used. First, 99 ml of the persulfonated acid to be tested was dispensed into a 250 ml flask. The liquid was allowed to equilibrate to 25±1° C. The liquid was then swirled in the flask and 1 ml of a $10^{10}$ CFU/ml of the test bacteria was added to the beaker. After the desired exposure time, 1 mL of the combined peracid/bacteria solution was removed from the flask. The removed solution was then placed in 9 mls of an appropriate neutralizer. The desired dilution was then plated and allowed to incubate at 35° C. for 48 hours. The plates are then read to determine the reduction in microbial count. For this experiment, samples were tested over 90 seconds total exposure time, at 10 second intervals.

Figure 9:
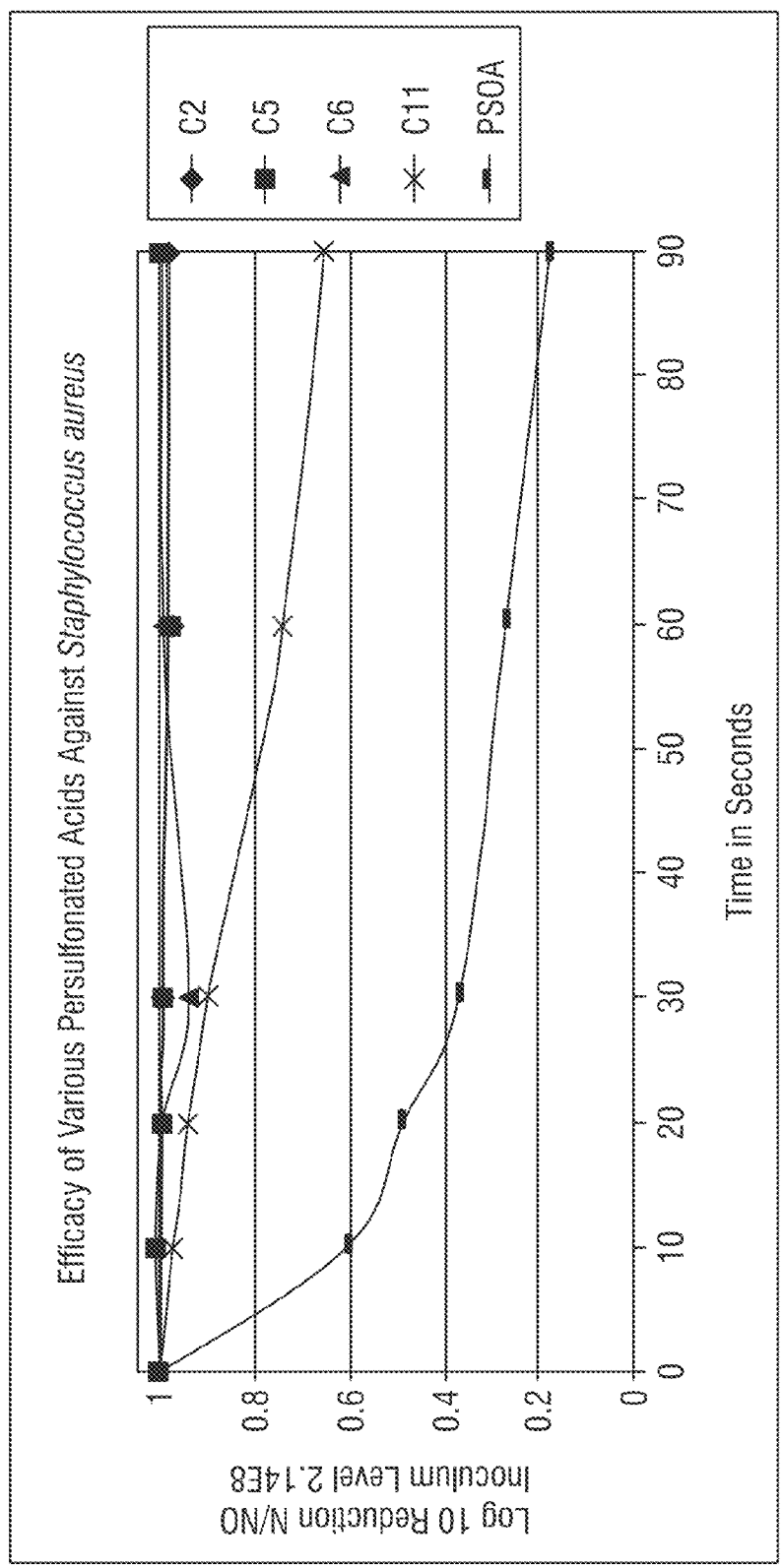
FIG. 9 graphically depicts the efficacy of selected sulfonated peracids against *Staphylococcus aureus* at ambient temperature.
Figure 10:
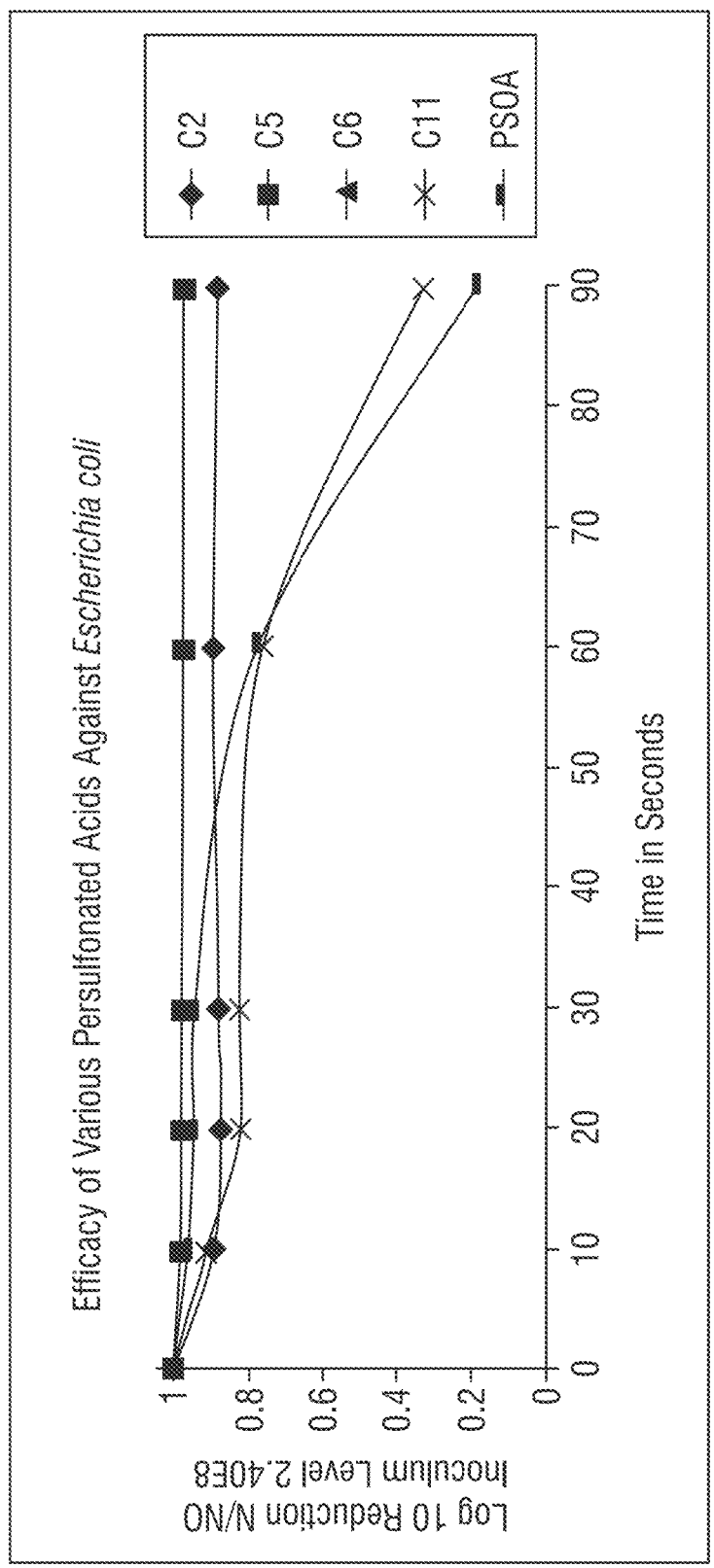
FIG. 10 graphically depicts the efficacy of selected sulfonated peracids against *Escherichia coli* at ambient temperature.

The results are shown in FIGS. 9 and 10. These figures show the ratio between the survivors (N) and the initial inoculum numbers (N0) at a give time point. For example, if the ratio of survivors (N) to the initial inoculum numbers (N0) is 1.0, no antimicrobial activity is achieved. As the rate approaches zero, complete kill is achieved. FIG. 9 graphically depicts the efficacy of the tested persulfonated acids against $Staphylococcus$ $aureus$ at ambient temperature. As can be seen from this Figure, the mid-chain sulfonated PSOA had a significantly higher reduction in the population of $S.$ $aureus$ than the other terminally sulfonated peracids tested, both initially (at 10 seconds), and over the course of the time tested.

FIG. 10 graphically depicts the efficacy of the tested persulfonated acids against $Escherichia$ $coli$ at ambient temperature. As can be seen from this Figure, the mid-chain sulfonated PSOA had a significantly higher reduction in the population of $E.$ $coli$ at 90 seconds, compared to the short chain, terminally sulfonated peracids tested. Thus, overall, it was observed that mid-chain sulfonated peracids are more effective at reducing populations of $S.$ $aureus$, and $E.$ $coli$.

Example 17

Combined Cleaning, Bleaching and Disinfecting Compositions for Textiles

Formula G was prepared using 44.90 weight percent hydrogen peroxide (50% active), 0.10 weight percent dipicolinic acid, 2.0 weight percent sulfuric acid, 5.00 weight percent propylene glycol. To these ingredients sulfonated oleic acid (SOA), linear alkylbenzene sulphonate (LAS), and 1-octanoic acid were added (or not) in the amounts provided below.

In the first series of examples, the only carboxylic acid present in the formulas is sulfonated oleic acid. Therefore, the only peracid that can form is the peroxy-sulfonated oleic acid (PSOA), so that when the total peracid level is titrated the measured value will only reflect the amount of PSOA

| Formula | SOA (weight %) | LAS (weight %) | Octanoic Acid (weight %) |
|---|---|---|---|
| G1 | 48 | — | — |
| G7 | 24 | 24 | — |
| G22 | 6 | 42 | — |

After formulation, the Formula G compositions were allowed to equilibrate at 100° F. for 1 week and then titrated to determine the amount of PSOA. These examples demonstrate peracid formation in a single carboxylic acid system containing only the PSOA type of sulfonated oleic acid.

| Formula | % PSOA |
|---|---|
| G1 | 4.4 |
| G7 | 4.4 |
| G22 | 2.6 |

In the second series of examples, there was a mixed peracid system containing two peracids: peroxyoctanoic acid (POOA) and peroxy-sulfonated oleic acid (PSOA). A standard iodine/thiosulfate titration is unable to distinguish between the two peracids, so the titrated value is equal to the total peracid content, i.e. the sum of the two peracids. To uniquely identify the amount of each component, the POOA levels were determined by HPLC. The total peracid levels were then determined by iodometric titration. By subtracting the amount of thiosulfate needed to titrate the POOA from the total amount of thiosulfate used, the amount of thiosulfate needed to titrate the PSOA could be determined. From that value, the percent PSOA in the formulations could be obtained. The single example shown below demonstrates the formation of PSOA in a mixed peracid system, and is representative for all other examples.

| Formula | % POOA | % PSOA |
|---|---|---|
| G10 | 8.8 | 4.5 |

| Formula | SOA (weight %) | LAS (weight %) | Octanoic Acid (weight %) |
|---|---|---|---|
| G2 | — | 48 | — |
| G3 | — | — | 48 |
| G4 | 8 | 8 | 32 |
| G5 | 8 | 32 | 8 |
| G6 | 32 | 8 | 8 |
| G8 | 24 | — | 24 |
| G9 | — | 24 | 24 |
| G10 | 16 | 16 | 16 |
| G11 | 5 | 36 | 7 |
| G12 | 5 | 20.5 | 22.5 |
| G13 | 5 | 5 | 38 |
| G14 | 15.33 | 15.33 | 17.33 |
| G15 | 20.5 | 20.5 | 7 |
| G16 | 25.67 | 10.17 | 12.17 |
| G17 | 10.17 | 25.67 | 12.17 |
| G18 | 10.17 | 10.17 | 27.67 |
| G19 | 36 | 5 | 7 |
| G20 | 20.5 | 5 | 22.5 |
| G21 | 2 | 44 | 2 |

After formulation, the Formula G compositions were allowed to equilibrate at 100° F. for 1 week. Upon conclusion of that time period, the samples were evaluated for stability by visual inspection. Results are provided in the table below and show a variety of useful formulary capabilities covering both gel and liquid compositions.

Stability Results:

TABLE 27

| Sample | Visual appearance |
|---|---|
| G1 | Gel-like, single phase |
| G5 | Gel-like, single phase |
| G17 | Gel-like, single phase |
| G7 | Clear-liquid, single phase |
| G12 | Clear-liquid, single phase |
| G15 | Clear-liquid, single phase |
| G10 | Clear-liquid, single phase |
| G16 | Clear-liquid, biphasic |
| G18 | Clear-liquid, biphasic |
| G1 | Clear-liquid, biphasic |
| G3 | Clear-liquid, biphasic |

Formulations were single phase when they had a high LAS content, and yielded gel-like formulations with a favorable and stable high viscosity (Samples G1, G5, G17). Conversely, and as desired in other formulations where a liquid is desired, as the LAS concentration decreased, formulations produced a clear, isotropic liquid (Samples G7, G12, G15, and G10). However, as the amount of either the SOA or octanoic acid increased, the formulations exhibited gross phase separation resulting in two clear phases (Samples G16, G18, G1, G3). A range of product phases are most desirable that yield a single, liquid, solid, or gel phase. One single phase liquid is most desirable for some applications requiring automated dosing pumps, while single phase gels are most favorable for hand-feed or non-automated processes. Though the modes of formulation optimization limits differed (e.g., gel formation for high LAS systems and phase separation for excessive octanoic acid and SOA), if any one surfactant comprised more than 50% of the total surfactant level it prevented the formation of a clear, isotropic liquid; however, it could yield a single phase gel.

Color-Stability of Formula G Samples

The color of the different formulations was evaluated using a spectrophotometer (ColorQuest XE, Hunter Associates Laboratory). The CIE L*, a*, b* color space is a 3-dimensional rectangular color space based on the opponent-colors theory. For the L* (lightness) axis 0 is black and 100 is white. For the a* (red-green) axis positive values are red, negative values are yellow and 0 is neutral. For the b* (blue-yellow) axis positive values are yellow; negative values are blue and 0 is neutral. All colors that can be visually perceived can be plotted in this L*, a*, b* rectangular color space.

TABLE 28

| | Initial Sample Color: | | |
|---|---|---|---|
| Sample | L* | A* | B* |
| G3 | 94.28 | −3.47 | 12.47 |
| G4 | 85.45 | −4.14 | 20.68 |
| G10 | 87.63 | −5.89 | 20.76 |
| G6 | 65.13 | −5.03 | 33.08 |
| G7 | 82.05 | −4.8 | 60.75 |

The above initial color data show there was significant color variation between formulations, especially in regard to b*, the blue-yellow axis. Regardless of starting color, samples lightened in color over time, ultimately becoming almost colorless (see Sample G10 data below comparing initial color and color at equilibrium). There is no specific threshold above which the b* value, i.e. a greater degree of yellow, is considered unacceptable. Formulations with a higher starting b* value will exhibit greater color changes during the equilibration period, which could be perceived as a sign of instability. Therefore, a lower initial b* value, exhibited in Formula G samples containing more octanoic acid, could be perceived as more preferred than a higher initial b* value.

TABLE 29

Initial color compared to equilibrium color:

| Sample | L* | A* | B* |
|---|---|---|---|
| G10 Initial | 87.63 | −5.89 | 20.76 |
| G10 Equilibrium | 89.62 | −2.41 | 3.02 |

Bleaching and Detergency Evaluation:

The Formula G compositions were evaluated for bleaching and detergency using wash wheel performance data. A commercial 35 lb front loading washing machine (Huebsch model HX35PVXU60001) was used for the tests. The ability of the Formula G compositions to remove soil was determined by washing artificially soiled fabric swatches. The pre-soiled swatches were purchased from a Test Fabrics, Inc. located in West Pittston, Pa. Polyester/cotton blend pillowcases weighing 24 pounds were used as ballast.

The wash formula was programmed to run for 14 minutes at 40° C. using 60 liters of 5 grain synthetic soft water. One hundred grams of each Formula G sample was added to the machine per run and no additional chemicals were added allowing the actual run pH to fluctuate to its natural level. In the instances where the Formula G samples were not a single, isotropic phase, the solutions were mixed by inversion twice a day for the week prior to the test, and the entire two phase sample was added to the wash-wheel. After the wash step, there were three subsequent rinse cycles and a final extract. After completing the entire cycle, the soil swatches were retrieved from the washer and allowed to air dry overnight at 70° F.

Percent soil removal was determined by measuring the reflectance of the fabric using a ColorQuest XE spectrophotometer available from Hunter Associates Laboratory. The "L value" was a direct reading supplied by the spectrophotometer. L value is generally indicative of broad visible spectrum reflectance, where a value of 100% would be absolute white. The percent soil removal was calculated using the following formula:

$$SR = ((L_{final} - L_{initial})/(96 - L_{initial}))*100\%$$

The average stain removal data is provided in the following table:

TABLE 30

| Sample | Percent Stain Removal | | | |
|---|---|---|---|---|
| | Coffee PC | Curry | Tea | Sum |
| G2 | 8.5 | 9.7 | 8.7 | 26.9 |
| G21 | 21.6 | 18.9 | 22.3 | 62.8 |
| G22 | 21.7 | 22 | 21.6 | 65.3 |
| G5 | 39.8 | 33.3 | 23.3 | 96.4 |
| G10 | 53.9 | 50.9 | 37 | 141.8 |

TABLE 30-continued

| Sample | Percent Stain Removal | | | |
|---|---|---|---|---|
| | Coffee PC | Curry | Tea | Sum |
| G4 | 56.5 | 51.4 | 39.1 | 147 |
| G3 | 50.9 | 46.8 | 35 | 132.7 |
| G6 | 49.6 | 41.2 | 28.9 | 119.7 |
| G1 | 41.3 | 32.1 | 19 | 92.4 |

Though hydrogen peroxide alone acts as an oxidizing bleach, it is known to have severely reduced effectiveness at low temperatures and acidic pH. When LAS is present as a sole surfactant in the Formula G2 sample, there is no peracid formation. In that formulation lacking peracid, any bleaching that occurs is due solely to hydrogen peroxide and the stain removal was minimal (i.e., <10% for any single bleachable soil classification in columns 2-4); cf., G2 and all other formulations of Table 30. As the other components (SOA, octanoic acid) were added (Formulas G1, and G3-G22) and the amount of potential peracid increased, so too did the stain removal. As can be seen, the amount of octanoic acid is the most important contributor to bleachable stain removal, with the bleachable stain removal values increasing as octanoic acid increased and decreasing as octanoic acid decreased. To optimize bleaching, octanoic acid is optionally included in the composition in an amount of between about 0.1 to 35 weight %, and between 2.0 and 25 weight %; and between 4.0 weight % and about 20 weight %.

Detergency, or removal of soils that were not susceptible to oxidation, was also evaluated. Detergency results are provided below:

TABLE 31

| Sample | Percent Stain Removal | | | |
|---|---|---|---|---|
| | Olive Oil PC | Lipstick | Makeup | Sum |
| G2 | 21.2 | 62.5 | 18.9 | 102.6 |
| G21 | 22.6 | 53.3 | 18.1 | 94 |
| G22 | 21.7 | 64.6 | 22.3 | 108.6 |
| G5 | 27.2 | 68.1 | 21 | 116.3 |
| G10 | 28.9 | 66.9 | 26.2 | 122 |
| G6 | 21.8 | 67.7 | 28.7 | 118.2 |
| G4 | 18.3 | 66.5 | 23.6 | 108.4 |
| G1 | 26.8 | 66 | 31.1 | 123.9 |
| G3 | 17 | 65.6 | 20.3 | 102.9 |

Detergency was less dependent upon formulation than bleaching except when formulations had high (or exclusive) LAS and octanoic acid. The results suggest that the presence of multiple surfactants can be beneficial although the exact ratio of the surfactants doesn't seem to cause significant differences in results. Most importantly this wide variance in formulation capability allows for preparation of compositions that are liquids, gels, or solids.

pH

As already mentioned, the pH of the use solution was allowed to vary to its natural level, i.e. no additional chemicals were added to target a certain pH throughout the wash tests. After the formulations were dispensed into the washwheel, they were allowed to mix for one minute after which a 100 mL aliquot was removed and the pH measured. The pH measurements are provided below:

TABLE 32

| Sample | pH |
|---|---|
| G1 | 6.2 |
| G10 | 5.8 |
| G6 | 5.9 |
| G16 | 6 |
| G14 | 3.9 |
| G10 | 6.7 |
| G15 | 4.4 |
| G12 | 2.6 |
| G7 | 3.3 |
| G17 | 2.9 |
| G1 | 2.8 |

Peracids are weaker acids (that is, have a higher pKa value) than the parent carboxylic acid. Greater peracid formation in the concentrate should lead to a higher pH with the use solution; especially in the presence of typical water hardness conditions found in many textile laundering waters. Since LAS is unable to form a peracid, it remains in its most acidic form. Given the above, formulations containing higher amounts of LAS and lower peracid conversion will have a lower pH in the wash-wheel. Greater amounts of SOA and octanoic acid yield a higher pH upon dilution and may be more preferred in textile applications.

Example 18

Combined Cleaning, Bleaching and Disinfecting Compositions for Textiles with Varied Nonionic, Amine Oxide, and Anionic Surfactants and Amounts Formula H was prepared using 13 weight % sulfonated oleic acid, 35.9 weight % hydrogen peroxide, 13 weight % alkyl ($C_{10}$-$C_{16}$) benzenesulfonic acid, 13 weight % 1-octanoic acid, 0.1 weight % pyridine-2,6-dicarboxylic acid. To the Formula H compositions, the ingredients provided in the following tables were added in the amounts provided to prepare Formula H samples H1-H25. The initial stability data of the Formula H samples was indicated.

TABLE 33

| Ingredient | H1 | H2 | H3 | H4 | H5 | H6 | H7 |
|---|---|---|---|---|---|---|---|
| Sulfuric Acid | 1.5 | 1.5 | 1.5 | 1.5 | 1.5 | 1.5 | 1.5 |
| Propylene glycol | 23.5 | 3.5 | 3.5 | 3.5 | 3.5 | 3.5 | 3.5 |
| Benzenesulfonic acid | 0 | 0 | 0 | 5 | 0 | 0 | 5 |
| Primary $C_{12}$-$C_{14}$ linear alcohol plus 7 ethylene oxide (EO) groups | 0 | 20 | 10 | 10 | 10 | 0 | 0 |
| Primary $C_{12}$-$C_{14}$ linear alcohol plus 3 EO groups | 0 | 0 | 10 | 5 | 0 | 0 | 0 |
| Primary $C_{12}$-$C_{14}$ linear alcohol plus 12 EO groups | 0 | 0 | 0 | 0 | 20 | 0 | 0 |
| Branched $C_{13}$ alcohol plus 7 EO groups | 0 | 0 | 0 | 0 | 0 | 20 | 15 |
| $C_{10}$ Guerbet alcohol alkoxylate plus 5 EO groups | 0 | 0 | 0 | 0 | 0 | 0 | 0 |
| Nonionic seed oil surfactant (Ecosurf SA-4) | 0 | 0 | 0 | 0 | 0 | 0 | 0 |
| Nonionic seed oil surfactant (Ecosurf SA-9) | 0 | 0 | 0 | 0 | 0 | 0 | 0 |
| Benzenesulfonic acid | 0 | 0 | 0 | 0 | 0 | 0 | 0 |
| Lauryl dimethyl amine oxide | 0 | 0 | 0 | 0 | 0 | 0 | 0 |
| Citric acid | 0 | 0 | 0 | 0 | 0 | 0 | 0 |
| Alkyl polyglucoside based on natural fatty alcohol $C_8$-$C_{16}$ | 0 | 0 | 0 | 0 | 0 | 0 | 0 |
| Polyoxyethylene sorbitan monolaurate | 0 | 0 | 0 | 0 | 0 | 0 | 0 |
| Succinic Acid | 0 | 0 | 0 | 0 | 0 | 0 | 0 |
| Acrylic acid homopolymer, Avg. MW 4500 | 0 | 0 | 0 | 0 | 0 | 0 | 0 |
| Acrylic/maleic copolymer | 0 | 0 | 0 | 0 | 0 | 0 | 0 |
| 4,4'-Bis(2-sulfostryl)biphenyl disodium salt | 0 | 0 | 0 | 0 | 0 | 0 | 0 |

TABLE 33-continued

| Ingredient | | | | | | | |
|---|---|---|---|---|---|---|---|
| 1-hydroxyethane 1,1-diphosphonic acid | 0 | 0 | 0 | 0 | 0 | 0 | 0 |
| 2,6-diterbutyl-4-methylphenol | 0 | 0 | 0 | 0 | 0 | 0 | 0 |
| Coconut oil fatty acid | 0 | 0 | 0 | 0 | 0 | 0 | 0 |
| Silicone antifoam emulsion | 0 | 0 | 0 | 0 | 0 | 0 | 0 |
| Magnesium sulfate | 0 | 0 | 0 | 0 | 0 | 0 | 0 |
| Stability Data | Clear, single phase | Clear, single phase | Cloudy biphasic | Clear, single phase | Clear, single phase | Cloudy, single | Clear, single phase |

| | Sample | | | | | | |
|---|---|---|---|---|---|---|---|
| Ingredient | H8 | H9 | H10 | H11 | H12 | H13 | H14 |
| Sulfuric Acid | 1.5 | 1.5 | 1.5 | 1.5 | 1.5 | 0 | 0 |
| Propylene glycol | 3.5 | 3.5 | 3.5 | 3.5 | 3.5 | 5 | 5 |
| Benzenesulfonic acid | 5 | 0 | 5 | 0 | 5 | 0 | 0 |
| Primary $C_{12}$-$C_{14}$ linear alcohol plus 7 ethylene oxide (EO) groups | 0 | 0 | 0 | 0 | 0 | 0 | 0 |
| Primary $C_{12}$-$C_{14}$ linear alcohol plus 3 EO groups | 0 | 0 | 0 | 0 | 0 | 0 | 0 |
| Primary $C_{12}$-$C_{14}$ linear alcohol plus 12 EO groups | 0 | 0 | 0 | 0 | 0 | 0 | 0 |
| Branched $C_{13}$ alcohol plus 7 EO groups | 0 | 0 | 0 | 0 | 0 | 5 | 0 |
| $C_{10}$ Guerbet alcohol alkoxylate plus 5 EO groups | 20 | 15 | 0 | 0 | 0 | 0 | 0 |
| Nonionic seed oil surfactant (Ecosurf SA-4) | 0 | 0 | 5 | 0 | 0 | 0 | 0 |
| Nonionic seed oil surfactant (Ecosurf SA-9) | 0 | 0 | 10 | 0 | 0 | 0 | 0 |
| Benzenesulfonic acid | 0 | 0 | 0 | 0 | 5 | 0 | 0 |
| Lauryl dimethyl amine oxide | 0 | 0 | 0 | 20 | 15 | 0 | 0 |
| Citric acid | 0 | 0 | 0 | 0 | 0 | 10 | 10 |
| Alkyl polyglucoside based on natural fatty alcohol $C_8$-$C_{16}$ | 0 | 0 | 0 | 0 | 0 | 5 | 0 |
| Polyoxyethylene sorbitan monolaurate | 0 | 0 | 0 | 0 | 0 | 0 | 10 |
| Succinic Acid | 0 | 0 | 0 | 0 | 0 | 0 | 0 |
| Acrylic acid homopolymer, Avg. MW 4500 | 0 | 0 | 0 | 0 | 0 | 0 | 0 |
| Acrylic/maleic copolymer | 0 | 0 | 0 | 0 | 0 | 0 | 0 |
| 4,4'-Bis(2-sulfostryl)biphenyl disodium salt | 0 | 0 | 0 | 0 | 0 | 0 | 0 |
| 1-hydroxyethane 1,1-diphosphonic acid | 0 | 0 | 0 | 0 | 0 | 0 | 0 |
| 2,6-diterbutyl-4-methylphenol | 0 | 0 | 0 | 0 | 0 | 0 | 0 |
| Coconut oil fatty acid | 0 | 0 | 0 | 0 | 0 | 0 | 0 |
| Silicone antifoam emulsion | 0 | 0 | 0 | 0 | 0 | 0 | 0 |

TABLE 33-continued

| Ingredient | | | | | | | |
|---|---|---|---|---|---|---|---|
| Magnesium sulfate | 0 | 0 | 0 | 0 | 0 | 0 | 0 |
| Stability Data | Cloudy biphasic | Clear, single phase | Clear, single phase | Clear, biphasic | Clear, single phase | Clear, single phase | Clear, single phase |

| | Sample | | | | | | |
|---|---|---|---|---|---|---|---|
| Ingredient | H15 | H16 | H17 | H18 | H19 | H20 | H21 |
| Sulfuric Acid | 1.5 | 1.5 | 1.5 | 1.5 | 1.5 | 1.5 | 1.5 |
| Propylene glycol | 3.5 | 3.5 | 18.5 | 18.5 | 23.2 | 18.5 | 21.5 |
| Benzenesulfonic acid | 0 | 0 | 0 | 0 | 0 | 0 | 0 |
| Primary $C_{12}$-$C_{14}$ linear alcohol plus 7 ethylene oxide (EO) groups | 0 | 0 | 0 | 0 | 0 | 0 | 0 |
| Primary $C_{12}$-$C_{14}$ linear alcohol plus 3 EO groups | 0 | 0 | 0 | 0 | 0 | 0 | 0 |
| Primary $C_{12}$-$C_{14}$ linear alcohol plus 12 EO groups | 0 | 0 | 0 | 0 | 0 | 0 | 0 |
| Branched $C_{13}$ alcohol plus 7 EO groups | 0 | 0 | 0 | 0 | 0 | 0 | 0 |
| $C_{10}$ Guerbet alcohol alkoxylate plus 5 EO groups | 0 | 0 | 0 | 0 | 0 | 0 | 0 |
| Nonionic seed oil surfactant (Ecosurf SA-4) | 0 | 0 | 0 | 0 | 0 | 0 | 0 |
| Nonionic seed oil surfactant (Ecosurf SA-9) | 0 | 0 | 0 | 0 | 0 | 0 | 0 |
| Benzenesulfonic acid | 0 | 0 | 0 | 0 | 0 | 0 | 0 |
| Lauryl dimethyl amine oxide | 0 | 0 | 0 | 0 | 0 | 0 | 0 |
| Citric acid | 20 | 0 | 0 | 0 | 0 | 0 | 0 |
| Alkyl polyglucoside based on natural fatty alcohol $C_8$-$C_{16}$ | 0 | 0 | 0 | 0 | 0 | 0 | 0 |
| Polyoxyethylene sorbitan monolaurate | 0 | 0 | 0 | 0 | 0 | 0 | 0 |
| Succinic Acid | 0 | 20 | 0 | 0 | 0 | 0 | 0 |
| Acrylic acid homopolymer, Avg. MW 4500 | 0 | 0 | 5 | 0 | 0 | 0 | 0 |
| Acrylic/maleic copolymer | 0 | 0 | 0 | 5 | 0 | 0 | 0 |
| 4,4'-Bis(2-sulfostryl)biphenyl disodium salt | 0 | 0 | 0 | 0 | 0.3 | 0 | 0 |
| 1-hydroxyethane 1,1-diphosphonic acid | 0 | 0 | 0 | 0 | 0 | 5 | 0 |
| 2,6-diterbutyl-4-methylphenol | 0 | 0 | 0 | 0 | 0 | 0 | 2 |
| Coconut oil fatty acid | 0 | 0 | 0 | 0 | 0 | 0 | 0 |
| Silicone antifoam emulsion | 0 | 0 | 0 | 0 | 0 | 0 | 0 |
| Magnesium sulfate | 0 | 0 | 0 | 0 | 0 | 0 | 0 |
| Stability Data | Clear, single phase | Cloudy, biphasic | Clear, one phase | Cloudy, single phase | Clear, single phase | Clear, single phase | Clear, single phase |

| Ingredient | H22 | H23 | H24 | H25 |
|---|---|---|---|---|
| Sulfuric Acid | 1.5 | 1.5 | 1.5 | 1.5 |
| Propylene glycol | 13.5 | 1.5 | 1.5 | 1.5 |
| Benzenesulfonic acid | 0 | 0 | 0 | 0 |

TABLE 33-continued

| | | | | |
|---|---|---|---|---|
| Primary $C_{12}$-$C_{14}$ linear alcohol plus 7 ethylene oxide (EO) groups | 0 | 0 | 0 | 0 |
| Primary $C_{12}$-$C_{14}$ linear alcohol plus 3 EO groups | 0 | 0 | 0 | 0 |
| Primary $C_{12}$-$C_{14}$ linear alcohol plus 12 EO groups | 0 | 0 | 0 | 0 |
| Branched $C_{13}$ alcohol plus 7 EO groups | 0 | 0 | 0 | 0 |
| $C_{10}$ Guerbet alcohol alkoxylate plus 5 EO groups | 0 | 0 | 0 | 0 |
| Nonionic seed oil surfactant (Ecosurf SA-4) | 0 | 0 | 0 | 0 |
| Nonionic seed oil surfactant (Ecosurf SA-9) | 0 | 0 | 0 | 0 |
| Benzenesulfonic acid | 0 | 0 | 0 | 0 |
| Lauryl dimethyl amine oxide | 0 | 0 | 0 | 0 |
| Citric acid | 0 | 0 | 0 | 0 |
| Alkyl polyglucoside based on natural fatty alcohol $C_8$-$C_{16}$ | 0 | 0 | 0 | 0 |
| Polyoxyethylene sorbitan monolaurate | 0 | 0 | 0 | 0 |
| Succinic Acid | 0 | 0 | 0 | 0 |
| Acrylic acid homopolymer, Avg. MW 4500 | 0 | 0 | 0 | 0 |
| Acrylic/maleic copolymer | 0 | 0 | 0 | 0 |
| 4,4'-Bis(2-sulfostryl)biphenyl disodium salt | 0 | 0 | 0 | 0 |
| 1-hydroxyethane 1,1-diphosphonic acid | 0 | 0 | 0 | 0 |
| 2,6-diterbutyl-4-methylphenol | 0 | 0 | 0 | 0 |
| Coconut oil fatty acid | 10 | 10 | 0 | 0 |
| Silicone antifoam emulsion | 0 | 0 | 0.2 | 0 |
| Magnesium sulfate | 0 | 0 | 0 | 5 |
| Stability Data | Clear, single phase | Clear, single phase | Clear, biphasic | Clear, biphasic |

As evident from the data, not all of the Formula H Samples were immediately stable after addition of the various nonionic, amine oxide, or anionic surfactants. In each of those instances, the sample could be made stable by the addition of a small amount of a classic hydrotrope, such as 5 weight percent sodium cumene sulfonate, and, thus, extend the liquid, gel, and solid formulation scope for the current invention.

Detergency of the Samples H1-H25 was tested and no significant differences in detergency resulted between any of the samples; thus showing the wide scope of formulations capable of enabling the current invention. Laundry compositions as prepared in the Formula G and H samples were effective at cleaning, bleaching, and disinfecting despite the absence of nitrogen-based chelants, phosphorous and/or phosphates and/or phosphonates, and heavy metal—specifically transition metals, post-transition metals, and metalloids with an atomic number above 38. These examples also demonstrate systems free of caustic or alkali metal hydroxide in the compositions; however, other systems using caustic or alkali metal hydroxides to moderate the pH to various desirable levels are also disclosed in other example of the current application.

Example 19

Extended Peracid Stability of Combined Cleaning, Bleaching and Sanitizing and/or Disinfecting and/or Sterilizing Compositions In these combined detergent, bleach and/or antimicrobial compositions, the bleaching and/or antimicrobial effect is a result of the peracid formed through an acid reaction. One requirement for a peracid-containing product is long term stability where the peracid doesn't rapidly decompose or revert back to the starting carboxylic acid. Shown in Table 34 is a wide variety of formulations containing different types of raw materials, including surfactants, solvents or cosolvents and antifoam agents. As a means of accelerating testing, the samples are usually stored at elevated temperatures, in this case 100° F.

TABLE 34

|  | I1 | I2 | I3 | I4 | I5 | I6 |
|---|---|---|---|---|---|---|
| Sulfonated oleic acid | 16 | 12 | 12 | 6.3 | 12 | 12 |
| Hydrogen peroxide (50%) | 44.9 | 33.9 | 33.9 | 18 | 33.9 | 33.9 |
| Alkyl (C10-C16) Benzenesulfonic acid | 16 | 12 | 6 | 6.3 | 6 | 6 |
| 1-Octanoic acid | 16 | 12 | 12 | 6.3 | 12 | 12 |
| pyridine-2,6-dicarboxylic acid | 0.1 | 0.1 | 0.1 | 0.1 | 0.1 | 0.1 |
| Sulfuric acid | 2 |  |  |  |  |  |
| propylene glycol | 5 | 5 | 5 | 10 | 5 | 5 |
| Primary C12-C14 linear alcohol plus 7 ethylene oxide (EO) groups |  | 25 | 31 | 53 | 21 | 29 |
| Coconut oil fatty acid |  |  |  | 10 |  |  |
| Aluminum sulfate |  |  |  |  |  | 2 |
| Sum | 100 | 100 | 100 | 100 | 100 | 100 |

In all cases the peracid level remained relatively constant over time, showing only minimal degradation from initial formation to day 28 (Table 35). In some examples with lesser amounts of acid, it takes some time for the peracid to reach a reaction level. In formulas I1 and I2 the reaction level is reached rapidly, as demonstrated by the minimal change between Day 0 and Day 4. Formulas I3, I4, I5, and I6 all have lower levels of LAS, the strongest acid present in those formulas. This leads to slower equilibrium or reaction level peracid formation, as demonstrated by the peracid levels increasing between Day 0 and Day 4, in some instances by almost 100%. Regardless of the initial rate of peracid formation, the stability over time is unaffected.

TABLE 35

|  | % Peracid | | | |
|---|---|---|---|---|
|  | Day 0 | Day 4 | Day 7 | Day 28 |
| I1 | 11.0 | 10.9 | 10.8 | 10.6 |
| I2 | 6.8 | 6.9 | 6.5 | 6.0 |
| I3 | 3.8 | 6.1 | 5.6 | 5.3 |
| I4 | 1.9 | 3.2 | 2.9 | 2.0 |
| I5 | 4.5 | 8.9 | 8.7 | 7.1 |
| I6 | 4.0 | 6.1 | 6.3 | 5.9 |

Example 20

Foam Levels from Combined Cleaning, Bleaching and/or Sanitizing Compositions

Foam control is an important priority for all laundry detergents, but especially when used in front loading washer extractors, or continuous batch (tunnel) washers. These two types are the predominant washers found in industrial and institutional laundries. Too much foam can impede the wash process by reducing soil removal and interfering with effective rinsing. To mimic the amount of foam that is generated during actual washer usage, a laboratory method may be used. A small amount (0.25 g) of the test sample was added to 100 g of soft (0 grain) water in a 250 mL graduated cylinder. The cylinder was stopped and then agitated through 120 degree rotations for 1 minute (about 1 cycle/sec). After agitation the foam was allowed to settle for 1 min, and the total volume was measured. The volume of the foam was equal to the total volume minus the initial water volume (100 mL). The formulations tested are seen in Table 36. L2000 XP is an institutional laundry detergent commercially available from Ecolab, Inc. The data is reported as foam volume (mL), normalized per g of material (Table 37).

TABLE 36

|  | J1 | J2 | J3 | J4 | J5 | J6 | J7 | J8 |
|---|---|---|---|---|---|---|---|---|
| Sulfonated oleic acid | 12 | 12 | 12 | 12 | 12 | 12 | 12 | 12 |
| Hydrogen peroxide (50%) | 33.9 | 33.9 | 33.9 | 33.9 | 33.9 | 34.9 | 35.9 | 35.9 |
| Alkyl (C10-C16) Benzenesulfonic acid | 6 | 6 | 6 | 6 | 6 | 6 | 4 | 4 |
| 1-Octanoic acid | 12 | 12 | 12 | 12 | 12 | 12 | 12 | 12 |
| pyridine-2,6-dicarboxylic acid | 0.1 | 0.1 | 0.1 | 0.1 | 0.1 | 0.1 | 0.1 | 0.1 |
| propylene glycol | 5 | 5 | 5 | 5 | 5 | 13 | 5 | 5 |
| Primary C12-C14 linear alcohol plus 7 ethylene oxide (EO) groups | 31 | 28 | 21 | 28 | 21 | 20 | 28.5 | 26 |
| Lauric acid |  | 3 | 10 |  |  |  |  |  |
| Coconut oil fatty acid |  |  |  | 3 | 10 |  |  |  |
| Aluminum sulfate |  |  |  |  |  | 2 |  |  |
| Primary C9-C11 linear alcohol plus 20 propylene oxide (PO) groups |  |  |  |  |  |  | 2.5 | 5 |
| Sum | 100 | 100 | 100 | 100 | 100 | 100 | 100 | 100 |

TABLE 37

| Formula | Foam volume (mL)/g sample |
|---|---|
| L2000 XP | 351 |
| J1 | 516 |
| J2 | 468 |
| J3 | 296 |
| J4 | 560 |
| J5 | 339 |
| J6 | 475 |
| J7 | 461 |
| J8 | 373 |

The commercially available detergent, L2000 XP, has a foam volume of 351 mL/g. The initial experimental formula (J1) produced more foam than the commercial standard with a volume of 516 mL/g. Addition of a long chain fatty acid (lauric acid, J2 and J3) reduces the foam volume compared to the original formula without lauric acid. It also shows a dose response relationship with 3% lauric acid (J2) reducing the foam by 9.3% and 10% lauric acid (J3) reducing the foam volume by 42.6%. With that significant reduction, the foam volume from Formula J3 is less than the commercially available reference detergent, L2000 XP. Similar to the foam reduction seen with the long chain fatty acids, an alcohol alkoxylate with extended propylene oxide groups also saw significant reductions. Adding 2.5% of the alcohol alkoxylate (J7) reduced the foam by 10.7%. Doubling the alkoxylate to 5% of the formulation (J8), brought the total foam reduction to 27.7%, and the absolute foam level into the range of the commercial detergent L2000 XP.

Example 21

Mineral Encrustation after Washing

Hardness is a measure of the calcium and magnesium ions present in water. These ions can precipitate out of solution as the carbonate form, i.e. calcium carbonate, and can deposit on surfaces. This process is accelerated under alkaline washing conditions, especially the more highly alkaline conditions often employed in industrial and institutional cleaning. Controlling encrustation is therefore required for alkaline laundering.

To assess the encrustation levels, one of the experimental formulations was compared to Formula 1, a commercially available detergent from Ecolab. For each condition six new 100% cotton terry towels were selected. Additional towels were added to bring the total weight to 28 lbs. Prior to the start of the test (Cycle 0) and after every 5 cycles (i.e. 5, 10, 15 and 20) three circles that summed to 10 g were removed from each of the 6 test towels. The cycles were run using 17 grain water and the towels were dried after each cycle. After completion of the test, all sets of towel pieces were heated in an oven at 600° F. for 12 hours, and cooled to room temperature. The beakers were weighed and the difference in final mass compared to the initial mass is the mass of the inorganic residue, or ash. Dividing that number by the starting mass of the towels, i.e. 10 g, gives the ash percent. The amount of ash is a measure of the mineral encrustation deposited on the towels. The results are seen in Table 38.

TABLE 38

| | Ash Percent | |
|---|---|---|
| Cycle | Formula 1 | I6 |
| 0 | 0.22 | 0.25 |
| 5 | 0.29 | 0.26 |
| 10 | 0.41 | 0.29 |
| 15 | 0.55 | 0.30 |
| 20 | 0.77 | 0.32 |

Each system had some level of inorganic residue present at the start of the test and both saw increasing levels of ash content throughout the 20 cycles. The Formula 1 ash content had an increase of 250%. By contrast, the formulation of the present invention only increased by 28%. Without wishing to be bound by theory it is believed that the acidic washing conditions of the present invention inhibit significant calcium carbonate precipitation, a favorable benefit in comparison to alkaline laundering.

Example 22 pH Adjustment of Combined Cleaning, Bleaching and/or Antimicrobial Compositions

In most instances the pH of the concentrated compositions is between 0-1. In some examples it may be beneficial to raise the pH of the concentrate product above 1. To do so, a batch was created and allowed to sit overnight to afford peracid formation, after which various bases were added until the desired pH was reached. The pre-neutralization base formula seen in Table 38 is used in all of the subsequent pH-adjustment examples. A product concentrate pH range from 0-4.5 is demonstrated. The absolute upper limit of the range is not established herein, and pH values higher than pH 4.5 are envisioned to be within the scope of the patent. After neutralization, the compositions were stored at 104° F., an accelerated aging condition compared to room temperature.

TABLE 39

| | K |
|---|---|
| Sulfonated oleic acid | 35 |
| Hydrogen peroxide (50%) | 20 |
| Alkyl (C10-C16) Benzenesulfonic acid | 10 |
| pyridine-2,6-dicarboxylic acid | 0.1 |
| propylene glycol | 5 |
| Primary C12-C14 linear alcohol plus 7 ethylene oxide (EO) groups | 29.9 |
| Sum | 100 |

Different amounts of each base listed in Table 40 were added to raise the concentrate pH from the starting value (pH≤1) up to the Day 0 value seen in the first column. After the initial adjustment, some samples show moderate pH fluctuation over time, whereas other samples only show minimal pH fluctuation over time. The samples where the pH was adjusted with sodium hydroxide are examples of the overall trend. Immediately after neutralization there is a sharp decline in titrated peracid levels, demonstrated by the change from day 0 to day 7. However, after that initial drop it appears that a new reaction level is reached and for the remainder of the observation period the peracid levels stay relatively constant (compare day 7 to day 28 for all 3 of the sodium hydroxide samples.) Though the initial drop is not captured, this same period of peracid stability is demonstrated with the other bases as well. A second series of base additions can be seen in Table 41.

TABLE 40

| Base | pH | | % Peracid | | | | |
|---|---|---|---|---|---|---|---|
| | Day 0 | Day 28 | Day 0 | Day 7 | Day 14 | Day 21 | Day 28 |
| Sodium Hydroxide | 2.6 | 2.2 | 4.0 | 1.9 | 1.4 | — | 2.1 |
| Sodium Hydroxide | 3.0 | 2.3 | 3.8 | 2.4 | 2.1 | — | 2.2 |
| Sodium Hydroxide | 3.5 | 2.3 | 4.0 | 1.5 | 1.2 | — | 1.6 |
| Sodium silicate | 2.5 | 1.7 | — | — | 2.4 | 1.6 | 1.8 |
| Sodium silicate | 3.5 | 2.2 | — | — | 1.3 | 2.0 | 2.0 |
| Potassium hydroxide | 2.6 | 2.4 | — | 1.3 | 1.0 | — | 1.6 |
| Potassium hydroxide | 4.5 | 2.8 | — | 1.1 | 1.1 | — | 1.2 |

TABLE 41

| Base | pH | | % Peracid | | | | |
|---|---|---|---|---|---|---|---|
| | Day 0 | Day 28 | Day 0 | Day 7 | Day 14 | Day 21 | Day 28 |
| Sodium carbonate | 2.5 | 2.5 | — | — | 1.8 | 2 | 1.8 |
| Sodium bicarbonate | 2.5 | 1.5 | — | — | 3.3 | 3.3 | 3.2 |
| Sodium silicate | 2.5 | 1.7 | — | — | 2.4 | 1.6 | 1.8 |
| Sodium metasilicate | 2.5 | 2 | — | — | 2.4 | 2.6 | 2.6 |
| Potassium hydroxide | 2.6 | 2.4 | — | 1.3 | 1.0 | — | 1.6 |
| Sodium glutarate | 2.5 | 2.2 | — | 1.9 | 1.6 | — | 1.5 |

As with the first series of base additions, after the initial adjustment there are some examples that show pH fluctuation over time, and other examples that do not. Another similarity between the two series of base additions is the period of peracid stability after the initial drop. This period of stability is demonstrated by comparing the earliest titration values (either day 7 or day 14) with the latest measurement (day 28). The above data demonstrates relatively little change between those two time points, again suggesting that a new reaction level is reached after the initial pH adjustment.

Example 23 pH Adjustment of Combined Cleaning, Bleaching and/or Antimicrobial Compositions, Mixed Peracid System The formula studied in example 22 (Table 39) contained only a single peracid, PSOA. In some instances it may be desirable to use a composition containing multiple peracids. Therefore, the neutralization of a composition containing two peracids (POOA and PSOA) was also studied (Table 42).

TABLE 42

| | Formula L |
|---|---|
| Sulfonated oleic acid | 20 |
| 1-Octanoic acid | 4 |
| Hydrogen peroxide (50%) | 20 |

TABLE 42-continued

| | Formula L |
|---|---|
| Alkyl (C10-C16) Benzenesulfonic acid | 6 |
| pyridine-2,6-dicarboxylic acid | 0.1 |
| propylene glycol | 5 |
| Sodium cumene sulfonate | 15 |
| Primary C12-C14 linear alcohol plus 7 ethylene oxide (EO) groups | 29.9 |
| Sum | 100 |

As in the earlier example, the various bases listed in Table 43 were each added to Formula L. With this two peracid system similar trends to a single peracid system were noticed. Immediately after neutralization there was a drop in peracid levels. However, in all systems tested the level did not drop significantly from day 7 to day 28. Like the single peracid systems, when sodium carbonate or sodium bicarbonate was used as the neutralizing base the peracid level stayed essentially constant over time. By contrast, with all hydroxide bases tested the peracid levels actually rose from day 7 to day 28.

TABLE 43

| Base | pH | | % Peracid | | | | |
|---|---|---|---|---|---|---|---|
| | Day 0 | Day 28 | Day 0 | Day 7 | Day 14 | Day 21 | Day 28 |
| Lithium hydroxide | 2.1 | 2.4 | 4.9 | 2.6 | 3.2 | 3.3 | 3.5 |
| Sodium hydroxide | 2.0 | 1.9 | 5.2 | 2.5 | 2.6 | 3.2 | 3.6 |
| Potassium hydroxide | 2.3 | 1.9 | 4.9 | 2.6 | 2.8 | 3.1 | 3.4 |
| Sodium carbonate | 2.5 | 2.3 | 6.3 | 4.8 | 4.3 | — | 4.1 |
| Sodium bicarbonate | 2.7 | 2.4 | 6.1 | 4.4 | 4.4 | — | 4.0 |

To show broad scope formulation capability, another composition was created with higher levels of octanoic acid. The higher absolute peracid levels are a reflection of the lower molecular weight of octanoic acid compared to sulfonated oleic acid, meaning there are more starting moles of carboxylic acid that can be converted to the percarboxylic acid. Given that, it is apparent that the final peracid level can be varied by adjusting the amount of starting carboxylic acids. Similarly to the composition containing a lesser amount of octanoic acid (Formula L), Formula M saw a sharp drop in peracid levels immediately after neutralization. Again, after the initial drop the peracid levels did not decrease significantly from day 7 to day 28.

TABLE 44

| | Formula M |
|---|---|
| Sulfonated oleic acid | 12 |
| 1-Octanoic acid | 12 |
| Hydrogen peroxide (50%) | 20 |
| Alkyl (C10-C16) Benzenesulfonic acid | 6 |
| pyridine-2,6-dicarboxylic acid | 0.1 |
| propylene glycol | 5 |
| Sodium cumene sulfonate | 20 |
| Primary C12-C14 linear alcohol plus 7 ethylene oxide (EO) groups | 24.9 |
| Sum | 100 |

TABLE 45

| | pH | | % Peracid | | | | |
|---|---|---|---|---|---|---|---|
| Base | Day 0 | Day 28 | Day 0 | Day 7 | Day 14 | Day 21 | Day 28 |
| Lithium hydroxide | 4.0 | 1.7 | 11.3 | 6.6 | 6.0 | 6.1 | 6.5 |
| Sodium hydroxide | 2.0 | 1.5 | 10.9 | 7.5 | 7.2 | 6.7 | 7.0 |
| Potassium hydroxide | 2.1 | 1.5 | 10.8 | 7.4 | 7.0 | 7.2 | 7.3 |
| Sodium carbonate | 2.7 | 2.1 | 12.1 | 9.5 | 8.1 | — | 7.6 |
| Sodium bicarbonate | 2.9 | 2.2 | 12.0 | 8.2 | 7.9 | — | 8.2 |

Synthesis of Selected Compounds of the Invention
Preparation of the Sulfonated Peroleic Acid Product 417.8 g of OA5-R (Intertrade Organic's, 40% active Sulfonated Oleic acid) was added to a 2-L beaker immersed in a large ice-bath, to which was subsequently added, 66.4 g of Dequest 2010 (60% active Hydroxyethylenediphosphonic acid, Monsanto) and 535 g of Hydrogen peroxide (46% active, Solvay-Interox). The beaker was fitted with a magnetic stir bar and the solution was stirred aggressively while adding 940 g of sulfuric acid (96% active, Mallinkrodt). The rate of the sulfuric acid addition was controlled to produce a 120° F. exotherm in the reaction solution, and while this was occasionally exceeded by several degrees F., it wasn't allowed to exceed 125° F. Several minutes after completing the sulfuric acid addition, the ice bath was removed and the heterogenous solution was stirred for 72 hours allowing the temperature to equilibrate to ambient (70° F.) conditions.

Several hours after discontinuing the stirring, the two phase reaction solution was added to a separatory funnel and the upper and lower phase were separated. 239.4 g of upper phase were collected and the upper phase was further purified by centrifugation at 3000 rpm for 10 minutes. The final upper phase yield was 206 g and titrated as 60% Peroxyacid based upon an assumed molecular weight of 412 (theoretical yield 178 g). In addition the upper phase contained 1.8% Hydrogen peroxide. A centrifuged lower phase sample titrated as 14% Peroxyacid (MW 412) and 8.8% hydrogen peroxide.

Synthesis of 11-Sulfoundecanoic Acid and
10,11-Disulfoundecanoic Acid

11-Sulfoundecanoic Acid

Deionized water (150 ml), isopropyl alcohol (200 ml) and 11-undecylenic acid (28.56 g, 0.155 mol) were placed in a 1.0 liter flask equipped with stirrer, additional funnel, reflux condenser, thermometer and a gas inlet tube. To the additional funnel was added a premix which contained 15.2 g (0.08 mol) of sodium metabisulfite and 1.28 g of NaOH in 55 g of water. The whole device was purged with nitrogen gently. After heating to reflux (82° C.), a small portion of t-butyl perbenzoate (out of total amount of 0.5 g, 2.5 mmol) was added to the flask. Then the sodium metabisulfite/NaOH premix was added continuously over a five hour period to the reaction solution through an addition funnel. The remaining t-butyl perbenzoate was also added in small portions during this time.

The solvent was then removed under reduced pressure using a rotavapour, and the residue washed with acetone, and dried, yielding 31.0 g of white solid. NMR analysis of the solid indicated no presence of the residual raw materials. The white solid obtained was dissolved in hot water (100 ml, 75° C.), and neutralized to pH 5.5 with NaOH. Then 2.0 g of 50% $H_2O_2$ was added to the solution. The solution was then allowed to cool down to room temperature, and the solid precipitated was filtered, washed with cold water, and dried, affording 21.0 g of white solid, characterized as pure 11-sulfoundecanoic acid. $^{13}C$ NMR ($D_2O$): 180, 51, 34, 28-29 (multiple), 27.5, 24.5, 24 ppm. MS (ESI): 265.1 ($M^+$-H).

10,11-Disulfoundecanoic Acid this compound was obtained as a byproduct from the 11-Sulfoundecanoic acid reaction as described above. The filtrate, after collecting 11-sulfoundecanoic acid through filtration, was concentrated to ~50 ml when precipitate start to form. The mixture was cooled down in the refrigerator, and the additional solid formed was filtered, washed with a small amount of ice water, and dried, yielding 5.0 g of white solid. $^{13}C$ NMR ($D_2O$): 184, 57, 51.5, 37.5, 28-29 (multiple), 27.5, 26, 24 ppm. MS (ESI): 345.0.

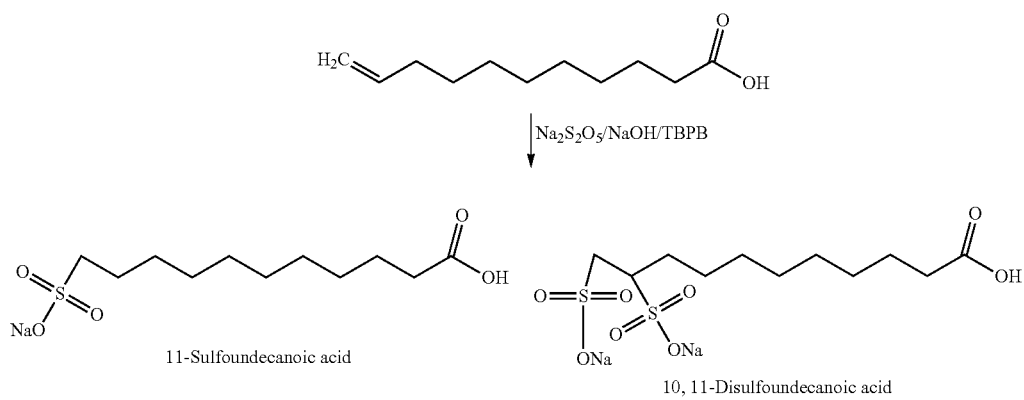

Synthesis of 11-Sulfoundecaneperoxoic Acid (Compound D) and 10,11-Disulfoundecaneperoxoic Acid (Compound E)

11-Sulfoperoxyundecanoic Acid

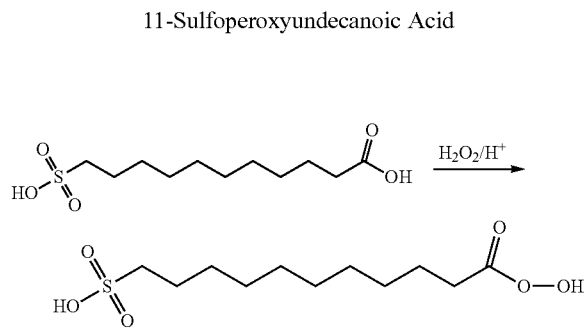

1.3 g of 11-sulfoundecanoic acid was dissolved in 2.5 g of 98% sulfuric acid. To this solution (the temperature of the solution did not exceed 60° C.) 1.5 g of 50% $H_2O_2$ was added, and the resulting mixture was stirred at room temperature for 1.5 hr. At this point, a white solid precipitated from the solution. The mixture was reheated to 50° C. with a water bath until the solution was clear. The solution was then stirred at room temperature for 0.5 hr, and cooled down in the freezer. Then 20 ml of ice water was added to the mixture, and the solid filtered, washed with ice water, and dried under vacuum, yielding 0.6 g of a white solid. $^{13}C$ NMR ($D_2O$): 176, 51.5, 30.5, 27.5-29 (multiple), 24.5, 24 ppm. MS (ESI): 281.5 ($M^+$-H). Available oxygen (iodometric): 5.41% (theoretical: 5.64%).

10,11-Disulfoundecaneperoxoic Acid (Compound E)

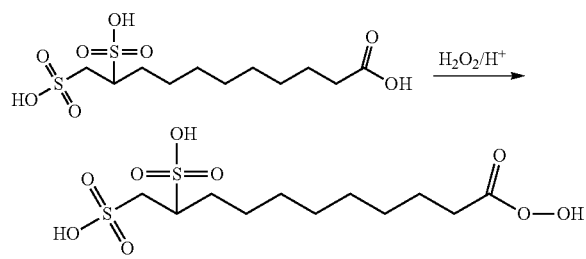

To 1.5 g of 10,11-disulfoundecanoic acid was added 2.5 g of 96% $H_2SO_4$, and the mixture was stirred at room temperature. Then 1.0 g of 50% $H_2O_2$ was added slowly (the temperature not exceeding 60° C.) to the mixture, and after addition, the mixture was heated to 50° C. with water bath, and the solution stirred for 2.0 hrs. The solution was then cooled down in the freezer, and 20 ml of ice water was added with stirring. The solid precipitated was filtered, washed with ice water, and dried under vacuum, affording 1.0 g of white solid. $^{13}C$ NMR ($D_2O$): 175.5, 57, 30.5, 27.5-29 (multiple), 24.5, 24 ppm. Available oxygen (iodometric): 4.10% (theoretical: 4.41%).

Synthesis of 9/10-Sulfostearic Acid (Sulfonated Stearic Acid)

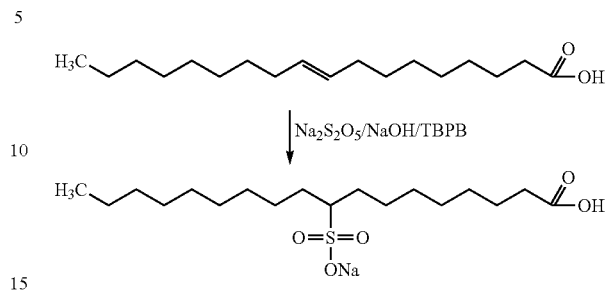

Deionized water (150 ml), isopropyl alcohol (200 ml) and oleic acid (43.78 g, 0.155 mol) were placed in a 1.0 liter flask equipped with stirrer, additional funnel, reflux condenser, thermometer and a gas inlet tube. To the additional funnel was added a premix which contained 15.2 g (0.08 mol) of sodium metabisulfite ($Na_2S_2O_5$) and 1.28 g of NaOH in 55 g of water. The whole device was bubbled gently with nitrogen. After heating to reflux (82° C.), a small portion of t-butyl perbenzoate (out of total amount of 0.5 g, 2.5 mmol) was added to the flask. Then the $Na_2S_2O_5$/NaOH premix was added through the addition funnel continuously over the course of five hours. The remaining t-butyl perbenzoate was also added in portions during this time.

The solvent was then removed under reduced pressure using rotavapour. To the residue was added 100 ml of DI water, the pH of the solution was adjusted to 2.5 with $H_2SO_4$. The resulting mixture/solution was transferred to a separation funnel, and the top oily layer (non reacted oleic acid) was removed. The aqueous layer was extracted with petroleum ether (2×50 ml), and after removal of the water, afforded 12.5 g of white waxy solid. $^{13}C$ NMR ($D_2O$): 179, 60, 34.5, 32, 28.5-30 (multiple), 24.5, 22.5, 14 ppm. MS (ESI): 363.4 ($M^+$-H).

Preparation of 9/10-Sulfoperoxystearic Acid (in Formulation)

To a 2.0 g mixture of 9 or 10-Sulfostearic acid was added 2.0 g of 50% $H_2O_2$. The mixture was stirred at room temperature until all the solid was dissolved. Then, 2.0 g of 75% $H_3PO_4$ was added, and the resulting solution was stirred at room temperature overnight. No attempt was made to isolate the pure 9 or 10-sulfoperoxystearic acid from solution. $^{13}C$ NMR ($D_2O$) of the solution showed a peracid peak (COOOH) at 174 ppm and the parent the carboxylic acid peak at 178 ppm. The iodometric titration (QATM-202) indicated 18.96% of sulfoperoxystearic acid.

The invention claimed is:

1. A laundry composition, comprising:
   (a) one or more sulfoperoxycarboxylic acids, wherein said sulfoperoxycarboxylic acids comprise at least one of the following:

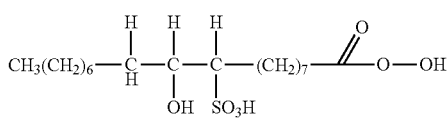

or salts thereof; or

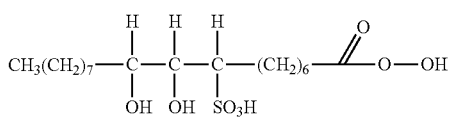

or salts thereof;
(b) an oxidizing agent; (C) a C1 to C11 carboxylic acid; (d) a surfactant; (e) a stabilizing agent.

2. The composition of claim 1 further comprising a viscosity reducer.

3. The composition of claim 1 further comprising a defoamer.

4. The composition of claim 3 wherein the defoamer is an alkyl alkoxylate containing in part or whole poly-propylene oxide units.

5. The composition of claim 1 wherein the composition is a liquid, gel or solid.

6. The composition of claim 1, wherein said one or more sulfoperoxycarboxylic acids further comprise:

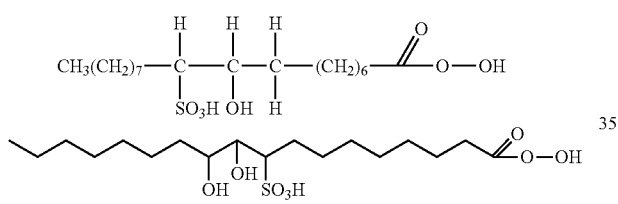

salts, esters, mixtures or derivatives thereof.

7. The composition of claim 1, wherein the pH of the composition is less than about 7.

8. The composition of claim 1, wherein the sulfoperoxycarboxylic acids are present at about 0.05 wt % to about 50 wt %.

9. The composition of claim 1, wherein, the sulfoperoxycarboxylic acids are present at about 0.05 wt % to about 30 wt %.

10. The composition of claim 1, wherein the sulfoperoxycarboxylic acids are present at about 1.0 wt % to about 20 wt %.

11. The composition of claim 1, wherein the oxidizing agent is selected from the group consisting of hydrogen peroxide, an organic peracid, an organic peroxide, and combinations thereof.

12. The composition of claim 1, wherein the carboxylic acid comprises octanoic acid.

13. The composition of claim 12, wherein the composition further comprises a $C_2$ to $C_{11}$ peroxycarboxylic acid.

14. The composition of claim 13, wherein the peroxycarboxylic acid comprises peroxyoctanoic acid, peroxynonanoic acid, peroxydecanoic acid, or combinations thereof.

15. The composition of claim 14, wherein the peroxycarboxylic acid is present at about 0.1 wt % to about 10 wt %.

16. The composition of claim 13, wherein the peroxycarboxylic acid is selected from the group consisting of peroxyacids of acetic, glycolic, butyric, hexanoic, heptanoic, salicylic, malic, mandelic, malonic, succinic, glutaric, adipic, and citric acids, and mixtures thereof.

17. The composition of claim 1, wherein the stabilizing agent is selected from the group consisting of organic amino polyphosphonic acid complexing agents, organic hydroxyl polyphosphonic acid complexing agents, and mixtures thereof.

18. The composition of claim 1, wherein the composition is substantially phosphorous free.

19. The composition of claim 1, wherein the composition comprises:
(a) about 0.05 wt % to about 50 wt % of the one or more sulfoperoxycarboxylic acids;
(b) about 0.1 wt % to about 75 wt % of the oxidizing agent;
(c) about 0.1 wt % to about 40 wt % of the $C_1$-$C_{11}$ carboxylic acid in combination with one $C_1$ to $C_{22}$ peroxycarboxylic acid;
(d) about 0.50 wt % to about 70 wt % of the surfactant;
(e) about 0.0 wt % to about 5 wt % of an additional acidulant;
(f) about 0.0 to about 10 wt % of a viscosity reducer.

20. The composition of claim 2 wherein the viscosity reducer is comprised of propylene glycol.

21. The composition of claim 1 wherein the surfactant is selected from the group consisting of nonionic surfactant, anionic surfactant, amine oxide surfactant, and mixtures thereof.

22. The composition of claim 19 wherein the acidulant (e) is selected from the group consisting of sulfuric acid, methane sulfonic acid, ethane sulfonic acid, propane sulfonic acid, butane sulfonic acid, xylene sulfonic acid, benzene sulfonic acid, linear alkyl benzene sulphonic acid, cumene sulfonic acid, xylene sulfonic acid, and combinations thereof.

23. The composition of claim 21 wherein the anionic surfactant is selected from the group consisting of linear alkyl benzene sulphonate, linear alkyl benzene sulfonic acid, and mixtures thereof.

* * * * *